(12) United States Patent
Klingelhöfer et al.

(10) Patent No.: US 9,683,032 B2
(45) Date of Patent: Jun. 20, 2017

(54) ANTI-S100A4 ANTIBODY MOLECULES AND THEIR USES

(71) Applicant: Cancer Research Technology Limited, London, Greater London (GB)

(72) Inventors: Jorg Klingelhöfer, Copenhagen (DK); Noona Ambartsumian, Copenhagen (DK); Mariam Grigorian, Copenhagen (DK); Eugene Lukanidin, Copenhagen (DK)

(73) Assignee: Cancer Research Technology Limited, London (GB)

(*) Notice: Subject to any disclaimer, the term of this patent is extended or adjusted under 35 U.S.C. 154(b) by 0 days.

(21) Appl. No.: 14/439,411

(22) PCT Filed: Oct. 29, 2013

(86) PCT No.: PCT/GB2013/052818
§ 371 (c)(1),
(2) Date: Apr. 29, 2015

(87) PCT Pub. No.: WO2014/068300
PCT Pub. Date: May 8, 2014

(65) Prior Publication Data
US 2016/0159888 A1    Jun. 9, 2016

(30) Foreign Application Priority Data
Oct. 30, 2012 (GB) .................................. 1219487.4

(51) Int. Cl.
| | | |
|---|---|---|
| *C07K 16/18* | (2006.01) | |
| *C07K 16/30* | (2006.01) | |
| *A61K 39/395* | (2006.01) | |
| *A61K 45/06* | (2006.01) | |
| *G01N 33/574* | (2006.01) | |
| *A61K 39/00* | (2006.01) | |
| *A61N 5/10* | (2006.01) | |

(52) U.S. Cl.
CPC ........ *C07K 16/18* (2013.01); *A61K 39/39558* (2013.01); *A61K 45/06* (2013.01); *C07K 16/30* (2013.01); *G01N 33/57415* (2013.01); *A61K 2039/505* (2013.01); *A61N 2005/1098* (2013.01); *C07K 2317/24* (2013.01); *C07K 2317/30* (2013.01); *C07K 2317/33* (2013.01); *C07K 2317/34* (2013.01); *C07K 2317/76* (2013.01); *C07K 2317/92* (2013.01); *G01N 2333/4727* (2013.01)

(58) Field of Classification Search
CPC ... C07K 16/18; C07K 16/30; A61K 39/39558
See application file for complete search history.

(56) References Cited

U.S. PATENT DOCUMENTS

| | | | | |
|---|---|---|---|---|
| 7,935,796 B2 * | 5/2011 | Lee | .................. | C07K 16/22 530/387.1 |
| 8,093,360 B2 * | 1/2012 | Casey | ................ | C07K 16/1278 424/133.1 |

FOREIGN PATENT DOCUMENTS

| | | |
|---|---|---|
| WO | 00/70352 | 11/2000 |
| WO | 2009/109862 A2 | 9/2009 |
| WO | 2011/157724 A1 | 12/2011 |
| WO | WO2011/157724 A1 * | 12/2011 |

OTHER PUBLICATIONS

Almagro & Fransson, Frontiers in Bioscience 2008; 13:1619-33.*
De Genst et al., Dev Comp Immunol 2006; 30:187-98.*
PJ Carter, Nat Rev Immunol, 2006; 6:343-357.*
E. A. Padlan, Adv Prot Chem 49:57-133; 1996.*
Al-Hajj, Muhammad et al., "Prospective identification of tumorigenic breast cancer cells", PNAS, 100(7): 3983-3988 (2003).
Ambartsumian, Noona et al., "The metastasis-associated Mts1(S100A4) protein could act as an angiogenic factor", Oncogene, 20: 4685-4695 (2001).
Boye, Kjetil et al., "Nuclear S100A4 is a novel prognostic marker in colorectal cancer", European Journal of Cancer, 46: 2919-2925 (2010).
Cabezon, Teresa et al., "Expression of S100A4 by a variety of cell types present in the tumor microenvironment of human breast cancer", Int. J. Cancer, 121: 1433-1444 (2007).
Dmytriyeva, Oksana et al., "The metastasis-promoting S100A4 protein confers neuroprotection in brain injury", Nat. Commun., 3: 1197 doi: 10.1038/ncomms2202 (2012).
Donato, Rosario, "Intracellular and Extracellular Roles of S100 Proteins", Microscopy Research and Technique, 60: 540-551 (2003).
Ebralidze, Alexander et al., "Isolation and characterization of a gene specifically expressed in different metastatic cells and whose deduced gene product has a high degree of homology to a Ca2+-binding protein family", Genes & Development, 3: 1086-1093 (1989).
Ghoreschi, Kamran et al., "Janus kinases in immune cell signaling", Immunological Reviews, 228: 273-287 (2009).
Grum-Schwensen, Birgitte et al., Suppression of Tumor Development and Metastasis Formation in Mice Lacking the S100A4(mts1) Gene, Cancer Res., 65(9): 3772-3780 (2005).
Grum-Schwensen, Birgitte et al., "Lung Metastasis Fails in MMTV-PyMT Oncomice Lacking S100A4 Due to a T-Cell Deficiency in Primary Tours", Cancer Res., 70(3): 936-947 (2010).
Harris, Molly A. et al., "Cancer Stem Cells Are Enriched in the Side Population Cells in a Mouse Model of Glioma", Cancer Res., 68(24): 10051-10059 (2008).

(Continued)

*Primary Examiner* — Jessica H Roark
(74) *Attorney, Agent, or Firm* — Patrick J. Hagan; Dann, Dorfman, Herrell and Skillman

(57) ABSTRACT

Anti-S100A4 antibody molecules that are capable of inhibiting the biological activity of S100A4 in promoting tumor progression and/or in inducing tumor metastasis are described. The antibody molecules are also useful in the treatment of inflammatory conditions. The properties of the antibodies are demonstrated using in vitro and in vivo assays.

26 Claims, 14 Drawing Sheets

(56) References Cited

OTHER PUBLICATIONS

Helfman, D.M. et al., "The metastasis associated protein S100A4: role in tumour progression and metastasis", British Journal of Cancer, 92: 1955-1958 (2005).

Jimeno, Rebeca et al., "Effect of VIP on the balance between cytokines and master regulators of activated helper T cells", Immunology and Cell Biology, 90: 178-186 (2012).

Kaplan, Rosandra N. et al., "VEGFR1-positive haematopoietic bone marrow progenitors initiate the pre-metastatic niche", Nature, 438: 820-827 (2005).

Kaplan, Rosandra N. et al., "Preparing the "Soil": The Premetastatic Niche", Cancer Res., 66(23): 11089-11093 (2006).

Kiss, Bence et al., "Crystal structure of the S100A4-nonmuscle myosin IIA tail fragment complex reveals an asymmetric target binding mechanism", PNAS, 109(16): 6048-6053 (2012).

Klingelhofer, Jorg et al., "Epidermal growth factor receptor ligands as new extracellular targets for the metastasis-promoting S100A4 protein", FEBS Journal, 276: 5936-5948 (2009).

Kriajevska, Marina et al., "Metastasis-associated Mts1 (S100A4) Protein Modulates Protein Kinase C Phosphorylation of the Heavy Chain of Nonmuscle Myosin", The Journal of Biological Chemistry, 273(16): 9852-9856 (1998).

Langley, Robert R. et al., "The seed and soil hypothesis revisited—the role of tumor-stroma interactions in metastasis to different organs", Int. J. Cancer, 128(11): 2527-2535 (2011).

Lo, Jeng-Fan et al., "The Epithelial-Mesenchymal Transition Mediator S100A4 Maintains Cancer-Initiating Cells in Head and Neck Cancers", Cancer Res., 71(5): 1912-1923 (2011).

Maelandsmo, Gunhild et al., "Different Expression and Clinical Role of S100A4 in Serous Ovarian Carcinoma at Different Anatomic Sites", Tumor Biol., 30: 15-25 (2009).

Malanchi, Harla et al., "Interactions between cancer stem cells and their niche govern metastatic colonization", Nature, 481: 85-89 (2012).

Malashkevich, Vladimir N. et al., "Structure of Ca2+-Bound S100A4 and its Interaction with Peptides Derived from Nonmuscle Myosin-IIA+", Biochemistry, 47(18): 5111-5126 (2008).

Mazzucchelli, Luca et al., "Protein S100A4: Too Long Overlooked by Pathologists?", American Journal of Pathology, 160(1): 7-13 (2002).

Mishra, Shrawan Kumar et al., "S100A4 calcium-binding protein is key player in tumor progression and metastasis: preclinical and clinical evidence", Cancer Metastasis Rev., 31: 163-172 (2012).

Moller, Henrik Devitt et al., "Role of Fibulin-5 in Metastatic Organ Colonization", Mol. Cancer Res., 9(5): 553-563 (2011).

Pathuri, Puja et al., "Crystal structure of metastasis-associated protein S100A4 in the active, calcium-bound form", J. Mol. Biol., 383(1): 62-77 (2008).

Reya, Tannishtha et al., "Wnt signalling in stem cells and cancer", Nature, 434: 843-850 (2005).

Rubinstein, Nimrod D. et al., "Computational characterization of B-cell epitopes", Molecular Immunology, 45: 3477-3489 (2008).

Rubinstein, Nimrod D. et al., "Epitopia: a web-server for predicting B-cell epitopes", BMC Bioinformatics, vol. 10 (2009).

Schmidt-Hansen, Birgitte et al., "Functional Significance of Metastasis-inducing A100A4(Mts1) in Tumor-Stroma Interplay", The Journal of Biological Chemistry, 279 (23): 24498-24504 (2004).

Schmidt-Hansen, Birgitte et al., "Extracellular S100A4(mts1) stimulates invasive growth of mouse endothelial cells and modulates NMP-13 matrix metalloproteinase activity", Oncogene, 23: 5487-5495 (2004).

Sherbet, G.V. et al., "Metastasis promoter S100A4 is a potentially valuable molecular target for cancer therapy", Cancer Letters, 280: 15-30 (2009).

Stam, J.C. et al., "Invasion of T-lymphoma cells: cooperation between Rho family GTPases and lysophospholipid receptor signaling", The EMBO Journal, 17(14): 4066-4074 (1998).

Valastyan, Scott et al., "Tumor Metastasis: Molecular Insights and Evolving Paradigms", Cell, 147: 275-292 (2011).

Zhu, Jinfang et al., "CD4 T cells: fates, functions, and faults", Blood, 112(5): 1557-1569 (2008).

de Silva Rudland, R.S. et al., "Association of S100A4 and Osteopontin with Specific Prognostic Factors and Survival of Patients with Minimally Invasive Breast Cancer", Clin. Cancer Res., 12: 1192-1200 (2006).

Tsuna, M. et al., "Significance of S100A4 as a Prognostic Marker of Lung Squamous Cell Carcinoma", Anticancer Research, 29: 2547-2554 (2009).

Klingelhofer, J. et al., "Anti-S100A4 Antibody Suppresses Metastasis Formation by Blocking Stroma Cell Invasion", Neoplasia, 14(12): 1260-1268 (2012).

Hernandez, Jose Luis et al., Therapeutic Targeting of Tumor Growth and Angiogenesis with a Novel Anti-S100A4 Monoclonal Antibody, PLOS One, 8(9): e72480-e72480 (2013).

Paus, Elisabeth et al., "TD-11 workshop report: characterization of monoclonal anibodies to S100 proteins", Tumor Biol., 32: 1-12 (2011).

International Search Report/Written Opinion, dated Feb. 17, 2014, issued in corresponding International Application No. PCT/GB2013/052818, filed Oct. 29, 2013.

Search Report, dated Feb. 26, 2013, issued in corresponding GB Application No. 1219487.4.

\* cited by examiner

A.

|  | IgG contr. | mAb 6B12 | significance |
|---|---|---|---|
| number of mice (N) | 21 | 20 | |
| average tumor size [mm³] | 257.1 ± 27.09 | 332.7 ± 38.86 | ns |
| metastasis free animals | 4/21 (19.1%) | 9/20 (45.0%) | |
| metastatic burden [%] | 1.510 ± 0.4845 | 0.2700 ± 0.0907 | p= 0.0197 |

B.

C.

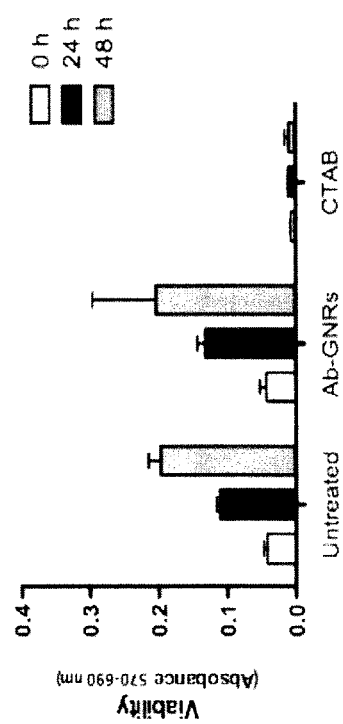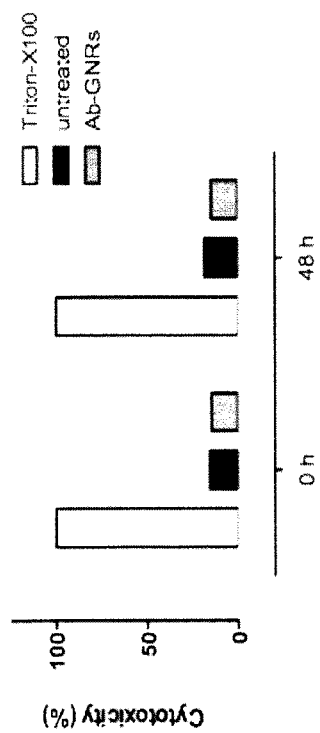
Fig. 7A
Fig. 7C
Fig. 7B
Fig. 7D
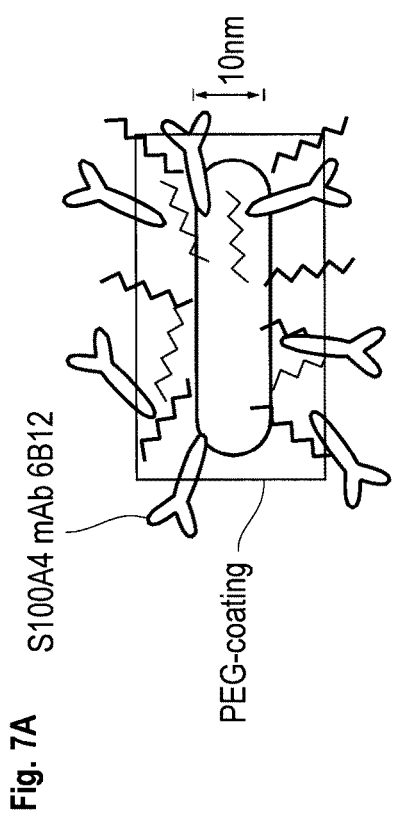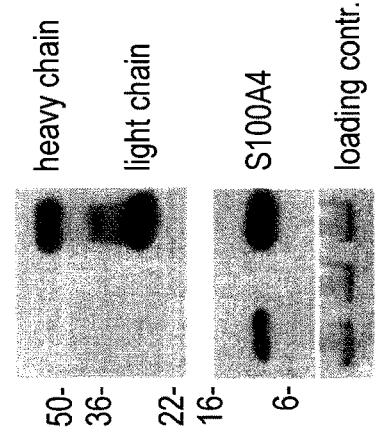

ANTI-S100A4 ANTIBODY MOLECULES AND THEIR USES

FIELD OF THE INVENTION

The present invention relates to anti-S100A4 antibody molecules and their medical uses, and more particularly to anti-S100A4 antibody molecules that are capable of inhibiting the biological activity of S100A4, for example in promoting tumour progression and/or in inducing tumour metastasis, and their uses in the treatment of cancer, in particular metastatic cancer, and inflammatory conditions. Conjugates of the antibody molecules and their uses are also provided.

BACKGROUND OF THE INVENTION

More that 90% of cancer-related deaths are caused by dissemination of cancer cells to distant organs with subsequent formation of secondary tumours. In contrast to the primary tumour, metastasis is largely incurable because of its systemic nature and its frequent association with resistance to existing therapeutic agents. The better understanding of the mechanisms of metastatic spread of cancer cells and the pathways involved in this process had identified new targets and opened new possibilities to treat cancer. Dissemination of cancer cells in the body inevitably occurs via interaction with the surrounding "normal" cells, collectively called cancer-associated stroma (Langley & Fidler, 2011). This means that the search for potential therapeutic targets for anti-metastatic therapy has considered both tumour- and stroma-cell derived molecules.

Among potentially applicable anti-metastatic targets, the protein S100A4 has been suggested as a therapeutic intervention site to prevent metastasis. S100A4 belongs to the S100 family of small Ca-binding proteins with diverse extra- and intra-cellular function (Donato, 2003). Numerous studies connect the S100A4 activity with tumour progression and metastasis formation. This evidence has been accumulated using in vitro studies of cancer cell lines, transgenic and knockout mouse models and assessment of its prognostic significance for metastasis in patients with cancer (Boye et al., 2010; Helfman et al, 2005; Mishra et al., 2011). The S100A4 activity is associated with stimulation of cancer cell motility and invasion, normal and aberrant proliferation, apoptosis and differentiation. It is involved in signaling pathways leading to the remodeling of the cell membrane and the extracellular matrix; modulation of cytoskeletal dynamics, acquisition of invasiveness and induction of angiogenesis (Sherbet, 2009). It has been shown that S100A4 is expressed in certain tumour cells, but more generally it is activated and secreted from certain cancer-associated stroma cells which lead to its accumulation in the tumour microenvironment. Moreover, it has been shown that metastatic microenvironment contains greater numbers of S100A4-positive stromal cells than the primary tumour microenvironment (Cabezón et al., 2007; Grum-Schwensen et al., 2005; 2010; Maelandsmo et al., 2009; Schmidt-Hansen, et al., 2004a).

Furthermore, S100A4 has been shown to maintain the stemness properties and tumourigenicity of cancer-initiating cells in head and neck cancers (Lo et al., 2011).

WO 2011/157724 (Lykera Biomed SA) describes anti-S100A4 antibodies that have anti-angiogenic activity and which bind an epitope comprising the amino acid sequence ELPSFLGKRT (SEQ ID NO: 16) or EGFPDKQPRKK (SEQ ID NO: 17).

However, while the role of S100A4 in tumour progression and metastasis formation has been studied, it remains the case that anti-metastatic therapy is in a rudimentary state largely unmet by existing therapies.

SUMMARY OF THE INVENTION

Broadly, the present invention is based on the present inventors developing anti-S100A4 antibody molecules that are capable of inhibiting the biological activity of S100A4 in promoting tumour progression and/or in inducing tumour metastasis. The present invention further shows that the antibodies of the present invention are capable of delaying and/or inhibiting tumour development and growth. These properties of the antibodies are demonstrated using in vitro and in vivo assays.

Accordingly, in a first aspect, the present invention provides an isolated antibody molecule which specifically binds to S100A4 polypeptide, wherein the antibody is capable of inhibiting the biological activity of S100A4 in inducing tumour metastasis. Other features and properties of the antibodies are described below. More particularly, in one aspect, the present invention provides an isolated antibody molecule which specifically binds to S100A4 polypeptide, wherein the antibody is capable of inhibiting the biological activity of S100A4, wherein the antibody molecule comprises:

(a) a CDR-H1 having the amino acid sequence of SEQ ID NO: 1, or the amino acid sequence of SEQ ID NO: 1 with one or more amino acid substitutions, deletions or insertions; and/or (b) a CDR-H2 having the amino acid sequence of SEQ ID NO: 2, or the amino acid sequence of SEQ ID NO: 2 with one or more amino acid substitutions, deletions or insertions; and/or (c) a CDR-H3 having the amino acid sequence of SEQ ID NO: 3, or the amino acid sequence of SEQ ID NO: 3 with one or more amino acid substitutions, deletions or insertions; and/or (d) a CDR-L1 having the amino acid sequence of SEQ ID NO: 4, or the sequences of SEQ ID NO: 4, with one or more amino acid substitutions, deletions or insertions; and/or (e) a CDR-L2 having the amino acid sequence of SEQ ID NO: 5, or the sequences of SEQ ID NO: 5, with one or more amino acid substitutions, deletions or insertions; and/or (f) a CDR-L3 having the amino acid sequence of SEQ ID NO: 6, or the sequences of SEQ ID NO: 6, with one or more amino acid substitutions, deletions or insertions.

In a further aspect, the present invention provides an isolated antibody molecule which specifically binds to S100A4 polypeptide, wherein the antibody is capable of inhibiting the biological activity of S100A4, wherein the antibody molecule comprises (a) a CDR-H1, a CDR-H2 and a CDR-H3 having the amino acid sequences set out in SEQ ID NO: 7, optionally with one or more amino acid substitutions, deletions or insertions and (b) a CDR-L1, a CDR-L2 and a CDR-L3 having the amino acid sequences set out in SEQ ID NO: 9, optionally with one or more amino acid substitutions, deletions or insertions.

Generally, the biological activity of S100A4 is in promoting tumour progression and/or in inducing tumour metastasis, although the antibodies and conjugates disclosed herein may be used in the treatment of other conditions mediated by aberrant or overexpression of S100A4 polypeptide. Alternatively or additionally, the antibody molecules of the present invention are capable of delaying and/or inhibiting tumour development and growth.

In some embodiments, the antibody molecule comprises a VH domain comprising a CDR-H1, CDR-H2 and CDR-H3 having the sequences of SEQ ID NOs 1, 2 and 3, respectively, and/or a VL domain comprising a CDR-L1, CDR-L2 and CDR-L3 having the sequences of SEQ ID NOs 4, 5 and 6, respectively, wherein amino acid sequence of the CDRs of the antibody molecule may optionally comprise 1, 2, 3, 4, 5, 6, 7, 8, 9 or 10 amino acid substitutions, deletions or insertions as compared to any one of SEQ ID NOs: 1 to 6.

In a further aspect, the present invention provides an isolated antibody molecule which specifically binds to S100A4 polypeptide, wherein the antibody is capable of inhibiting the biological activity of S100A4 in promoting tumour progression and/or in inducing tumour metastasis, wherein the antibody is capable of binding an epitope contained within, or at least partially contained within, the S100A4 sequence having the amino acid sequence from amino acids 66 and 89 inclusive of SEQ ID NO: 11 or SEQ ID NO: 12. In this or other aspects of the present invention, the antibody molecule is preferably capable of binding to S100A4 peptides having the amino acid sequence RDNEVDFQEYCV (SEQ ID NO: 13) and/or FLSCIAM-MCNEF (SEQ ID NO: 14), and more preferably where the antibody is capable of binding to an epitope represented by $_{71}$D-sequence $_{66}$R-N- - - -Q- - -V- - -CI- -MM-NEF$_{89}$ (SEQ ID NO: 15), wherein the dashes indicate amino acids not present in the planar level of the epitope surface and not accessible for the antibody binding.

In a further aspect, the present invention provides a pharmaceutical composition comprising an antibody molecule as disclosed herein and a pharmaceutically acceptable excipient.

In a further aspect, the present invention provides an antibody molecule conjugate comprising an antibody molecule of the present invention directly or indirectly linked or associated with a drug, a toxin, a nanoparticle, a radioisotope and/or a fluorescent label. In a preferred embodiment, the conjugate is formed with a gold nanorod or nanoparticle.

In a further aspect, the present invention provides an antibody molecule or an antibody molecule conjugate as disclosed herein for use in a method of treatment of the human or animal body.

In a further aspect, the present invention provides an antibody molecule or an antibody molecule conjugate as disclosed herein for use in a method of treatment of a condition mediated by S100A4.

In a further aspect, the present invention provides the use of an antibody molecule or an antibody molecule conjugate as disclosed herein in the manufacture of a medicament for use in treating a condition mediated by S100A4.

In a further aspect, the present invention provides a method of treating an individual with a condition mediated by S100A4. comprising administering an antibody molecule or an antibody molecule conjugate as disclosed herein to an individual in need thereof.

In the medical uses and methods of treatment of the present invention, preferably the condition mediated by S100A4 is cancer, and more particularly where the cancer is gastric cancer, pancreatic cancer, colorectal cancer, thyroid cancer, breast cancer, squamous cell carcinoma, non-small cell lung cancer, prostate cancer, lung cancer, head and neck cancer, brain cancer (including glioblastoma multiforme), renal cell carcinoma (including clear cell renal carcinoma), melanoma, lymphoma, plasmocytoma, sarcoma, glioma, thymoma, leukemia, colon cancer, esophageal cancer, ovary cancer, cervical cancer or hepatoma. As demonstrated herein, by targeting S100A4, the antibody molecules of the present invention are capable of inhibiting the biological activity of S100A4 in promoting tumour progression and/or in inducing tumour metastasis, and are therefore particularly useful in the treatment of metastatic cancer. S100A4 mediated conditions further includes inflammatory diseases, such as rheumatoid arthritis, psoriasis and inflammatory myopathies.

In a further aspect, the present invention provides the use of an antibody molecule of the present invention in an assay for diagnosis or prognosis of a S100A4 related condition in an individual.

In a further aspect, the present invention provides a method for diagnosis or prognosis of a S100A4 related condition in an individual, the method comprising (a) contacting a biological sample from the individual with an anti-S100A4 antibody molecule of the present invention which is capable of binding to S100A4 polypeptide present in the sample and (b) determining the presence and/or amount of the complex formed between the antibody molecule and the S100A4 polypeptide. Particular applications of these assays are described in more detail below.

Embodiments of the present invention will now be described by way of example and not limitation with reference to the accompanying figures. However various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

BRIEF DESCRIPTION OF THE FIGURES

FIG. 7: Synthesis and characterization of antibody-targeted GNR. (A) Scheme of an antibody functionalized GNR. The 6B12 antibody is coupled via the OPSS-PEGNHS linker to the gold surface of GNR. To enhance the biocompatibility the surface of the GNR has a PEG coating. (B) Western blot of a S100A4 pull-down assay showing that the 6B12 antibody-coupled GNRs (GNR-PEG-Ab) specifically pulled down S100A4 protein. Bare GNR, GNR-CTAB; pegylated GNR without antibody, GNR-PEG. Upper panel shows the detection of the heavy chain (Hc) and light chain (Lc) in the antibody-coupled GNR sample indicating an efficient coupling process. Lower panel is the loading control showing the GNR in the pocket of the stacking gel. (C) and (D) Determination of the cytotoxicity of the antibody-targeting GNRs. (C) MTT assay to determine viability of MEFs after different time (0, 12, 24 hrs) of treatment. (D) The LDH assay was used to detect a cytotoxicity of the GNRs.

Table 1. Pilot study comparing the effect of different anti-S100A4 mAb on tumour growth and metastasis formation. For testing the efficacy of the anti-S100A4 mAb, 3B1C4, 11F.8.3 and 6B12 a spontaneous metastasis model based on the subcutaneous (s.c.) injection of highly metastatic CSML100 cells (1×10$^6$) was used. At the time of s.c. implanting of tumour cells the antibodies were administered 3 times a week by intraperitoneal injections (7.5 mg Ab/kg mice). After 33 days animals were sacrificed and the metastatic burden in the lungs was analysed for each group. The tumour size did not differ significantly between the groups. In contrast the assessment of the metastatic burden in the lungs from mice treated with the three antibodies exhibited substantial relative difference. Mice treated with the 11F8.3 antibody showed the highest metastatic burden in lungs. The 3B1C4 antibody showed a weak tendency in metastasis neutralising activity, while the 6B12 antibody showed the most pronounced tendency in suppression of metastasis. Comparison of the 6B12 and the 11F8.3 treated groups displayed a 10-fold lower metastatic burden even though the difference was not statistically significant (note: ns p=0.052). The mean body weight at the end of the experiment of the mice between the different groups different only marginal, less than 3 percent points. No significant toxicity was monitored during the experiment.

Table 2. Analysis of the 3D structure of dimeric S100A4. Residues of the potential 6B12 interaction side identified by peptide screening (1. column). For the structural analyses we used the calcium-bound dimeric S100A4 with the PDB ID: 2Q91 (Malashkevich et al., 2008). Residues of the dimeric interface of S100A4 involving helix 4-4' and helix 1-4' are indicated in column two and three, respectively. Non-solvent exposed residues and residues which are not in the planar level of the epitope surface are indicated in column four. These residues were not accessible for the antibody binding. The conclusion of the analysis is shown in column five indicating a segmented sequence with potential epitope forming residues of the 6B12 antibody.

Table 3: Cytokine antibody array analysis of conditioned medium from the pre-metastatic lung organotypic cultures. Data shows fold changes after normalization to the background and positive controls.

Table 4: Summarizing the results of the kinetic and affinity assessment of different anti-S100A4 mAbs to immobilized S100A4 by SPR. The KD values were calculated from the individual Ka and Kd values. To indicate the confidence of the fitting the Chi2 value is indicated and is in all cases less then 10% of Rmax. The append association/dissociation constants were calculated from fittings curves using simple (1:1) fitting models. *human S100A4 protein specific.

DETAILED DESCRIPTION

S100A4 as a Target

Figure 5:
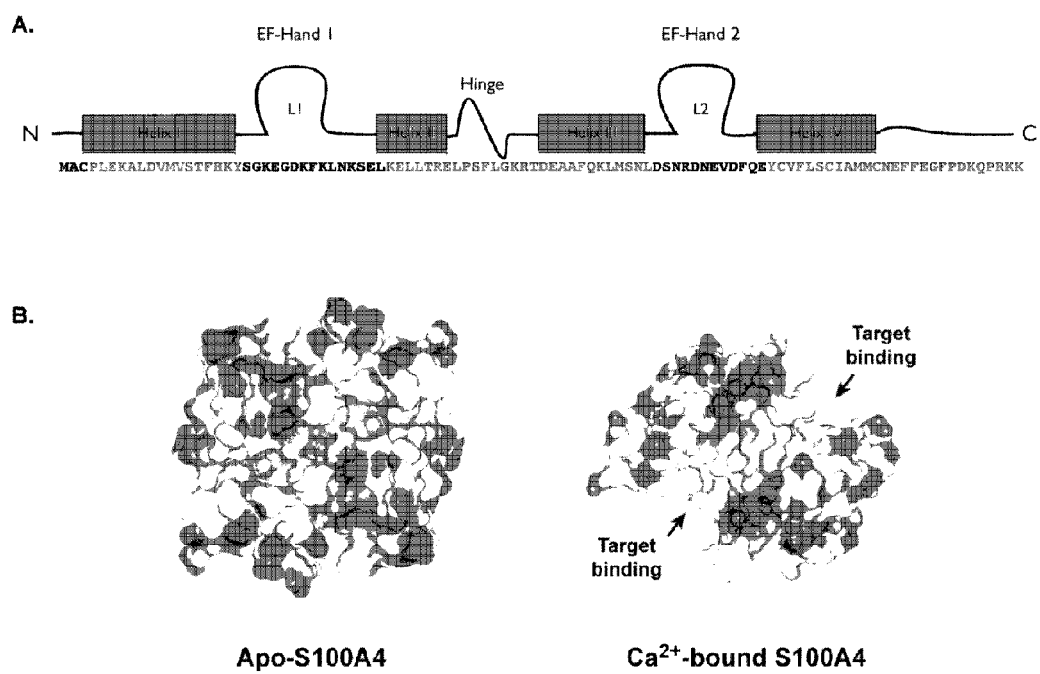
FIG. 5. The structure of the S100A4 protein. (A) Structural organization of the S100A4 monomeric subunit containing two pairs of α-helices forming the EF-hand Ca-binding sites, separated by the hinge region and ended by the less conserved C-terminal. The amino acid sequence of the S100A4 (101 amino acids) is shown underneath (SEQ ID NO: 11). (B) Electrostatic surface potential representations of apo- and $Ca^{2+}$-bound dimeric S100A4. $Ca^{2+}$ binding induces a profound conformational change, enabling the S100A4 dimer to accommodate two target molecules (indicated by arrows). Red, blue and white areas indicate negatively charged, positively charged and hydrophobic regions, respectively. Modified from Pathuri et al., 2008).
Figure 6:
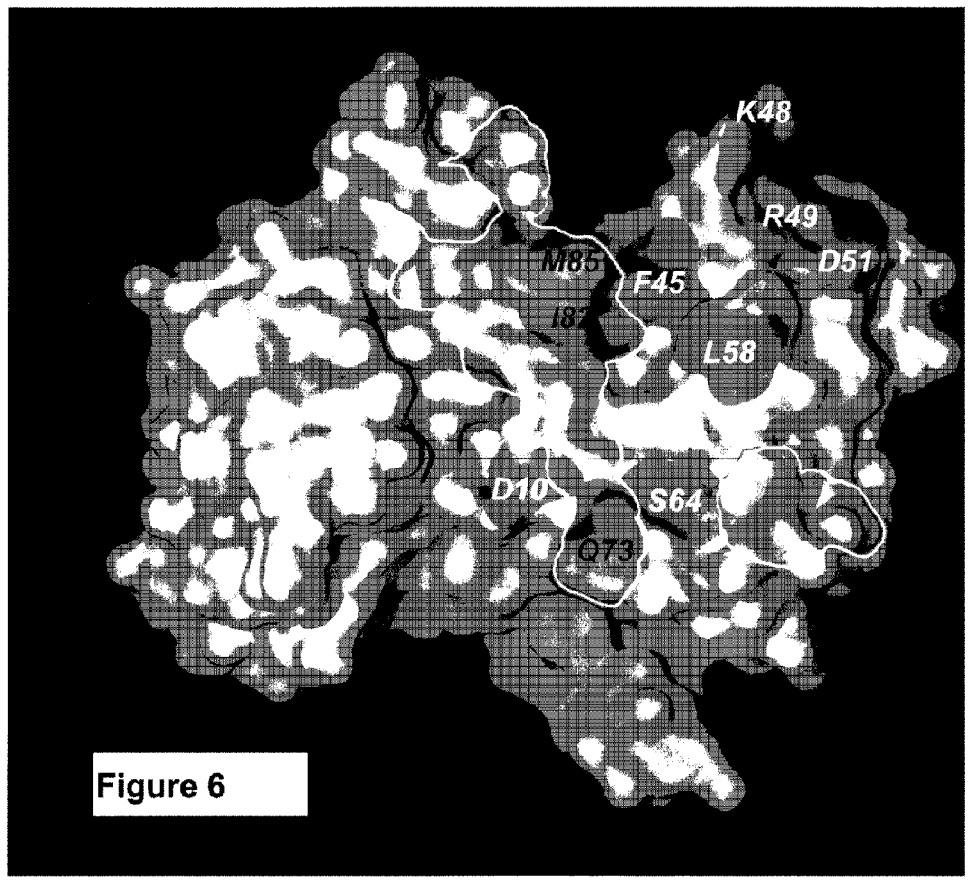
FIG. 6. Target binding interface of non-muscle myosin IIA overlaps with the predicted epitope for the 6B12 mAb. Surface modulation of calcium-bond dimeric S100A4. The residues of the myosin target binding interface are indicated in red. The outline is indicating the predicted epitope of the 6b12 mAb. The residues of S100A4, Ile82, Met85 and Gln83, which interact with myosin and overlap with the epitope are indicated in red. All other residues interacting with myosin are labeled white. The binding interface was resolved by crystal structure of the S100A4-nonmuscle myosin IIA tail fragment complex (Kiss et al., 2012).

S100A4 belongs to the S100 family of small Ca-binding proteins (Donato, 2003). S100A4 promotes cell proliferation, migration, survival, and differentiation. S100A4 shares structural features common to the S100 family which are characterized by the presence of two distinct $Ca^{2+}$-binding motifs of the EF hand type separated by a short less conserved hinge region (FIG. 5A). The prevailing intracellular form of S100A4 is a homodimer, consisting of two monomers held together in an antiparallel orientation by a hydrophobic dimerization interface. $Ca^{2+}$ binding of the S100A4 dimer induces a profound conformational change revealing two symmetrically positioned hydrophobic pockets (FIG. 5B), which interact with multiple intracellular target proteins, e.g. non-muscle myosin or the tumour suppressor protein p53 (7-10). The amino acid sequence of human S100A4 is shown in SEQ ID NO: 11 and the amino acid sequence of murine S100A4 is shown in SEQ ID NO: 12.

The S100A4 seems to externalize by an unusual route involving microparticle shedding. The dimers of S100A4 protein is also able to self-associate into oligomeric structures which have been shown to be extracellularly active and induce multiple cellular responses.

In humans S100A4 is expressed in various solid tumours and its presence is associated with a bad prognosis for the cancer patient (Mazzucchelli et al., 2002; Sherbet, 2009; Mishra et al., 2011). Substantial numbers of patients exhibiting a positive correlation of S100A4 with disease in many forms of cancer, see table below

| Disease | Percentage of patients exhibiting a positive correlation of S100A4 with disease |
|---|---|
| Gastric cancer | 55-82 |
| Pancreatic cancer | 51-93 |
| Colorectal cancer | 56-83 |
| Thyroid cancer | 62-86 |
| Breast cancer | 45-65 |
| Squamous cell carcinoma | 27 |
| Non-small cell lung cancer | 71 |
| Prostate cancer | 76 |
| Lung cancer | 55-60 |
| Renal cell carcinoma | 34 |

Nonetheless, numerous experimental approaches, including in vitro studies and transgenic mouse models, have verified a causal implication of S100A4 in metastasis formation. These studies revealed that both intracellular and extracellular S100A4 activates and integrates pathways that generate a phenotypic response characteristic for cancer metastasis. Indeed S100A4 activity is associated with maintaining cancer-initiating cells, epithelial mesenchymal transition (EMT), tumour cells motility and invasion. It is involved in signaling pathways leading to the activation of the Nf-kB transcription factor, stimulation and secretion of matrix metalloproteinases, modulation of cytoskeletal dynamics, induction of angiogenesis. It has been shown that S100A4 is expressed in certain tumour cells, but more generally it is activated and secreted from cancer-associated stroma cells which goes along with an enhanced accumulation of S100A4 in the tumour microenvironment.

Using different S100A4-deficient mouse models direct evidence has been obtained for an essential function of S100A4 in metastasis and cancer progression. These models clearly indicate that metastasis formation is strongly reduced in a S100A4 deficient background. The development of tumour stroma was affected in S100A4 knock-out animals. By co-injection of S100A4-positive fibroblasts the ability of tumours to metastasize was restored, highlighting S100A4s as an essential tumour microenvironmental factor for metastasis. Moreover, a consequence of the enhance expression and release of S100A4 from tumour and stroma cells is the recruitment of cells of the immune system. Importantly, the infiltration of macrophages and T-cells into the tumour microenvironment was not observed in S100A4-deficient mice.

The present inventors realised that the fundamental role in tumour progression makes the S100A4 protein an attractive target for an anti-metastatic therapy and accordingly set out to produce antibody molecules that were capable of binding to S100A4 protein and inhibiting the biological activity of S100A4 in promoting tumour progression and/or in inducing tumour metastasis. Alternatively or additionally, the antibody molecules of the present invention are capable of delaying and/or inhibiting tumour development and growth. The work described herein demonstrates that an exemplified MAb 6B12 was capable of reducing the number of metastases in a mouse xenograft model and was capable of inhibition of T cell recruitment to the tumour site.

Anti-S100A4 Antibody Molecules

Figure 1:
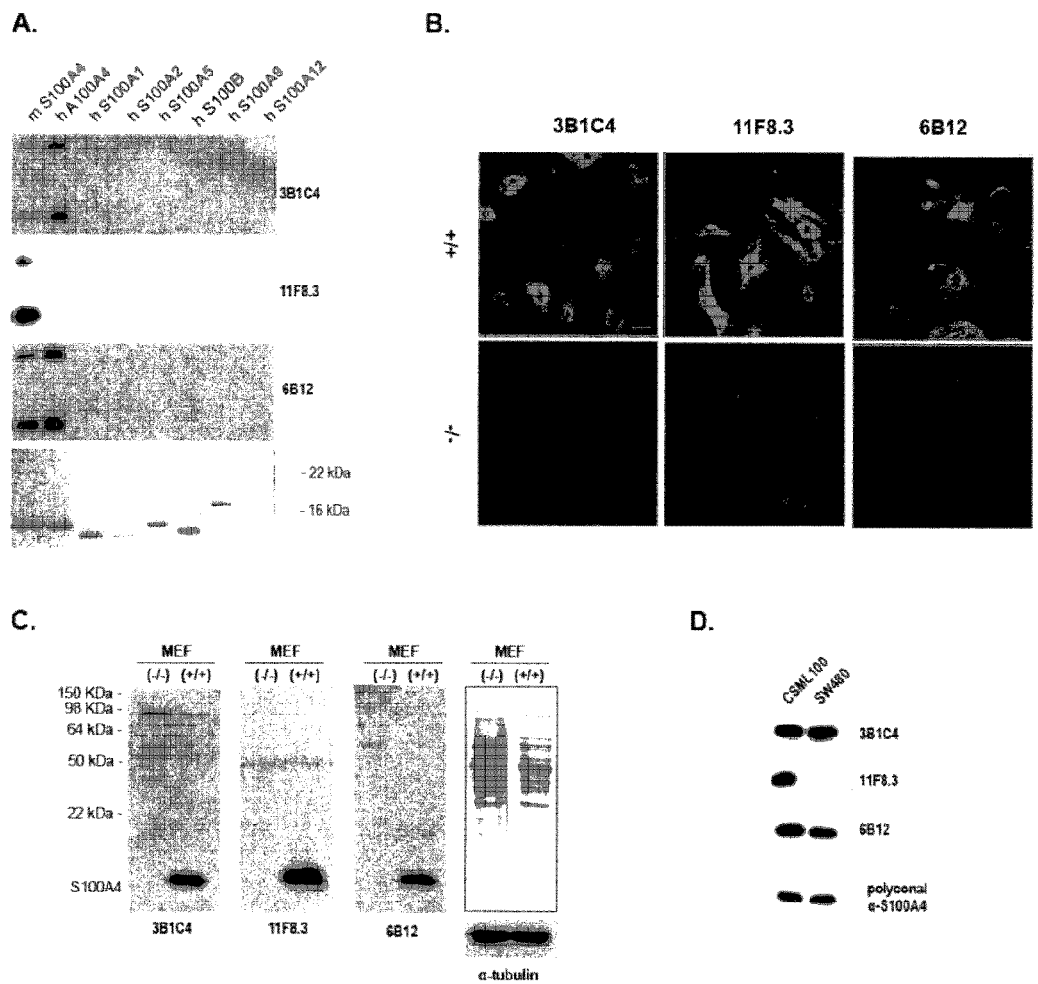
FIG. 1. Characterization of three different clones recognizing S100A4. (A) The mAB 3B1C4 and 6B12 recognizes both mouse and human S100A4 protein, while the 11F8.1 reacts exclusively with the mouse protein. All three antibodies show no cross reactivity to other S100 family members. Lower panel amido black staining of the PVDF membrane is serving as loading control. (B) Immunofluorescence staining of MEFs for S100A4 using the S100A4 antibodies (green) as indicated. All antibodies recognize endogenous S100A4 protein in wild-type mouse embryonic fibroblasts, MEFs(+/+). The staining pattern of cytoplasmic expressed S100A4 is similar. All antibody displayed highly specificity in this assay, since they did not cross-react with proteins of S100A4 knock-out fibroblasts, MEFs(−/−). F-actin is stained by rhodamine-phalloidin (red) and the nucleus by DAPI (blue). (C) The specificities of the antibody were further confirmed by Western blotting, where similar result were obtained, when comparing cell extract from MEF(+/+) and MEF(−/−) cells. Note: the 3BIC4 mAb cross-react in cell extract from S100A4 knock-out fibroblast some protein band with a size about 55 and 96 kDa. The coomassie blue and α-tubulin stains are serving as loading controls. (D) All mAbs were able to detect endogenous S100A4 protein from cell extracts. As expected the 11F8.3 did not cross-react with the human protein. CSML100, mouse mammary adenocarcinoma cell line; SW480, human colon carcinoma cell line.
Figure 2:
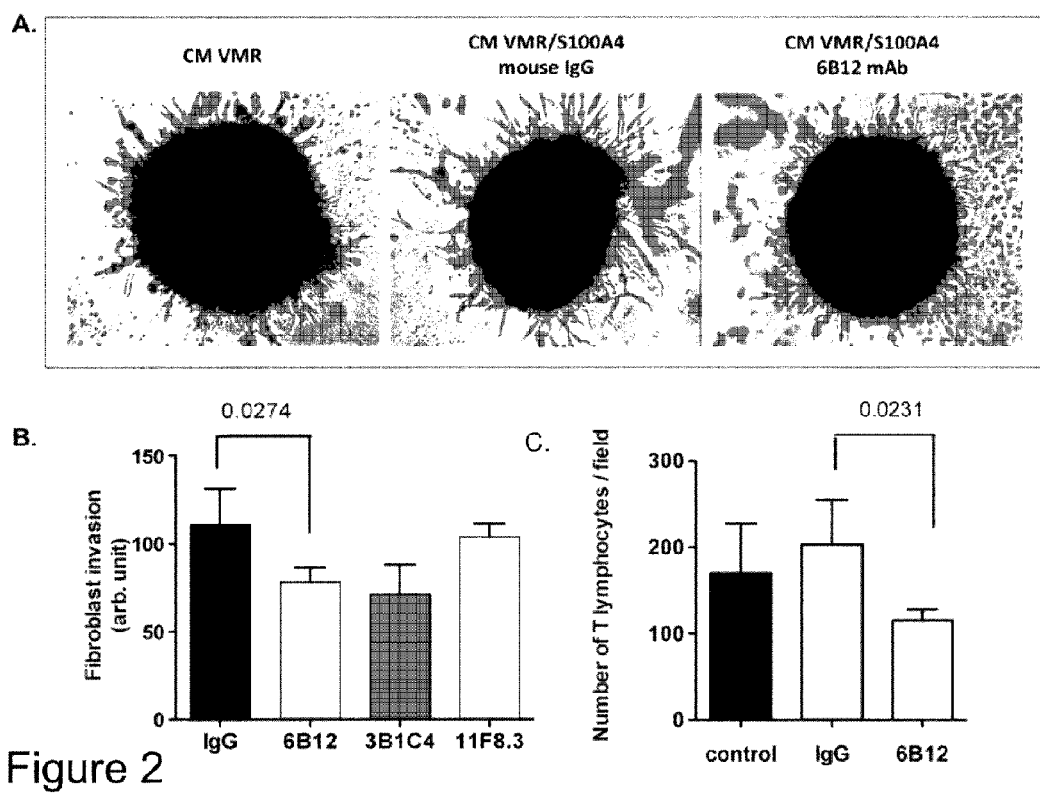
FIG. 2. In vitro blocking activity of the 6B12 mAb. (A) Representative phase-contrast images of fibroblasts invading the matrigel in response to conditioned media (CM) from VMR mouse adenocarcinoma cells alone, after addition of S100A4 (1 μg/mL) or in the presence of S100A4 neutralizing mAb 6B12 (8 μg/mL), 48 h incubation. (B) The 6B12 mAb inhibits significantly the invasion of fibroblasts under 3D culture conditions (unpaired t test, P=0.0274). (C) S100A4 stimulated the attraction of T lymphocytes to the fibroblast monolayer (control), which is inhibited in the presence of the neutralizing S100A4-specific mAb 6B12, in contrast, the mouse IgG control did no display inhibiting function (unpaired t test, P=0.0231).

In this work, S100A4 specific antibodies were raised by immunizing mice using the recombinant mouse S100A4 protein. After screening of a panel of anti-S100A4 monoclonal antibodies, the 6B12 mAb was chosen for in vivo analysis based on its high affinity, specificity (FIGS. 1A-D) and its potency to inhibit S100A4 activity in vitro. The activity of the antibody molecules of the present invention has also been shown by a 3D Matrigel cell culture system, where S100A4 protein is known to stimulate cell invasion as described in Schmidt-Hansen et al. (Schmidt-Hansen et al., 2004b), and by a T cell invasion assay, where S100A4 is know to stimulate T cell infiltration into a fibroblasts monolayer as described in Grum-Schwensen et al. (Grum-Schwensen et al., 2010). These assays may be used to determine whether other antibody molecules according to the present invention have biological activities that correspond to those observed for MAb 6B12. In the examples, the 3D Matrigel matrix assay showed a significant inhibition of S100A4 activity by the 6B12 mAb (FIGS. 2A and B). A similar inhibitory effect was observed in the 2D invasion assay, where the mAb reduces S100A4 ability to stimulate T lymphocyte to infiltrate into a fibroblast monolayer (FIG. 2C).

Figure 3:
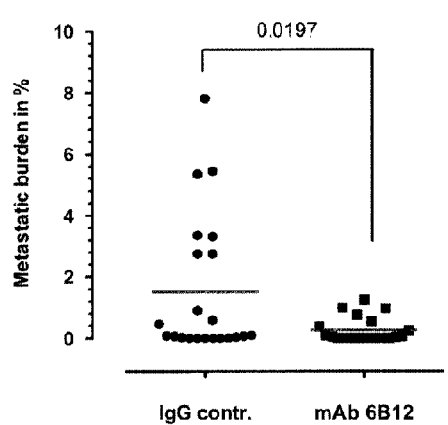
FIG. 3. Anti-S100A4 mAb 6B12 suppresses metastasis and inhibits T lymphocytes attraction to the tumour site. (A) Testing the in vivo effect of the 6B12 mAb in a spontaneous metastasis model based on the subcutaneous (s.c.) injection of highly metastatic CSML100 cells. From the time of s.c. implanting of tumour cells ($1\times10^6$), the mice were treated 3 times a week by intraperitoneally (i.p.) injected of 6B12 mAb (7.5 mg/kg) or IgG (7.5 mg/kg) as a control. After 33 days animals were sacrificed and the metastatic burden in the lungs was analyzed. The statistic of the experiment is summarized in the table. The tumour growth was not affected by the 6B12 antibody treatment. The tumour volume was calculated according following formula [(width)2×length]/2. The amount of metastatic free animals in the 6B12 treated group was increased compared to the control group, 45% to 19.1% respectively. (B) When compared with the control group mice treated with antibody 6B12 mAb demonstrated significantly reduced metastatic burden in the lung (unpaired t-test P=0.0197). (C) The mAb 6B12 inhibits the attraction of T lymphocytes to the tumour sites. The 6B12 mAb treated group display significantly reduced T-cell infiltration of tumour compared to the IgG treated control group (P=0.0003) N=5 per group, 10 fields per tumour were analyzed.
Figure 3:
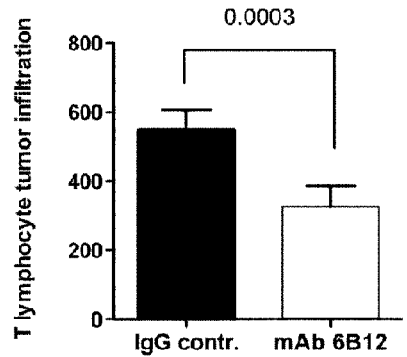

Epitope mapping analyses by screening of non-overlapping 10- to 12-mer peptide sequences of the entire human S100A4 protein, indicates that the 6B12 mAb binds to the S100A4 target protein binding site (FIG. 3A), which is getting exposed after calcium binding. Furthermore, this region is also involved in the formation of tetramers from two dimeric S100A4 units, hence playing an important role in self-aggregation into oligomeric structures. Importantly, the 6B12 mAb is able to recognize "native" conformation of S100A4 as it was shown by competitive immunoprecipitation assay (FIG. 3B). The mAb 6B12 pulls down S100A4 in solution, which was compromised in the presence of peptide 8.

Unless stated otherwise, antibody residues are numbered herein in accordance with the Kabat numbering scheme and CDRs are identified using Kabat rules. The skilled person will be aware that other numbering schemes and CDR definitions are known, in particular the Chothia definition and the AbM definition, see www.biochem.ucl.ac.uk/~martin/abs/GeneralInfo.html, and that applying these definitions may lead to minor changes in the extent of the CDRs. However, using the different definitions the skilled person can readily determine where the CDRs are located in SEQ ID NO: 7 and 9.

Preferably, the antibody molecules of the present invention are capable of binding to S100A4 polypeptides that comprise a polypeptide having at least 80% sequence identity to amino acids 1 to 101 as set out in SEQ ID NO: 11 or 12, or a fragment thereof. Preferred binding characteristics of the antibody molecules of the present invention are discussed further below.

In some embodiments, the antibody molecules of the present invention comprise one or more of the following CDR sequences:
  (a) a CDR-H1 having the amino acid sequence of SEQ ID NO: 1, or the amino acid sequence of SEQ ID NO: 1 with one or more amino acid substitutions, deletions or insertions; and/or
  (b) a CDR-H2 having the amino acid sequence of SEQ ID NO: 2, or the amino acid sequence of SEQ ID NO: 2 with one or more amino acid substitutions, deletions or insertions; and/or (c) a CDR-H3 having the amino acid sequence of SEQ ID NO: 3, or the amino acid sequence of SEQ ID NO: 3 with one or more amino acid substitutions, deletions or insertions; and/or (d) a CDR-L1 having the amino acid sequence of SEQ ID NO: 4, or the sequences of SEQ ID NO: 4, with one or more amino acid substitutions, deletions or insertions; and/or (e) a CDR-L2 having the amino acid sequence of SEQ ID NO: 5, or the sequences of SEQ ID NO: 5, with one or more amino acid substitutions, deletions or insertions; and/or (f) a CDR-L3 having the amino acid sequence of SEQ ID NO: 6, or the sequences of SEQ ID NO: 6, with one or more amino acid substitutions, deletions or insertions.

The antibody molecule of the present invention can tolerate a number of amino acid alterations to the sequences of the CDRs, while retaining the properties of the parent antibody. By way of example, the amino acid sequences of the CDRs of the antibody molecule may each comprise 1, 2, 3, 4, 5, 6, 7, 8, 9 or 10 amino acid substitutions, deletions or insertions as compared to any one of SEQ ID NOs: 1 to 6.

As is well known in the art, the CDRs may be present in a range of different antibody types or framework regions, optionally involving one or more further sequence alterations to ensure retention of a useful property of the antibody as disclosed herein.

Each of the VH and VL domains typically comprise three complementarity determining regions (CDRs) responsible for antigen binding, interspersed by framework regions. In an exemplified embodiment, the present invention provides antibody molecules which comprise a VH domain comprising a CDR-H1, CDR-H2 and CDR-H3 having the sequences of SEQ ID NOs 1, 2 and 3, respectively, and/or a VL domain comprising a CDR-L1, CDR-L2 and CDR-L3 having the sequences of SEQ ID NOs 4, 5 and 6, respectively.

Preferably, the antibody molecules comprise a VH domain having at least 80%, more preferably at least 90%, and still more preferably at least 95% amino acid sequence identity to the amino acid sequence of SEQ ID NO: 7 and/or a VL domain having at least 80%, more preferably at least 90%, and still more preferably at least 95% amino acid sequence identity to having the amino acid sequence of SEQ ID NO: 9.

The present invention also provides an antibody molecule in an IgG format that comprises the heavy and light chain CDRs having the amino acid sequences as set out in SEQ ID NO: 1 to 6.

The present invention also provides an antibody molecule in a Fab format that comprises the heavy and light chain CDRs having the amino acid sequences as set out in SEQ ID NO: 1 to 6.

Generally, the present invention relates to antibody molecules that are capable of inhibiting a biological activity of S100A4, most notably in inhibiting the biological activity of S100A4 in promoting tumour progression and/or in inducing tumour metastasis. Preferably the antibody molecules of the present invention are neutralizing antibodies that are capable of substantially completely inhibiting one or more biological activities of S100A4. Further experiments below indicate that the antibody molecules of the present invention are capable of delaying and/or inhibiting tumour development and growth.

The biological activities of S100A4 polypeptide that may be inhibited by the antibody molecules of the present invention include inhibiting T-cell recruitment mediated by S100A4 and/or inhibiting the biological activity of S100A4 protein in stimulating cell invasion, for example as may be determined in a 3D Matrigel matrix assay or a T cell invasion assay where S100A4 stimulates T cell infiltration into a fibroblasts monolayer. The determination of inhibition of tumour metastasis may be determined in an in vivo mouse xenograft model as exemplified in the experimental examples. Exemplary conditions for carrying out in vitro or in vivo assays are provided in the examples below.

The examples show that the antibody molecules of the present invention are capable of binding to peptide 7 of S100A4 having the amino acid sequence RDNEVDFQEYCV (SEQ ID NO: 13) and/or peptide 8 of S100A4 having the amino acid sequence FLSCIAMMCNEF (SEQ ID NO: 14). As explained below, these findings were then used to generate an epitope to which the antibody molecules of the present invention are capable of binding as represented by $_{66}$R-N- - - - Q- - -V- - -CI- -MM-NEF$_{89}$ (SEQ ID NO: 15), wherein a dash indicates amino acids which are not at the same planar level or are hidden within the structure of the native S100A4 protein.

The sequences of the peptides and the epitope are common to both human and murine S100A4, explaining why the antibody molecules of the present invention are capable of binding to both polypeptides. It is also preferred that the antibody molecules of the present invention are capable of binding to native conformation S100A4 protein. The affinity preference of the antibody molecules may be determined in competition experiments well known to those skilled in the art.

Binding kinetics and affinity (expressed as the equilibrium dissociation constant Kd) of the anti-S100A4 antibody molecules may be determined using standard techniques, such as surface plasmon resonance e.g. using BIAcore analysis. An example of this use of BIAcore analysis is provided in the examples below.

Anti-S100A4 antibody molecules may have a dissociation constant for S100A4 of less than 50 nM, less than 40 nM, less than 30 nM, less than 20 nM, less than 10 nM, or less than 1 nM. For example, an antibody molecule may have an affinity for S100A4 of 1 to 20 nM, e.g. 9 to 15 nM. Preferably antibody molecules of the present invention have affinity constants ($K_D$) of less than 10 nM, more preferably less than 5 nM, more preferably less than 2 nM, and most preferably less than 1 nM. The affinity constants for binding to S100A4 polypeptides can be determined using techniques well known in the art such as Biacore SPR analysis as exemplified in the experimental examples below. In experiments reported below the anti-S100A4 antibody 6B12 was found to have a $K_D$ of 0.114 nM.

Anti-S100A4 antibody molecules may include any polypeptide or protein comprising an antibody antigen-binding site, including Fab, Fab2, Fab3, scFvs, diabodies, triabodies, tetrabodies, minibodies and single-domain antibodies, as well as whole antibodies of any isotype or sub-class. Antibody molecules and methods for their construction and use are described, in for example Holliger & Hudson, Nature Biotechnology 23(9): 1126-1136 (2005).

In some preferred embodiments, the anti-S100A4 antibody molecule may be a whole antibody. For example an IgG, IgA, IgE or IgM or any of the isotype sub-classes, particularly IgG1, and more particularly IgG1K. The anti-S100A4 antibody molecules may be monoclonal antibodies. Anti-S100A4 antibody molecules may be chimeric, humanised or human antibodies the production of which is well known in the art and generally involve using the CDR sequences of a parent antibody to design the variant antibody. In the course of these processes, the antibodies may undergo affinity maturation and/or stability maturation processes that may result in the one or more of the CDR sequences disclosed in the present application comprising 1, 2, 3, 4, 5, 6, 7, 8, 9 or amino acid substitutions, deletions or insertions as compared to any one of SEQ ID NOs: 1 to 6. However, the aim of these processes is to retain one or more of the biological properties of the parent S100A4 antibody, while introducing other useful properties such as reduced immunogenicity, increased stability or half-life or, in the case of bispecific antibodies, the ability of binding an additional target.

Accordingly, in a further aspect, the present invention provides a method of humanising an antibody as described herein. In further embodiments, the antibody molecules may be "humaneered", a process that identifies the minimum sequence information required to determine antigen-binding specificity from the variable region of a reference antibody. This information is then transferred to a library of human, partial V-region gene sequences that are generally close to germline or completely germline, to generate an epitope-focused library of human antibody V regions. The library is then expressed as antibody Fab fragments and screened for antigen-binding Fabs. Positive clones are further characterized to identify those exhibiting the desired characteristics (Kd and/or Ka, expression level, closeness to germline, low aggregation, etc.). The resultant engineered human Fabs retain the binding specificity of the reference antibody. These Fabs typically have an affinity for the antigen that is equivalent or higher than that of the reference antibody, and have V-germline sequences with a high degree of sequence identity compared with human germ-line antibody genes. The minimum specificity determinant (MSD) used to generate the epitope-focused library is generally represented by a short sequence within a CDR of the heavy chain (usually the CDRH3) and a short sequence within a CDR of the light chain (frequently CDRL3). Maturational changes may be introduced in the CDR3 regions of each chain during the library construction to identify antibodies with optimal binding kinetics. The resulting humaneered antibodies have V-segment sequences derived from the human libraries, retain the short MSD sequence from within the relevant CDR regions and have human germ-line Framework 4 regions.

Anti-S100A4 antibody molecules as described herein may be isolated, in the sense of being free from contaminants, such as antibodies able to bind other polypeptides and/or serum components. Monoclonal antibodies are preferred for most purposes, though polyclonal antibodies may also be employed.

Methods of producing anti-S100A4 antibody molecules include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces. The library may be naive, that is constructed from sequences obtained from an organism which has not been immunised with any of the proteins (or fragments), or may be one constructed using sequences obtained from an organism which has been exposed to the antigen of interest.

In the present invention, the method described in the examples may be employed to screen for further examples of anti-S100A4 antibodies having antagonistic properties. After production and/or isolation, the biological activity of an anti-S100A4 antibody molecule may be tested. For example, the ability of the antibody molecule to inhibit the cleavage of a S100A4 substrate may be determined.

Antibody molecules normally comprise an antigen binding domain comprising an immunoglobulin heavy chain variable domain (VH) and an immunoglobulin light chain variable domain (VL), although antigen binding domains comprising only a heavy chain variable domain (VH) are also possible (e.g. camelid or shark antibodies). Such antibodies are included within the scope of the present invention.

Competition between antibody molecules may be assayed easily in vitro, for example using ELISA and/or by tagging a specific reporter molecule to one antibody molecule which can be detected in the presence of one or more other untagged antibody molecules, to enable identification of antibody molecules which bind the same epitope or an overlapping epitope. Such methods are readily known to one of ordinary skill in the art.

The present invention also provides nucleic acid molecules encoding the antibody molecules of the present invention. The nucleic acid molecules are useful for expressing the anti-S100A4 antibody molecules, for example by incorporating the nucleic acid sequences into an expression vector having control sequences operably linked to the nucleic acid encoding the anti-S100A4 antibody molecule to control its expression. The vectors may include other sequences such as promoters or enhancers to drive the expression of the inserted nucleic acid, nucleic acid sequences so that the anti-S100A4 antibody molecule is produced as a fusion and/or nucleic acid encoding secretion signals so that the polypeptide produced in the host cell is secreted from the cell. Suitable vectors can be chosen or constructed, containing appropriate regulatory sequences, including promoter sequences, terminator fragments, polyadenylation sequences, enhancer sequences, marker genes and other sequences as appropriate. Vectors may be plasmids or viral, e.g. 'phage, or phagemid, as appropriate. For further details see, for example, Molecular Cloning: a Laboratory Manual: 2nd edition, Sambrook et al., 1989, Cold Spring Harbour Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Anti-S100A4 antibody molecules can be obtained by transforming the vectors into host cells in which the vector is functional, culturing the host cells so that the anti-S100A4 antibody molecule is produced and recovering the anti-S100A4 antibody molecule from the host cells or the surrounding medium. Prokaryotic and eukaryotic cells are used for this purpose in the art, including strains of E. coli, insect cells (e.g. transformed with baculovirus), yeast, and eukaryotic cells such as COS or CHO cells. The choice of host cell can be used to control the properties of the anti-S100A4 antibody molecule expressed in those cells, e.g. controlling where the polypeptide is deposited in the host cells or affecting properties such as its glycosylation and phosphorylation. If the polypeptide is expressed coupled to an appropriate signal leader peptide it may be secreted from the cell into the culture medium. Following production by expression, the antibody molecule of the present invention may be isolated and/or purified from the host cell and/or culture medium, as the case may be, and subsequently used as desired, e.g. in the formulation of a composition which may include one or more additional components such as a carrier as described elsewhere in the present application.

Accordingly, in further aspects, the present invention provides nucleic acid encoding an anti-S100A4 antibody molecule of the present invention, an expression vector comprising the nucleic acid encoding an anti-S100A4 antibody molecule, operably linked to control sequences to direct its expression, and host cells transformed with this expression vector. In a still further aspect, the present invention provides a method of producing an anti-S100A4 antibody molecule of the present invention, the method comprising culturing the host cells and isolating the anti-S100A4 antibody molecule thus produced.

Derivatising Antibody Molecules

The antibody molecules of the present invention may also be derivatised to modify their properties, and in particular their pharmacological properties. An example is the conjugation of antibody molecules to polyalkylene glycol molecules, in particular polyethylene glycol (PEG) molecules, that may be used to enhance the half life or other pharmacological properties of polypeptide therapeutics. Pegylation is a known strategy for modifying the properties of therapeutic polypeptides, such as peptides, proteins and antibodies. In general, the attachment of PEG molecules to polypeptides is used to alter their conformation, electrostatic or hydrophobic properties, and lead to improvements in their biological and pharmacological properties, such as increasing drug solubility, reducing dosage frequency, modulating (especially increasing) circulating half-life, increasing drug stability and increasing resistance to proteolytic degradation. Pegylation works by increasing the molecular weight of the therapeutic polypeptide by conjugating the polypeptide to one or more PEG polymer molecules. This is particularly applicable to types of antibody molecules that are fragments of complete antibodies such as Fab fragments. In other embodiments of the present invention polyalkylene glycol is used as a linker group for conjugating antibody molecules of the present invention to nanoparticles such as gold nanorods or gold nanoparticles.

This may be carried out to the antibody molecules of the present invention by reacting suitable functional groups present in the antibody molecules with reactive polyalkylene glycol molecules. Depending on the functional groups available in the antibody molecules of the present invention, it may be possible to pegylate the antibody molecules in a selective way, for example by identifying suitable reactive cysteine residues in the antibody molecules. Polyalkylene glycol molecules are interchangeably referred to in the art as polyalkylene oxide molecules and are polyethers. Polyalkylene glycol molecules may have linear, branched, comb or star structures and generally are highly water soluble. In addition, the basic poly(alkylene glycol) structure may be provided with one or more reactive functional groups such as hydroxy, amine, carboxylic acid, alkyl halide or thiol groups to facilitate the reaction of the poly(alkylene glycol) molecule with other species such as polypeptides. Preferred polyalkylene glycol molecules include those substituted at one or more hydroxyl positions with a chemical group, such as an alkyl group having between one and four carbon atoms. Preferred polyalkylene glycol molecules for use in accordance with the present invention are polyethylene glycol ("PEG") molecules, although the skilled person would be able to derivatise antibody molecules of the present invention using other polyalkylene glycol molecules, such as polypropylene glycol or polyethylene-polypropylene glycol copolymers. Polyalkylene glycol molecules, including PEGs, typically have molecular weights between about 400 Da and about 80 kDa, more preferably between about 1 kDa and about 60 kDa, and more preferably between about 5 kDa and about 50 kDa, e.g. molecular weights of 10 kDa, 20 kDa, 30 kDa or 40 kDa. Polyalkylene glycol molecules that may be used in accordance with the present invention are well known in the art and publicly available, for example from commercially available sources such as SigmaAldrich.

Imaging Applications

The antibody molecules of the present invention may additionally be labelled to enable them to be employed for imaging, either in conjunction with or independent of their therapeutic uses. Techniques for labelling antibodies are well known in the art that enable the antibodies to be used in a range of imaging and spectroscopic applications. This might be useful in a number of different medical or research applications, for example in the fields of oncology for diagnosing cancer or determining the progression of cancer and/or metastatic cancer.

One particular example of the use of the antibody molecules for imaging involves the use of radionuclide labels in nuclear medicine imaging techniques, such as Single Photon Emission Computed Tomography (SPECT), an imaging technique that detects gamma rays emitted from a radionuclide to produce a two dimensional image of the distribution of the radionuclide in a sample or subject, and Positron Emission Tomography (PET), an imaging technique that three-dimensional images by detecting pairs of gamma rays emitted indirectly by a positron-emitting radionuclide introduced into a sample or subject. Antibody molecules having radionuclide labels may also be employed for multi-modal studies in which imaging techniques are combined, either by selecting radionuclides that are active in more than one imaging technique or by labelling the antibody molecules with more than one type of label.

The antibody molecules of the present invention may be labelled with a radionuclide, for example a radionuclide provided as a complex, or conjugated to a second molecule, such as a linker, that is can be associated with the label. Examples of radionuclides for use in imaging techniques or therapy include technetium, rhenium, copper, cobalt, gallium and indium isotopes such as Tc-99m, Re-186, Re-188, Co-57, Ga-67, In-111 (SPECT), Cu-64, Cu-60, Cu-61, Cu-62, Cu-67, Tc-94m, Ga-68, Co-55 (PET). In general, technetium isotopes are employed for imaging purposes, rhenium isotopes for therapeutic purposes and copper isotopes for both imaging and therapy.

Diagnostic Applications

The antibody molecules of the present invention also find application in the area of diagnostics as they are capable of specifically binding to S100A4 polypeptide. In some applications, the antibody molecules of the present invention are capable of specifically binding to functional forms of S100A4 protein. Accordingly, the present invention includes a method for the diagnosis and/or prognosis of a S100A4 related condition that uses one or more anti-S100A4 antibody molecules of the present invention. Generally, "a S100A4 related condition" includes conditions characterised by diseased cells which express the S100A4, or which express it at an elevated level as compared to normal cells, and/or which is a disease mediated by the S100A4 polypeptide.

A range of techniques are known in the art for determining whether S100A4 polypeptide is present in a sample obtained from an individual. These techniques may be employed by the skilled person for use in accordance with the present invention. In general, the purpose of carrying of the methods disclosed herein on a sample from an individual is to determine whether the individual has a S100A4 related condition, that is a condition characterised by diseased cells which express S100A4 polypeptide and/or which is a disease mediated by S100A4 polypeptide. As explained above, S100A4 has been shown to be upregulated in many cancers and elevated expression correlated in some cancers with a more aggressive phenotype and poor clinical outcome. In particular, the expression of S100A4 has been shown to be a prognostic marker for various cancers as S100A4 has been shown to be upregulated in many cancers and elevated expression of S100A4 has been correlated in some cancers with a more aggressive phenotype and poor clinical outcome. Thus, the anti-S100A4 antibody molecules of the present invention find utility in methods and assays that use S100A4 as a diagnostic and/or prognostic marker for various cancers, such as gastric cancer, pancreatic cancer, colorectal cancer, thyroid cancer, breast cancer, squamous cell carcinoma, non-small cell lung cancer, prostate cancer, lung cancer, head and neck cancer, brain cancer (including glioblastoma multiforme), renal cell carcinoma (including clear cell renal carcinoma), melanoma, lymphoma, plasmocytoma, sarcoma, glioma, thymoma, leukemia, colon cancer, esophageal cancer, ovary cancer, cervical cancer and hepatoma.

In addition, S100A4 may be involved in other conditions, notably inflammatory diseases, such as rheumatoid arthritis, psoriasis and inflammatory myopathies, and the antibody molecules of the present invention may be useful for their diagnosis and/or prognosis. These conditions are therefore also S100A4 related conditions as used herein.

Accordingly, in a further aspect, the present invention comprises a method for diagnosis or prognosis of a S100A4 related condition in an individual, the method comprising contacting a sample from the individual with an anti-S100A4 antibody molecule of the present invention which is capable of binding to S100A4 polypeptide present in the sample and determining the presence and/or amount of the complex formed between the antibody molecule and the S100A4 polypeptide. The purpose of such analysis may be used for diagnosis or prognosis, e.g. to serve to detect the presence of an existing cancer, to help identify the type of cancer, to assist a physician in determining the severity or likely course of the cancer and/or to optimise treatment of it. The methods make use of biological samples from individuals that may contain S100A4 polypeptide. Examples of biological samples include blood, plasma, serum, tissue samples and saliva. Examples of potential diagnostic applications and assay formats are described in the inventor's earlier patent applications U.S. Pat. No. 6,638,504 which may be put into practice using the antibody molecules of the present invention.

Specific diagnostic applications of the present invention include methods of determining a concentration of S100A4 polypeptide in a sample from an individual, the method using an anti-S100A4 antibody molecule in a sandwich ELISA format. Conveniently, the sample may be a blood sample. One application of this assay would be in the testing of samples from breast cancer patients which are receiving HERCEPTIN® (trastuzumab) treatment, for example for assisting in the prognosis of their condition and/or for determining the likelihood or occurrence of metastasis.

Additionally or alternatively, the assay methods of the present invention may be used in the diagnosis or prognosis of individuals undergoing treatment for a cancer that correlates with a change in the expression and/or secretion of S100A4 polypeptide when the treatment is therapeutically effective. This in turns means that the method may be used for assisting in the prognosis of their condition and/or for determining the likelihood or occurrence of metastasis. Typically, the cancer will be characterised by a reduction in the expression and/or secretion of S100A4 polypeptide when treatment is therapeutically effective, thereby enabling individuals to be identified who are unlikely to respond to therapy or for whom the therapeutic effectiveness of the treatment is reduced or has become ineffective.

By way of illustration, studies of EGFR/S100A4 interplay in breast cancer of HERCEPTIN® treated patients. As activation of HER-2 enhances the expression and secretion of S100A4, one effect on blocking HER-2 with HERCEPTIN® is that it is likely to reduce the amount of the S100A4 polypeptide in the plasma of breast cancer patients. This therapeutic effect might be beneficial for the cancer patients because it inhibits S100A4 driven pro-metastatic cascades. Since not all patients with a HER-2-positive breast cancer respond to HERCEPTIN® therapy and because many who initially respond eventually develop resistance, the levels of S100A4 polypeptide may be used as an indicator of the treatment efficiency. This approach may be validated by analysing the level of S100A4 in plasma samples from different breast cancer patients before and after treatment with HERCEPTIN® and comparing these levels from patients treated with conventional chemo- and/or radiotherapy.

The antibody molecules of the present invention may also be used in assays that determine the levels of different forms of S100A4 polypeptide as described by the some of the present inventors in Abdali et al. (J. Phys, Chem. C, 114: 7274-7279, 2010). This approach is based on the ability to distinguish in vitro between the dimeric and the multimeric form of S100A4 polypeptide. On convenient method is to use Surface Enhanced Raman Spectroscopy (SERS) as the method is very sensitive and may be applied for screening of a sample (e.g. a blood sample) from an individual to determine a status about dimeric/multimeric forms of S100A4 present in the sample. The status may be used to predict the likelihood of the individual developing malignant cancer and/or metastasis. However, for screening samples such as blood samples blood, SERS needs to be coupled to a method which can capture the different forms of S100A4 polypeptide, as is made possible using the anti-S100A4 molecules of the present invention which are effective capture antibodies as they are capable of recognizing functional S100A4 protein.

More generally, there are various methods for determining the presence or absence in a test sample of S100A4 polypeptide. For example, a sample may be tested for the presence of a binding partner for a specific binding member such as an antibody (or mixture of antibodies), specific for S100A4 or a particular variant of it.

In such cases, the sample may be tested by being contacted with an antibody molecule of the present invention under appropriate conditions for specific binding, before binding is determined, for instance using a reporter system. Where a panel of antibodies is used, different reporting labels may be employed for each antibody so that binding of each can be determined. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. One favoured mode is by covalent linkage of each antibody with an individual fluorochrome, phosphor or laser dye with spectrally isolated absorption or emission characteristics. Suitable fluorochromes include fluorescein, rhodamine, phycoerythrin and Texas Red. Suitable chromogenic dyes include diaminobenzidine.

Other reporters include macromolecular colloidal particles or particulate material such as latex beads that are coloured, magnetic or paramagnetic, and biologically or chemically active agents that can directly or indirectly cause detectable signals to be visually observed, electronically detected or otherwise recorded. These molecules may be enzymes which catalyse reactions that develop or change colours or cause changes in electrical properties, for example. They may be molecularly excitable, such that electronic transitions between energy states result in characteristic spectral absorptions or emissions. They may include chemical entities used in conjunction with biosensors. Biotin/avidin or biotin/streptavidin and alkaline phosphatase detection systems may be employed.

The use of the anti-S100A4 antibody molecules may be used as part of microarray comprising a panel of binding agents acting as probes for S100A4 polypeptide and optionally one or more other targets. The probes that may be immobilised on the surface with the antibodies of the present invention include proteins, other types of antibodies, small molecule compounds, peptides, and carbohydrates. The samples applied to the microarray may be are complex mixtures of analytes, such as serum, total cell extracts, and whole blood. The key concepts of an array of probes, which undergo selective binding/interaction with a target and which are then interrogated via, for example, a fluorescent, colorimetric or chemiluminescent signal, remain central to the method. A review of ideas on protein and chemical microarrays is given by Xu and Lam in "Protein and Chemical Microarrays-Powerful Tools for Proteomics", J Biomed., 2003(5): 257-266, 2003. This reference also provides the historical sequence in the development of DNA microarrays. A review of patent issues related to early microarrays is given Rouse and Hardiman ("Microarray technology—an intellectual property retrospective", Pharmacogenomics, 4(5): 623-632, 2003).

Accordingly, in a further aspect, the present invention provides a microarray, or the components for forming a microarray (e.g. a bead array), wherein the microarray comprises an anti-S100A4 antibody of the present invention and one or more further binding agents present or locatable on a substrate at a plurality of locations. The microarray will preferably also comprise a plurality of further binding agents for carrying out other tests on the sample, for example to determine the presence of S100A4 polypeptide bound to the array for determining whether an individual has a S100A4 related condition and/or its prognosis.

There is an increasing tendency in the diagnostic field towards miniaturisation of assays, e.g. making use of binding agents (such as antibodies) immobilised in small, discrete locations as arrays on solid supports or on diagnostic chips. The use of microarrays can be particularly valuable as they can provide great sensitivity, particularly through the use of fluorescent labelled reagents, require only very small amounts of biological sample from individuals being tested and allow a variety of separate assays can be carried out simultaneously. Microarrays are libraries of biological or chemical entities immobilised in a grid/array on a solid surface and methods for making and using microarrays are well known in the art. A variation on this theme is immobilisation of these entities onto beads, which are then formed into a grid/array. The entities immobilised in the array can be referred to as probes. These probes interact with targets present in a sample and the extent of interaction is assessed using fluorescent labels, colorimetric/chromogenic labels, radioisotope labels or label-free methods (e.g. scanning Kelvin microscopy, mass spectrometry, surface plasmon resonance, etc.). The interaction may include binding, hybridization, absorption or adsorption. The microarray process provides a combinatorial approach to assessing interactions between probes and targets.

In the spotted microarray approach, binding agents are printed in an array pattern on a solid substrate by either a spotting robot using pins or variations on ink-jet printing methods. The spots are typically in the 30-500 mm size range with separations of the order of 100 mm or more. A lack of uniformity of spot size, variations of spot shape and donut or ring-stain patterns caused during the drying of spots can result in non-uniform immobilisation of the DNA and hence non-uniform fluorescence following the hybridisation.

An alternative method for making arrays employs bead based microarrays. An example of this approach is the system used by Illumina (www.illumina.com) in which probes are immobilised on small (3-5 μm diameter) beads. After hybridisation the beads are cast onto a surface and drawn into wells by surface tension. In the Illumina system, the wells are etched into the ends of optical fibres in fibre bundles. The fluorescence signal is then read for each bead. The method includes a tagging of each bead so that the bioactive agent on each bead can be decoded from the probe position and a decoding system is needed to distinguish the different probes used. The bead based system is described in U.S. Pat. Nos. 6,023,540, 6,327,410, 6,266,459, 6,620,584 and 7,033,754.

In a further aspect, the present invention provides kits for carrying out the methods disclosed herein. The components of the kit will be dependent on the format of assay and will include anti-S100A4 antibodies of the present invention. Generally, the components of the kit will be provided in a suitable form or package to protect the contents from the external environment. The kit may also include instructions for its use and to assist in the interpretation of the results of the test. The kit may also comprise sampling means for use in obtaining a test sample from an individual, e.g. a swab for removing cells from the buccal cavity or a syringe for removing a blood sample (such components generally being sterile). In one embodiment, the kit may comprise a microarray as described above, optionally in combination with other reagents, such as labelled developing reagents, useful for carrying out testing with the assay.

Medical Uses

The antibody molecules of the present invention are useful for the treatment of S100A4 related conditions, notably in the treatment of cancer and other types of conditions including inflammatory diseases, such as rheumatoid arthritis, psoriasis and inflammatory myopathies. See, for example, psoriasis (Zibert et al., J. Invest Dermatol. 130(1):150-60. Significance of the S100A4 protein in psoriasis. www.ncbi.nlm.nih.gov/pubmed/19641515), rheumatoid arthritis (Rheumatology (Oxford). 2009; 48(12):1590-4.

Metastasis-inducing S100A4 protein is associated with the disease activity of rheumatoid arthritis. Oslejsková L et al., www.ncbi.nlm.nih.gov/pubmed/19828600) and a general review (Grigorian et al., Curr Mol Med. 2008 September; 8(6):492-6. Metastasis-inducing S100A4 protein: implication in non-malignant human pathologies. www.ncbi.nlm.nih.gov/pubmed/18781956). While not wishing to be bound by any specific theory, the present inventors believe that the antibody molecules can treat inflammatory diseases.

Inflammatory myopathy is a form of myopathy that involves inflammation of the muscle. Inflammatory myopathy is generally synonymous to the term dermatopolymyositis, which is generally accepted to includes polymyositis, dermatomyositis, and inclusion-body myositis (see 10th revision of the International Statistical Classification of Diseases and Related Health Problems (ICD). The involvement of S100A4 in inflammatory myopathies was published in Cerezo L. et. al. The metastasis promoting protein S100A4 is increased in idiopathic inflammatory myopathies. Rheumatology, 50: 1766-1772, 2011.

As described above S100A4 has been linked to poor patient outcome in a number of different types of cancer, and in particular metastatic cancer. By way of example, (i) nuclear expression of S100A4 is a prognostic marker in TNM stage II colorectal cancer (Eur J Cancer 46: 2919-2925); (ii) high expression of S100A4 in Clear Cell RCC is associated with worse 5 year overall survival (The Journal of International Medical Research 2012; 40: 475-485); (iii) S100A4 correlates with tumour grade in prostate cancer (Journal of Clinical Oncology, Vol 21, No 1 (January), 2003: pages 106-112); (iv) over expression of S100A4 was significantly correlated with poor prognosis and S100A4-positive pancreatic cancers were associated with postoperative liver metastasis. This means that the antibody molecules of the present invention may be used for the treatment of including gastric cancer, pancreatic cancer, colorectal cancer, thyroid cancer, breast cancer, squamous cell carcinoma, non-small cell lung cancer, prostate cancer, lung cancer, head and neck cancer, brain cancer (including glioblastoma multiforme), renal cell carcinoma (including clear cell renal carcinoma and hepatocarcinoma), melanoma, lymphoma, plasmocytoma, sarcoma, glioma, thymoma, leukaemia, colon cancer, oesophageal cancer, ovary cancer, cervical cancer or hepatoma.

By way of example, Siddique et al. support the role of S100A4 in the development and metastasis of prostate cancer and proposes that the protein would be an excellent candidate to be exploited for therapeutic agents to treat prostate cancer in humans (Genes & Cancer, 4(5-6): 224-234, 2013). Other studies have proposed the utility of antibody-based therapeutic approaches against S100A4 in models of pancreatic cancer (see Hernandez et al., PLoS ONE 8(9): e72480, doi:10.1371/journal.pone.0072480).

As the antibody molecules of the present invention are capable of inhibiting the biological activity of S100A4 in promoting tumour progression and/or in inducing tumour metastasis, they may be administered at any time during the treatment of a patient with cancer, and may be given prophylactically, for example to reduce the risk of metastasis occurring by administration early in the course of treatment or as a treatment of metastasis later in the course a patient's disease.

As described above S100A4 has been linked to a role in the maintenance of cancer initiating cells (or cancer stem cells). This means that the antibody molecules of the present invention may also be used to target and eliminate such cancer stem cells, and also be used for the treatment of cancers which are enriched for cancer stem cells.

In some embodiments, the antibody molecules of the present invention may be administered in conjunction with a chemotherapeutic agent or in conjunction with radiotherapy or in conjunction with anti-cancer therapeutic antibodies or in conjunction with an anti-cancer therapeutic agent, in particular chemotherapeutic agents or anti-cancer therapeutic agents which inhibit the proliferation of cancer cells. Examples of additional anti-cancer therapeutic agents include an EGFR pathway inhibitor, such as an anti-EGFR antibody or an EGFR kinase inhibitor, such as cetuximab, panitumumab, Iressa (gefitinib or (N-(3-chloro-4-fluorophenyl)-7-methoxy-6-(3-morpholin-4-ylpropoxy)quinazolin-4-amine), or Tarceva (erlitonib or N-(3-ethynylphenyl)-6,7-bis(2-methoxyethoxy) quinazolin-4-amine), or other agents such as Herceptin™ (trastuzumab). Further examples of chemotherapeutic agents include alkylating agents, such as cisplatin, carboplatin and oxaliplatin, anthracyclines, plant alkaloids such as taxanes and vinca alkaloids, and topoisomerase inhibitors such as irinotecan, topotecan, amsacrine, etoposide, etoposide phosphate and teniposide, or fluorouracil (5FU). Recently, niclosamide, an antihelmintic drug was established as anti-S100A4 directed drug candidate to fight metastatic colon tumours (Sack et al., 2011).

In a further possibility, the antibody molecules of the present invention may be antibody-drug conjugates in which the antibody molecule is linked to a drug or a toxin or a nanoparticle. This may be done to direct the drug or toxin to a target site in a biological system where S100A4 is present. This approach may entail engineering the antibody molecule to provide a functional group capable of reacting with the drug or toxin, or alternatively providing the antibody molecule with a linker group that is capable of reacting with the drug or toxin. In this aspect of the present invention, the drug may also be a pro-drug for conversion to active drug at a target site in a patient. By way of example, antibodies of the present invention may be linked to nanoparticles for delivering other agents linked to or associated with the nanoparticles or, where the nanoparticles are gold nanoparticles (or gold rods) for use in thermal ablation therapy, or as a carrier for the antibody to enhance the persistence time in the body and the accumulation to the tumour site. A high local concentration, by coupling several antibodies of the present invention to the surface of a nanoparticle could also enhance the efficiency of the antibody therapy.

Photothermal Therapy/Thermal Ablation Therapy

In a further aspect, the antibody molecules of the present invention may be conjugated to gold nanoparticles, such as gold nanorods (GNRs) to provide a novel antibody-targeted anti-cancer therapy in which cancer cells (e.g. tumour and stroma cells) are selectively eradicated by thermal energy. In this approach, anti-S100A4 antibodies of the present invention are coupled to gold nanoparticles, optionally via a linker group, for example using poly(alkylene glycol) linkers as described above. Methods suitable for preparing gold nanorods are described in Nikoobakht & El-Sayed, (Preparation and Growth Mechanism of Gold Nanorods (NRs) Using Seed-Mediated Growth Method, Chemistry of Materials, 2003, 15: 1957-1962, 2003) or Rostro-Kohanloo et al. (The stabilization and targeting of surfactant-synthesized gold nanorods. *Nanotechnology,* 20(43), 434005. doi:10.1088/0957-4484/20/43/434005, 2009). The antibody nanoparticle conjugates may then be administered to an individual with cancer, for example by intravenous injection. As S100A4 protein is highly enriched in the tumour microenvironment, the nanoparticles are directed to the site of the tumour delivery and will become enriched at the tumour site. The site of the tumour can then be exposed to radiation having a wavelength capable of passing through tissue and heating the nanoparticles. Conveniently, the radiation is light in the near-infrared range that is capable of easily passing through tissue, but is absorbed by gold nanoparticles or nanorods and converted into heat. This treatment will thermally destroy the entire tumour without significant damage to surrounding healthy tissue. Advantageously, the therapy will not only kill fast growing tumour cells which are generally targeted by traditional forms of therapy forms, but also slow growing cancer stem cells (CSCs) and stroma cells. This will be particularly beneficial for patients, since these cells actively contribute to metastasis, therapy resistance and recurrence of the cancer.

For cancer therapy different strategies have been employed for instance to kill tumour cells by irradiation or chemotherapeutic agents. Notably, these approaches address mainly fast growing tumour cells, but they are not effectively eliminating cells with low dividing frequencies such as most of the stroma cells and cancer stem cells (CSCs). This is a big drawback of current treatments, since these cells contribute substantially to tumour relapses and therapy resistance, and consequently leads to the failure of the cancer therapy (Malanchi et al., 2012; Valastyan et al., 2011; Al-Hajj et al., 2003; Reya et al., 2005). A more beneficial strategy would be to eliminate stroma and CSC as well to remove the base of the tumour regrowth and progression. To actively guide the GNRs to the tumour site an antibody against the metastasis-promoting S100A4 protein will be used. This protein has been shown to be enriched at the tumour site (Cabezón et al., 2007; Grum-Schwensen et al., 2005). It is upregulated mainly in tumour stroma cells, however, also found significantly upregulated in CSCs of gliomas (Harris et al., 2008) and head and neck CSCs where it has been shown to maintain the stemness properties and tumourigenicity (Lo et al., 2011). The elimination of the tumour stroma, the major source of S100A4 production, and at the same time the inhibiting the pro-metastatic activity of the S100A4 protein, will be an advantage of this therapeutic strategy.

The role of S100A4 in cancer stems cells has been also been proposed, see Yan et al. (Hepatology. 2013 June; 57(6): 2274-86. doi: 10.1002/hep.26257. Epub 2013 May 1). In this study, complementary DNA (cDNA) microarray analysis showed that S100A4 expression was significantly higher in liver cancer-associated mesenchymal stem cells compared with liver normal mesenchymal stem cells from adjacent cancer-free tissues. Importantly, the inhibition of S100A4 led to a reduction of proliferation and invasion of hepatocellular carcinoma cells, while exogenous S100A4 expression in HCC cells resulted in heavier tumors and more metastasis sites. Kanojia et al. (Proteomics, 2012 November; 12(22):3407-15. doi: 10.1002/pmic.201200103. Epub 2012 Oct. 23) demonstrated that HER2 overexpression leads to mammary tumorigenesis and its elevated levels lead to increase in cancer stem cells, invasion, and metastasis. S100A4 has been identified as a protein among the altered protein expression pattern in cancer stem cells as compared to non-cancer stem cells using LC-MS/MS and those results were confirmed using qRT-PCR and Western blotting, supporting, inter alia, a role for S100A4 as a molecular target for the treatment of breast cancer.

In summary, combining the effects of heat-producing GNRs with the metastasis-inhibiting and tumour-targeting function by attaching the S100A4-antibody could enhance the success of the therapy strongly.

To test the efficiency of the therapy we developed a dual reporter system which allow us to follow the effect of the therapy by monitoring the ablation of the tumour and stroma in living animals.

Figure 8:
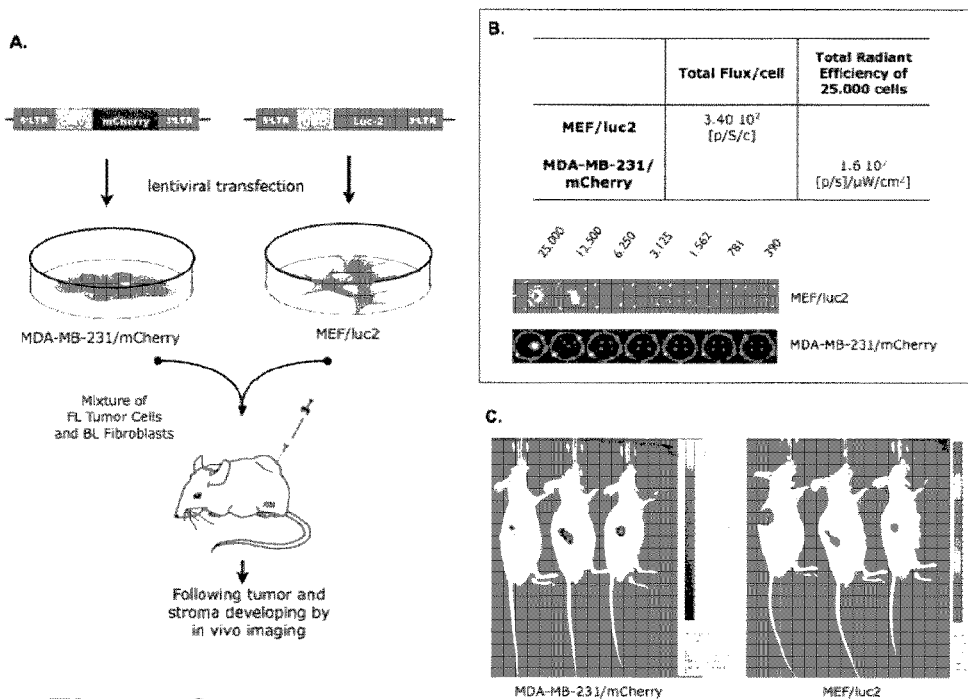
FIG. 8. Dual reporter system for in vivo imaging of mice. (A) Scheme describing the production and use of two reporter cell lines for in vivo imaging. (B) The imaging showing the activity of the reporter in a dilution series of MEF/luc2 cells (upper panel) and MDA-MB-231/mCherry cells (lower panel). The table is summarizing plate quantification result of the activity of MEF/luc2 cells and the total radiant efficiency of the MDA-MB-231/mCherry cells (C) Subcutaneous tumour formed from fluorescent cancer cells (MDA-MB-231/mCherry) and bioluminescent fibroblasts (MEF/luc2) detected by in vivo imaging of mice.
Figure 9:
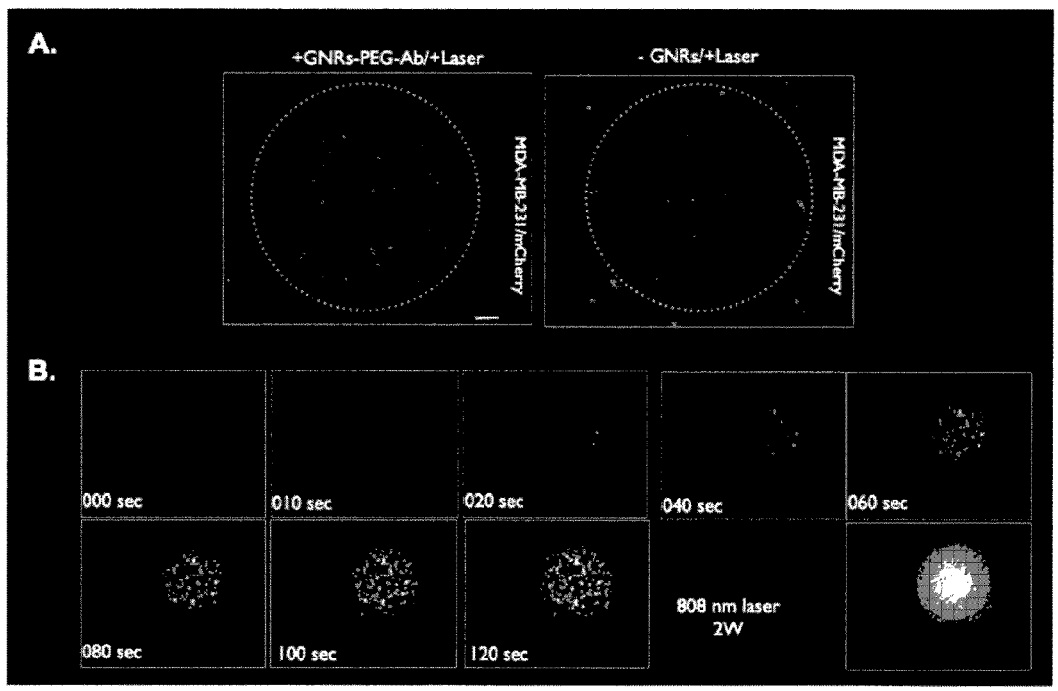
FIG. 9. Antibody-targeting GNRs mediated thermal ablation of tumour cells. (A) Thermal ablation of MDA-MB-231/mCherry cells treated with 6B12 antibody-targeted GNRs (GNRs-PEG-Ab, left panel) resulted in an increase in DAPI stained nuclei after near-infrared laser treatment (8 sec laser/2 sec pause intervals, duration 120 sec, at 2.0 ampere). Right panel: cell without GNRs were not affected by the laser. The circle indicates the laser spot. (B) Time-laps images from the same sample as shown in A (left panel). The last image shows a phase contrast image of the cell after treatment.

Experiments that demonstrate the use of the reporter system are discussed in detail herein with reference to FIGS. 7 to 9.

Pharmaceutical Compositions

The anti-S100A4 antibody molecules of the present invention may be comprised in pharmaceutical compositions with a pharmaceutically acceptable excipient. A pharmaceutically acceptable excipient may be a compound or a combination of compounds entering into a pharmaceutical composition which does not provoke secondary reactions and which allows, for example, facilitation of the administration of the anti-S100A4 antibody molecule, an increase in its lifespan and/or in its efficacy in the body or an increase in its solubility in solution. These pharmaceutically acceptable vehicles are well known and will be adapted by the person skilled in the art as a function of the mode of administration of the anti-S100A4 antibody molecule.

In some embodiments, anti-S100A4 antibody molecules may be provided in a lyophilised form for reconstitution prior to administration. For example, lyophilised antibody molecules may be re-constituted in sterile water and mixed with saline prior to administration to an individual.

Anti-S100A4 antibody molecules will usually be administered in the form of a pharmaceutical composition, which may comprise at least one component in addition to the antibody molecule. Thus pharmaceutical compositions may comprise, in addition to the anti-S100A4 antibody molecule, a pharmaceutically acceptable excipient, carrier, buffer, stabilizer or other materials well known to those skilled in the art. Such materials should be non-toxic and should not interfere with the efficacy of the anti-S100A4 antibody molecule. The precise nature of the carrier or other material will depend on the route of administration, which may be by bolus, infusion, injection or any other suitable route, as discussed below.

For intravenous administration, e.g. by injection, the pharmaceutical composition comprising the anti-S100A4 antibody molecule may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer's Injection, Lactated Ringer's Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

A pharmaceutical composition comprising an anti-S100A4 antibody molecule may be administered alone or in combination with other treatments, either simultaneously or sequentially dependent upon the condition to be treated.

An anti-S100A4 antibody molecule as described herein may be used in a method of treatment of the human or animal body, including prophylactic treatment (e.g. treatment before the onset of a condition in an individual to reduce the risk of the condition occurring in the individual; delay its onset; or reduce its severity after onset). The method of treatment may comprise administering an anti-S100A4 antibody molecule to an individual in need thereof.

Administration is normally in a "therapeutically effective amount", this being sufficient to show benefit to a patient. Such benefit may be at least amelioration of at least one symptom. The actual amount administered, and rate and time-course of administration, will depend on the nature and severity of what is being treated, the particular mammal being treated, the clinical condition of the individual patient, the cause of the disorder, the site of delivery of the composition, the method of administration, the scheduling of administration and other factors known to medical practitioners. Prescription of treatment, e.g. decisions on dosage etc., is within the responsibility of general practitioners and other medical doctors and may depend on the severity of the symptoms and/or progression of a disease being treated. Appropriate doses of antibody molecules are well known in the art (Ledermann J. A. et al. (1991) Int. J. Cancer 47: 659-664; Bagshawe K. D. et al. (1991) Antibody, Immunoconjugates and Radiopharmaceuticals 4: 915-922). Specific dosages may be indicated herein or in the Physician's Desk Reference (2003) as appropriate for the type of medicament being administered may be used. A therapeutically effective amount or suitable dose of an antibody molecule may be determined by comparing its in vitro activity and in vivo activity in an animal model. Methods for extrapolation of effective dosages in mice and other test animals to humans are known. The precise dose will depend upon a number of factors, including whether the antibody is for prevention or for treatment, the size and location of the area to be treated, the precise nature of the antibody (e.g. whole antibody, fragment) and the nature of any detectable label or other molecule attached to the antibody.

A typical antibody dose will be in the range 100 µg to 1 g for systemic applications, and 1 µg to 1 mg for topical applications.

An initial higher loading dose, followed by one or more lower doses, may be administered. Typically, the antibody will be a whole antibody, e.g. the IgG1 or IgG4 isotype. This is a dose for a single treatment of an adult patient, which may be proportionally adjusted for children and infants, and also adjusted for other antibody formats in proportion to molecular weight. Treatments may be repeated at daily, twice-weekly, weekly or monthly intervals, at the discretion of the physician. Treatments may be every two to four weeks for subcutaneous administration and every four to eight weeks for intra-venous administration. Treatment may be periodic, and the period between administrations is about two weeks or more, e.g. about three weeks or more, about four weeks or more, or about once a month. Treatment may be given before, and/or after surgery, and/or may be administered or applied directly at the anatomical site of surgical treatment or invasive procedure. Suitable formulations and routes of administration are described above.

In some preferred embodiments, the therapeutic effect of the anti-S100A4 antibody molecule may persist for several half-lives, depending on the dose. For example, the therapeutic effect of a single dose of anti-S100A4 antibody molecule may persist in an individual for 1 month or more, 2 months or more, 3 months or more, 4 months or more, 5 months or more, or 6 months or more.

Material and Methods
Mice

A/Sn strain of mice was used in all mouse experiments. All animals were maintained according to the Federation of European Laboratory Animal Science Associations guidelines for the care and use of laboratory animals.

Peptides

Nine 10- to 12-mer peptides corresponding to the entire 101 amino acids of human S100A4 protein: #1: MACPLEKALD (10-mer: 1-10; SEQ ID NO: 18), #2: VMVSTFHKYS (10-mer: 11-20; SEQ ID NO: 19), #3: GKEGDKFKLNK (11-mer: 21-31; SEQ ID NO: 20), #4: SELKELLTREL (11-mer: 32-42; SEQ ID NO: 21), #5: PSFLGKRTDEA (11-mer: 43-53; SEQ ID NO: 22), #6: AFQKLMSNLDSN (12-mer: 54-65; SEQ ID NO: 23), #7: RDNEVDFQEYCV (12-mer: 66-77; SEQ ID NO: 13), #8: FLSCIAMMCNEF (12-mer: 78-89; SEQ ID NO: 14), #9: FEGFPDKQPRKK (12-mer: 90-101; SEQ ID NO: 24), were synthesized by solid-phase synthesis (Alpha Diagnostic International, San Antonio, Tex., USA) and used for epitope mapping by ELISA and in inhibition experiments.

Western Blot

To detect S100A4 by specific antibodies, Western blot was performed as described in Klingelhöfer et al. (Klingelhöfer et al., 2009). Mouse monoclonal anti-S100A4 antibodies (3B1C4, 11F8.3 and 6B12) or polyclonal rabbit anti-S100A4 produced by our laboratory, were used as primary antibodies. As secondary antibodies, rabbit anti-mouse HRP conjugated or goat, anti-rabbit-HRP-conjugated antibodies, were used. Both antibodies were obtained from Dako (Glostrup, Denmark).

To detect endogenous S100A4 protein from different cell lines $0.4 \times 10^5$ cells per well were seeded on a six-well tissue culture plate and grown until cells reached confluence under standard tissue culture conditions. Protein extracts were made by lysing cells in 300 µl 1×SDS-gel loading buffer and subsequent boiling at 95° C. for five min. 20 µl of cell extract were loaded per lane.

Pull-Down and Peptide Competition Experiments

For peptide competition experiments 1 µg of antibody was incubated with 125 ng (10-fold molar excess per epitope binding site) peptide in the interaction buffer (TBS, 0.1 mM $CaCl_2$, 0.5% Blocking solution [Roche]) and preincubated for one hour at room temperature. Afterwards, 500 ng recombinant S100A4 was added and incubated for a further one hour at room temperature. To pull-down the antibodies 25 µL of Protein G Sepharose (Sigma) were added and incubated additional 30 minutes before washing for three times in TBS/0.05% Tween-20. The amount of coprecipitated S100A4 was analyzed by Western blotting assay.

T-Lymphocyte Invasion Assay

Invasion of primary mouse T-lymphocytes into fibroblast monolayers was tested using a modification of the methods of Stam et al. and Grum-Schwensen et al. (Stam et al., 1998; Grum-Schwensen et al., 2010). MEFs were grown to confluency in 12 well-plates; T-lymphocytes were labelled with Vybrant DID cell-labeling solution (Invitrogen) according to the manufacturer's instructions. Labeled T-lymphocytes ($4.5 \times 10^5$) were added to the wells and incubated for two hours. Non-invaded cells were removed by washing and mechanical agitation three times in PBS. The infiltrated cells were counted using a fluorescence microscope (Zeiss, Metamorph software) in ten random fields (magnification, ×10) per well. Invasion assays were performed in RPMI 1640 containing 10% FCS with or without 6 µg/ml rabbit IgG (Sigma-Aldrich) or 6 µg/ml mouse monoclonal anti-S100A4 antibodies (clone 6B12). The experiments were performed in quadruplicate and repeated three times.

Immunofluorescence Staining

For immunofluorescence staining to show the specificity of α-S100A4 mAbs MEF−/− or MEF+/+ were grown overnight on an eight-chambered glass coverslip using a reusable silicone chamber (Greiner Bio-One). Next day, the cells were washed with 1×PBS/Ca2+/Mg2+ and fixed with 4% paraformaldehyde for 20 minutes at room temperature. The cells were washed twice in PBS and permeabilized by incubating in PBS/1% Triton X-100 for 5 minutes. The anti-S100A4 mAbs were incubated with a concentration of 0.5 to 2 µg/mL in GlutaMax/10% FBS for 30 minutes at RT. After antibody incubation, the cells were washed 3-times with PBS for 3 minutes at RT, before the secondary antibody solution containing α-mouse AlexaFluor 488 (Invitrogen), DAPI (diluted 1:10000, Invitrogen) and phalloidin (diluted 1:3000, Sigma) were added and incubated for 30 minutes at room temperature, while being protected from light. Afterwards, the slides were washed and mounted with Fluoromount (SouthernBiotech, Birmingham, Ala., USA). Images were taken using laser scanning microscope LSM700 from (Zeiss, Germany).

Animal Experiments

A/Sn mice were subcutaneously injected (s.c.) with $1\times10^6$ CSML100 breast cancer cells in a volume of 200 µl/mouse and on the same day the loading dose (7.5 mg/kg in a volume of 100 µl) of antibodies was injected intraperitoneally (i.p.). Injections of antibodies were repeated three times a week. The animals were sacrificed 33-day post-transplantation by an intraperitoneal injection of pentobarbital (Euthanyl) followed by perfusion with PBS. The tumour tissue and lungs were paraffin-embedded, sectioned (4 µm), and stained with hematoxylin and eosin (H&E). The total metastatic burden was quantified by calculating the percentage area of each lung section occupied by metastases as described elsewhere (Grum-Schwensen et al., 2010).

Statistical Analyses and Computerized Analyses

Data are presented as average ±SEM. The confidence level was calculated using Student's t test. For the prediction of non solvent exposed amino acids of S100A4 we used Epitopia server (epitopia.tau.ac.il/index.html) a web-based tool which predicts immunogenic regions in a protein three-dimensional structure (Rubinstein et al., 2009). As input sequence we were using the calcium-bound dimeric human S100A4 (PDB ID: 2Q91)(Malashkevich et al. 2008).

Antibody Sequencing

Total RNA was isolated from the hybridoma cells following the technical manual of TRIzol® Plus RNA Purification System. The total RNA was analyzed by agarose gel electrophoresis. Total RNA was reverse transcribed into cDNA using isotype-specific anti-sense primers or universal primers following the technical manual of SuperScript™ III First-Strand Synthesis System. The antibody fragment was amplified according to the standard operation protocol of RACE of GenScript. Amplified antibody (VH and VL) genes were separately cloned into a standard cloning vector owned by GenScript using standard molecular cloning procedures. Colony PCR screening was performed to identify clones with inserts of correct sizes. No less than ten independent positive colonies were sequenced for each antibody fragment.

Production of Antibody-Targeted Gold Nanorods (GNRs)

The antibody was dialyzed against 10 mM sodium bicarbonate ($NaHCO_3$) pH 8.47. 100 µL of the antibody solution (5 mg/mL) was mixed with 166 µg Orthopyridyl disulfide functionalized polyethylene glycol OPSS (OPSS-PEG-NHS) linker (Creative PEGWorks) dissolved in 12.5 µL 100 mM $NaHCO_3$ and incubated for two hours at 4° C. The final concentration of antibody-linker was 32.5 µM. The GNRs were prepared using methods described in Nikoobakht & El-Sayed, (Preparation and Growth Mechanism of Gold Nanorods (NRs) Using Seed-Mediated Growth Method, Chemistry of Materials, 2003, 15: 1957-1962, 2003) or Niidome et al. (PEG-modified gold nanorods with a stealth character for in vivo applications, Journal of Controlled Release, 114, 343-347, 2006). They have an absorbance maximum at 805 nm a size of 40 nm to 10 nm. To remove cetyltrimethylammonium bromide (CTAB) from the GNRs, 1 mL solution of GNRs (1 nM) was centrifuged at 15.000 g for 10 minutes at RT. The supernatant was then decanted and the pellet resuspended in 1 mL $H_2O$. After removal of CTAB, 1.6 µL antibody-linker (OPSS-PEG-NHS) was added to 1 ml GNR solution. The GNRs were incubated for 24 hours at RT in the dark while rotating. Afterwards the GNRs were washed by centrifugation at 12.000 g at RT for 10 minutes. The GNR pellet was resuspended in a volume of 1 mL $H_2O$. For the biocoating with PEG the antibody-targeted GNRs were incubated with 200 µL 5 mM PEG-SH 5000 Da (PEGWorks) for 24 hrs. The modified GNRs were then washed as described before and resuspended in 1 mL $H_2O$.

Pull-Down Assay

The ability of the GNRs to bind S100A4 was tested by a S100A4 pull-down assay where 500 ng recombinant tetrameric mouse S100A4 was added to 1 ml of 1 nM solution of naked GNRs (GNR-CTAB), PEG coated GNRs (GNR-PEG), or antibody-linker coupled and PEG coated GNRs (GNR-PEG-Ab). The samples were incubated for 30 minutes at RT under rotation. The tubes were then centrifuged for 10 minutes at RT with 12.000 g. The supernatant was removed and the NPs resuspended in 1 mL 40 mM HEPES (Sigma) pH 8.6 with 0.5% NP40 (Fluka). The washing step was repeated twice. Finally the pellet was resuspended in 30 µL 1×SDS loading buffer. The samples were then boiled for 5 minutes at 95° C. and subjected to SDS-PAGE and Western blot as described elsewhere (Klingelhöfer et al., 2009). For the detection of the S100A4 protein the 6B12 monoclonal antibody was used.

Proliferation and Cytotoxicity Assays

To measure cell proliferation a MTT assay and to obtain the cytotoxicity a LDH assay was performed. $5\times10^1$ CSML100 cells were seeded in 96 well plates (Nunc) and maintained overnight in the incubator. Next morning, 50 µL of GNR solution or CTAB to a final concentration of 0.5 mM were added and incubated for 0, 24, or 48 hrs, before performing the MTT assay and collecting the samples for the LDH measurement. The samples were processed according to the procedure described in Klingelhöfer et al. (Klingelhöfer et al., 2009).

Lentiviral Transduction and Stable Cell Line Generation $1.5\times10^5$ target cells (MEF, MDA-MB-231) were seeded in a 6-well plate and incubated overnight at 5% $CO_2$ at 37° C. The next day after cells reached 50-60c confluency, the lentiviruses (Luc2 or mCherry) were thawed in a 37° C. warm water bath and immediately put on ice after defreezing. Pre-warmed infection medium was prepared by addition of polybrene at a final concentration of 5 μg/mL to DMEM medium. To 2 mL of modified medium, 100-300 μL of lentivirus of interest was added. For the first infection, medium was removed from the 6-well plate and replaced with 2 mL of lentivirus containing modified medium. The 6-well plate was gently rotated and incubated at 5 $CO_2$ and 37° C. In the evening, a second infection was performed. On day 3, medium was removed and replaced with 4 mL of pre-warmed DMEM medium. The next day, cells were trypsinized and transferred to a 25 $cm^2$ TC flask. 72 hrs after infection 1 μg/mL puromycin was added to the culture medium to select a successful infected cell population.

Thermal Ablation $4 \times 10^4$ MDA-MB-231/mCherry human breast cancer cell lines were seeded in each well of a 8-well chamber slide (Lab-Tek II, Nalge Nunc International). The cells were grown for 18 hours. Afterwards 1 μg/mL multimeric human S100A4 protein was added and incubated for 10 min. Cells were rinsed with PBS/$Ca^{24}$ and 50 μL of antibody-targeted GNRs in 200 μL pre-warmed DMEM were added and incubated for further 10 minutes. The excess of GNRs was washed away by PBS/$Ca^{2+}$. Finally, 200 μL pre-warmed DMEM with DAPI (1:10.000) was added before exposing the cells to NIR laser light. For thermal ablation a laser with a wavelength of 808 nm and a laser spot of 1.25 mm were used (ATC Semiconductor Devices). The cells were treated for a duration of 120 sec in intervals of 8 sec with the instrument set to 2 A, followed by a pause of 2 seconds. All pictures were taken using the Zeiss Axiovert S100TV microscope using the Metamorph software for the image acquisition.

In Vitro Bioluminescence/Fluorescence Imaging on IVIS® Spectrum

To screen bioluminescent/fluorescent activity in newly lentiviral transduced cells, we collected and counted the reporter gene expressing cells. A dilution series from 25.000 to 390 cells/well in a volume of 50 μL. Fresh D-luciferin substrate was prepared by pipetting 100 μL of D-luciferin (30 mg/mL) in 5 mL of prewarmed DMEM. 50 μL of D-luciferin substrate was added to each well containing bioluminescent cells. The 96-well plate was placed in the IVIS® Spectrum imaging system and after 2-3 minutes measurement was performed. Fluorescent cells were measured immediately in the IVIS® Spectrum imaging system. Measurements were performed according to the manufacture's instruction using the living imaging software 4.2 (Caliper LifeScience).

Mice and Tumour Cell Implantation

All animals were maintained according to the guidelines of the Federation of European Laboratory Animal Science Associations for the care and use of laboratory animals. Fluorescent MDA-MB-231/mCherry mammary carcinoma cells ($1 \times 10^6$) and MEF/Luc2 cells expressing the luciferase protein ($1 \times 10^6$) were mingled and injected s.c. in Balb/c nu/nu mice. The tumour growth and stroma development was monitored by in vivo imaging twice a week using the IVIS Spectrum (Caliper LifeScience) according to manufacturer's protocol. In brief, first the fluorescent signal was obtained, before injecting 150 μL D-Luciferin (BioSynth) solution (30 mg/mL) i/p in mice. The bioluminescent signal was measured 15-20 minutes after substrate injection.

Mice

Virgin female PyMT mice of A/Sn genetic background were used for experiments. Genotyping was performed as described in Grum-Schwensen et al (2010). All animals were maintained according to the Federation of European Laboratory Animal Science Associations guidelines for the care and use of laboratory animals.

Material and Methods for Further Experimental Examples

Animal Experiments

For spontaneous tumour model: 6-weeks-old PyMT female mice were injected with the loading dose (7.5 mg/kg in a volume of 100 μl) of the anti-S100A4 mouse monoclonal antibody, clone 6B12 or Rabbit IgG control intraperitoneally. Injections of antibodies were repeated three times a week.

The animals were sacrificed by an injection of pentobarbital (Euthanyl) followed by perfusion with PBS. The tumour tissue and lungs were paraffin-embedded and sectioned. Lungs were stained with hematoxylin and eosin, and the total metastatic burden was quantified by calculating the percentage area of each lung section occupied by metastasis as described in Grum-Schwensen et al (2010).

For pre-metastatic niche model: CSML100 mouse mammary carcinoma cells ($1 \times 10^6$) were injected s.c. to $S100A4^{-/-}$ A/Sn mice followed by i/v injection of $2.5 \times 10^5$ $S100A4^{+/+}$ or $S100A4^{-/-}$ mouse embryonic fibroblasts (MEFs) mixed with either 100 μg of the anti-S100A4 mouse monoclonal antibody, clone 6B12 or IgG control. The mice were also injected with the loading dose (7.5 mg/kg in a volume of 100 μl) of the anti-S100A4 mouse monoclonal antibody, clone 6B12 or IgG control intraperitoneally. Injections of antibodies were repeated three times a week. Injections of MEFs mixed with antibodies were repeated three times with 1-week intervals.

Animals were sacrificed 1 week after the last injection of MEFs mixed with antibodies (premetastatic phase).

Immunohistochemistry

Tumour and lung tissue sections were stained with affinity-purified rabbit polyclonal antibodies against CD3 and anti-α-smooth muscle actin, as described in Grum-Schwensen et al (2010). Corresponding secondary horse-radish peroxidase-conjugated antibodies were used followed by incubation with chromogenic substrate 3,3'-diaminobenzidine or 3-amino-9-ethylcarbazole. For double staining, secondary antibodies coupled to Alexa Fluor 488 or Alexa Fluor 568 (1:1,500) were purchased from Molecular Probes. Sections were examined by means of confocal microscopy on a LSM 510 (Carl Zeiss, Inc.). T-lymphocytes in the primary tumour were quantified by determining the amount of $CD3'$ cells in 3-4 fields from two sections of different part of the PyMT tumours (magnification, ×400) obtained from mice age 12 weeks (n=5-8 mice per group). Quantification of T-cells in the vicinity of blood vessels in pre-metastatic lungs (n=6 mice per group) was performed as described in in Grum-Schwensen et al (2010). Briefly, fluorescently labelled $CD3^+$ cells were counted in the surrounding of vessels visualized by staining with anti-α-smooth muscle actin antibodies. Ten vessels per section were selected for analysis.

T-Lymphocyte Purification by Magnetic Cell Sorting

T-cell purification was done as described in Grum-Schwensen et al (2011). Briefly, spleens were removed from mice, and single-cells suspensions were layered onto Lymphoprep and centrifuged to remove RBCs. Cells were purified by negative selection using the Pan T Cell Isolation kit (Miltenyi Biotech) according to the manufacturer's instructions. Cells were cultured in RPMI 1640 with 10% FCS.

Western Blot Analyses

Protein extracts from pre-metastatic lungs were resolved by SDS-PAGE. The protein expression of Fibronectin and Tubulin was analyzed using a standard Western blot procedure with anti-Fibronectin and anti-Tubulin antibodies.

Purified T-cells were starved in RPMI 1640 for 3 h and stimulated for 10 minutes with either multimeric S100A4 protein (1 µg/ml), mouse IgG (6 µg/ml), S100A4 protein (1 µg/ml) mixed with mouse IgG (1 µg/ml), mutant S100A4 protein (1 µg/ml), S100A12 protein (1 µg/ml), anti-S100A4 antibody (clone 6B12) (6 µg/ml), S100A4 protein (1 µg/ml) mixed with anti-S100A4 antibody (clone 6B12) (6 µg/ml), or rIL2 (10 ng/ml).

T-cells were treated with the Jak3-inhibitor (CP-690550) (100 nM) or the IRAK1/4 Inhibitor I (100 nM) for 30 minutes before stimulation with S100A4 protein (1 µg/ml) for 10 minutes.

Cell lysates were prepared in the presence of protease- and phosphatase-inhibitors and resolved by SDS-PAGE. Activation of the Jak3-Stat3 signaling pathway was analyzed using a standard Western blot procedure with phospho-Janus Kinase 3 (Jak3; $Tyr^{980}/Tyr^{981}$), phospho-Signal Transducer and Activator of Transcription 3 (Stat3; $Tyr^{705}$), and Jak3 and Stat3 antibodies (Cell Signaling Technology). Membranes were stripped with ReBlot Plus (Millipore) before re-blotting for Jak3 and Stat3.

RNA Sample Preparation and Quantitative Real-Time Polymerase Chain Reaction (qRT-PCR)

Total DNA-free RNA was prepared from the PBS-perfused lungs with the NucleoSpin® TriPrep kit (Macherey-Nagel) according to the manufacturer's instructions. First-strand cDNA synthesis was performed using Super-Script III RT (Invitrogen) with random primers according to the manufacturer's instructions.

Real-time PCR was performed using a LightCycler 2.0 instrument following the manufacturer's instructions (Roche Applied Science, USA). The following primers were used: mouse Fibronectin forward primer: (5'-TGCCGCAAC-TACTGTGAT-3'; SEQ ID NO: 25), mouse Fibronectin reverse primer: (5'GAATCCTGGGCTGGAGTA-3'; SEQ ID NO: 26), mouse G-CSF forward primer: (5'-CAGAT-CACCCAGAATCCAT-3'; SEQ ID NO: 27), mouse G-CSF reverse primer: (5'-CTCTCGTCCTGACCATAGTG-3'; SEQ ID NO: 28), glyceraldehyde 3-phosphate dehydrogenase (GAPDH) forward primer for normalization: (5'-TCATCCCTGCATCCACTG-3'; SEQ ID NO: 29), and GAPDH reverse primer (5'-TAGGAACACGGAAGGCCA-3'; SEQ ID NO: 30).

Expression of all genes was normalized to the level of GAPDH expression. The expression level of each gene achieved from the control sample was set to 1 and the relative expression level was calculated.

Flow Cytometry

Purified T-cell cultures were maintained for 3 or 6 days and activated with anti-CD3 and anti-CD28 antibodies coupled to MACSibeads particles (Miltenyi Biotec) plus 10 ng/ml recombinant IL2 as described in Jimeno et al. (2012).

Activated T-cells were also stimulated with multimeric S100A4 protein (1 µg/ml) or S100A4 protein mixed with anti-S100A4 antibody (6 µg/ml).

After 3 and 6 days, PMA/Ionomycin and Golgistop™ (BD Biosciences) were added to the medium, for 5 hours. Cells were washed with PBS and Fixable Viability Stain 450 (BD Biosciences) was added to discriminate between viable and dead cells.

Cells were fixed using the Cytofix/Cytoperm™ kit (BD Biosciences) and stained with the mouse Th1/Th2/Th17 phenotyping kit (BD Biosciences) according to the manufacturer's instructions. Fixed T-cells were stained with a cocktail containing PERCP-CY5.5-conjugated anti-mouse CD4, PE-conjugated anti-mouse IL17A, FITC-conjugated anti-mouse IFNγ, and APC-conjugated anti-mouse IL4 antibodies.

Data Acquisition and Analysis were Performed on a FACSVerse (BD Biosciences) Using FlowJo Software (Tree Star).

Cytokine Microarray Analysis

Pre-metastatic lungs were isolated and propagated ex-vivo for 2 hours in PBS at 37° C. Conditioned medium from individual lungs was sterile filtered pulled together in groups (n=5) and used for cytokine antibody array analysis. RayBio Mouse Cytokine Antibody Arrays 3 and 4 were purchased from RayBiotech, and the cytokine analysis of the ex-vivo cultures were carried out according to the manufacturer's instructions.

Statistical Analysis

The confidence level was calculated using paired or unpaired Student's t test.

Materials and Methods for BIAcore Binding Studies

All SPR analyses were conducted on a BIAcore 2000 system (GE-Healthcare Life Sciences, Upsala, Sweden). The experiments were performed at 25° C. using HBST/Ca (10 mM HEPES, 150 mM NaCl, 0.005% Tween® and 50 µM CaCl2) as running buffer. The S100A4 protein was immobilized on a sensor chip CM5 (GE-Healthcare, BR-1000-12) using the amine coupling kit from GE Healthcare (BR-1000-50). The flow rate was set to 5 µl/min. The flow cells were activated individually by injecting 35 µl freshly mixed 0.4 M EDC ((N-(3-dimethylaminopropyl)-N'-ethylcarbodiimide hydrochloride) in 0.05 M NHS (N-hydroxysuccinimide) solution. Then 5 µg/ml S100A4 protein diluted in 10 mM acetic acid, pH 5.0 was injected for 1 to 10 minutes until the desired level of immobilization was reached (about 400 to 800 RU). The remaining active groups were deactivated by injecting 35 µl 1 M ethanolamine (pH 8.5). All experiment included a reference surface which was prepared by activating and deactivating of the surface of flow cell 1 (FC1). The blank surface reference was used to correct for bulk effects and nonspecific binding. The channel referencing was done automatically by the BIACORE 2000 control software.

The injections were performed using the KINJECT mode (injection10 min, dissociation 20-30 min). The flow rate during injection and regeneration was kept at 50 µl/min. For regeneration of the sensor chip surface 10 µl 50 mM NaOH was injected.

A blank buffer reference was always included in each dilution series. A basement alignment to adjust all sensorgrams to the same zero-baseline level along the y-axis and (if necessary) an injection alignment was performed along the x-axis for each data group in a dataset. Artefacts were removed of the sensorgrams by using corresponding function of the BIAevaluation software 4.1 (GE Healthcare). The kinetic constants were calculated from sensorgrams by fitting to the 1:1 binding (Langmuir) model of the BIAevaluation software 4.1.

Results

Production of a Panel of S100A4-Specific Monoclonal Antibodies

S100A4 specific antibodies were raised by immunizing mice using the recombinant mouse S100A4 protein. For screening of the hybridoma clones the mouse S100A4 was used. After screening of a panel of specific S100A4 monoclonal antibodies, three mAb (3B1C4, 11F8.3 and 6B12)

displaying the strongest affinity in the ELISA screen were selected for further analysis. All three antibodies belong to the mouse IgG$_1$κ isotype.

The specificity of obtained antibodies was first analyzed by screening for their ability to recognize human S100A4 protein or cross-react with members of the human S100 family. As shown in FIG. 1A the mAB 3B1C4 and 6B12 recognized both mouse and human S100A4 protein, while the 11F8.1 only reacts with the mouse protein. This is remarkable since the sequence of human and mouse S100A4 are different only at 6 amino acids. Importantly all three antibodies showed no cross-reactivity to other S100 family members (FIG. 1A).

Immunocytochemical analysis showed that all three antibodies were able to detect S100A4 protein expressed in mouse embryonic fibroblasts. S100A4 immunoreactivity was observed in cytoplasm and in perinuclear area in complete accordance with previously reported data (Kriajevska et al., 1994). S100A4 knock-out mouse embryonic fibroblasts, MEF$^{(-/-)}$, served as a negative control (FIG. 1B). Finally, we tested the recognition of endogenous S100A4 protein in total cell extracts from human and mouse cancer cell lines and from S100A4$^{(+/+)}$ and S100A4$^{(-/-)}$ MEFs (FIGS. 1C and D). In accordance with data in FIG. 1A, the antibody 11F8.3 recognized only mouse protein, whereas two other antibodies were able to recognize both mouse and human S100A4. In contrast to the other clones, the 3B1C1 recognized additionally some unidentified proteins of 55 and 90 KDa. This cross-reactivity makes the 3B1C1 antibody less useful for further analysis.

Analysis of Function Blocking Activity of Anti-S100A4 Antibodies

Since the purpose of this study was to isolate an antibody with metastasis-blocking activity we decided to perform preliminary analyses that included in vitro and in vivo assays. We choose the ability of S100A4 protein to stimulate cell invasion in 3D Matrigel matrix invasion assay (Schmidt-Hansen et al., 2004b). The invasion of MEFs in 3D Matrigel matrix was stimulated by VMR mouse mammary carcinoma cell conditioned media with or without addition of S100A4. FIG. 2A shows that addition of S100A4 stimulates invasion of MEFs into the matrix. The 6B12 antibody added to the cultivation medium successfully blocked the invasion of MEFs (FIG. 2A, left panel). The blocking ability of all three antibodies was compared to the control by semi-quantitative assessment of the extent of the invasive growth (FIG. 2B). The 11F83 antibody was not able to block the S100A4-stimulated invasion of fibroblasts into the Matrigel. The 6B12 and 3B1C4 blocked the invasion to similar extent. Since we were interested in selection of metastasis-blocking antibody with applicable for human cancer, we analyzed the ability of 6B12 antibody to block invasion of human fibroblasts in 3D Matrigel invasion assay. FIG. 2C shows semi-quantitative analysis of the extent of invasion of HMF3s human mammary fibroblast cell line stimulated by human S100A4 recombinant protein in the presence of MCF7 breast carcinoma cell conditioned media and the ability of 6B12 antibodies to block this process.

To select one antibody for further analysis, we also performed a pilot study comparing the ability of all three antibodies to block tumour growth and metastasis formation by CSML100 mouse mammary carcinoma cells, that direct metastatic spread of cancer cells to the lung in spontaneous metastasis assay (Ebralidze et al., 1989). Tumour-bearing mice were treated by i/p injection of antibodies 3 times weekly starting from the day of tumour graft. Comparison of the dynamics of tumour growth in mice administered with these mAb did not reveal statistically significant difference between groups (Table 1):

| α-S100A4 mAb | 3B1C4 | 11F8.3 | 6B12 |
|---|---|---|---|
| number of mice (N) | 7 | 6 | 7 |
| average tumour size [mm$^3$] | 200.7 ± 39.05 | 230.3 ± 21.90 | 176.6 ± 23.91 |
| metastatic burden [%] | 3.246 ± 1.707 | 4.878 ± 2.170 | 0.4997 ± 0.2345 |
| average weight loss before/after [g/g] | 26.6/25.5 Δ 3.01% | 26.4/25.6 Δ 4.55% | 26.1/24/6 Δ 5.75% |

After the termination of experiment at day 33 due to the maximal allowed tumour size, lungs of the tumour-bearing mice were isolated and the metastatic burden in the lungs was determined as described earlier (Møller et al., 2011). In course of experiment no significant toxicity was observed in any treatment group and mean body weights were not significantly different with antibody treatment (Table 1). The three antibodies used in this analysis exhibited substantial relative difference in the metastasis-blocking activity. The 6B12 antibody showed the most pronounced tendency in suppression of metastasis (note: ns p=0.052). The 11F8.3 antibody showed the highest metastatic burden in lungs of tumour-bearing mice. This was in good correlation with 3D Matrigel invasion assay, since this mAb did not block the invasion of fibroblasts (FIG. 2B). The 3B1C4 antibody showed a weak tendency in metastasis neutralizing activity (Table 1). Summarizing the data obtained from the comparative analyses of three antibodies presented above we choose the 6B12 antibody for more detailed study.

α-S100A4 mAb Significantly Reduces the Metastatic Burden in Lungs and Suppresses T Cell Accumulation in Primary Tumour The 6B12 antibody was injected three times weekly i/p into mice grafted with CSML100 cancer cells. As it was shown in the previous section the extent of tumour growth did not differ from the control group of animals. We even mentioned a tendency to a bigger tumour size in the 6B12-injected group, which was not statistically significant (FIG. 3A). The experiment was terminated at the time point when the tumour size of the first animal reached the maximal permitted size. This enabled us to accurately compare the extent of metastasis in experimental and control groups. Histological analysis of lung tissue sections revealed first that the overall amount of metastasis-free animals was significantly higher in the 6B12-treated group (45% versus 19% in the control). Moreover, the metastatic burden in the 6B12-treated group was also significantly reduced (P<0.02) (FIGS. 3A and B).

Immunohistochemical staining of primary tumour sections with antibodies specific for endothelial cells (CD31) and T cells (CD3) was performed to characterize the stroma compartment of the tumours. These stainings revealed that treatment with 6B12 antibodies did not affect the vessel density, but substantially reduced the amount of T cells accumulated in the vicinity of the tumour (FIG. 3C). This confirms our previous observations that S100A4 stimulates recruitment of immune cells to the site of growing tumour.

We propose therefore that T cells accumulated to the site of the primary tumour in response to S100A4 could produce factors that stimulate metastatic spread of cancer cells. The interference of the S100A4 neutralizing antibodies could compromise production of these factors and as a consequence prevent the spread of tumour cells.

To confirm the observed reduction of T cell accumulation in the primary tumours in response to the 6B12 antibody treatment we performed in vitro analysis of T cell invasion in presence of 6B12. In our previous studies, we have shown that the S100A4 positive, but not S100A4 negative, fibroblasts substantially stimulate the ability of T cells to invade the fibroblast monolayer (Grum-Schwensen et al., 2010). Our attempt to block T cell invasion in this assay showed that 6B12 antibody significantly reduced T cell invasion into the S100A4-positive fibroblast monolayer (FIG. 3D).

Determining of the Recognition Site of the 6B12 Antibody

Figure 4:
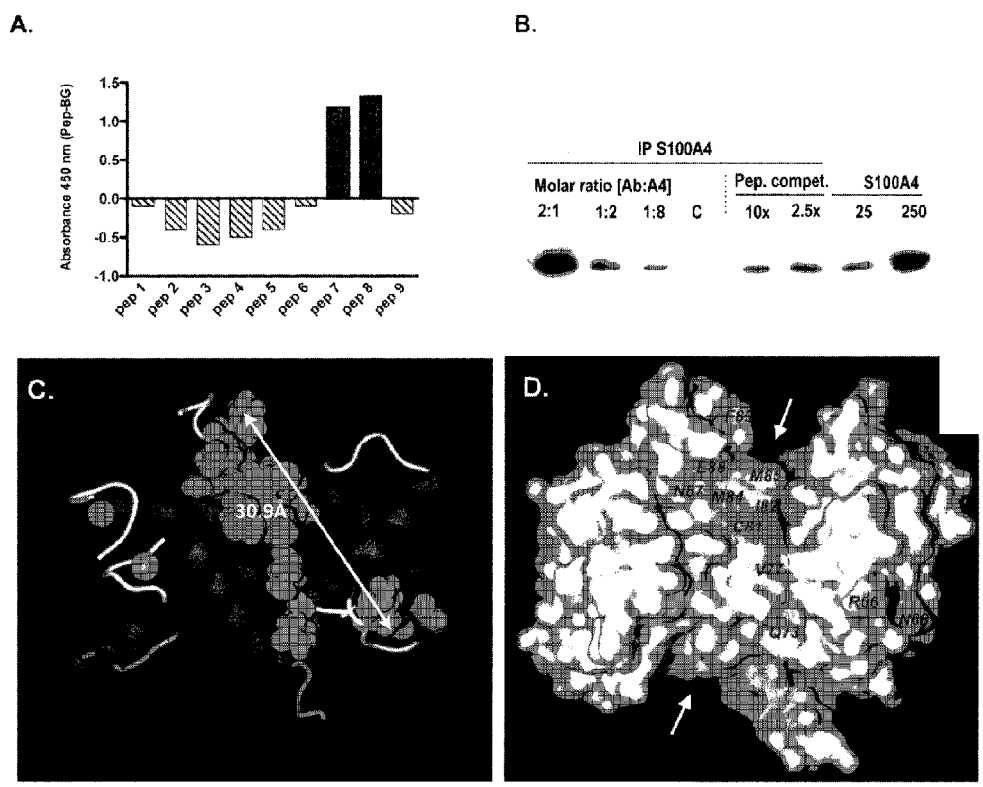
FIG. 4. Epitope mapping revealed a planar patch on the dimaric S100A4 governing the epitope for antibody 6B12. (A) The epitope was characterized by screening of non-overlapping 10- to 12-mer peptide sequences of the human S100A4 protein consisting of 101 amino acids by ELISA. The screening revealed binding of the 6B12 mAb to peptide 7 (RDNEVDFQEYCV, 12-mer: 66-77; SEQ ID NO: 13) and peptide 8 (FLSCIAMMCNEF, 12-mer: 78-89; SEQ ID NO: 14). Peptide 7 forms the second EF hand (aa 78-86) and peptide 8 forms a part of the α-Helix IV. In addition, residues of peptide 7 and 8 are forming the hydrophobic cleft for binding with target proteins (Malashkevich et al., 2008). (B) 6B12 epitope is accessible on soluble native conformation of S100A4 protein. The competitive immunoprecipitation assay showing the pull-down of oligomeric S100A4 in solution by the 6B12 antibody (in different molar ratio). The binding to S100A4 was partially blocked by "epitope" peptide 8 at 10- and 2.5-fold molar access. 25 and 250 ng/lane recombinant S100A4 was loaded as control. (C) The ribbon diagram represents the molecular structure of the calcium bound S100A4 dimer (2Q91). The residues making the potential 6B12 epitope are indicated in green (only residues of the A chain are coloured). The potential epitope is made of 4 amino acids of peptide 7 (Arg66, Asn68, Gln73, Val77) and seven amino acids from peptide 8 (Cys81, Ile82, Met84, Met85, Asn87, Glu88, Phe89). The planar patch has a rugged surface at atom level. The line indicates the size in diameter of the patch about 30.9 Å. Calcium atoms are shown in orange. (D) Molecular surface visualisation of S100A4 shows the predicted epitope region located in the hydrophobic cleft for target protein interaction. The surface of the epitope patch formed from the subunit A is coloured in green. Amino acids forming the epitope patch are labeled. The white arrows indicating the cleft for target binding. After excluding amino acids which are not in the same planar level and are not solvent exposed the potential epitope sequence consists of 24 amino acids with following segmented structure: $_{66}$R-N- - - -Q- -V- - -CI-MM-NEF$_{89}$ (SEQ ID NO: 15). Analyses and imaging was performed with the Molegro Molecular Viewer software v. 2.2.0/mac (Molegro ApS, Denmark).

To further proceed in clarifying the mechanism of 6B12 neutralising activity it is essential to determine the antibody recognition site. Epitope mapping analyses by screening the binding of 6B12 antibody to non-overlapping 10- to 12-mer peptide sequences of the entire human S100A4 protein by ELISA assay revealed binding of the 6B12 mAb to peptide 7 (RDNEVDFQEYCV, 12-mer: 66-77; SEQ ID NO: 13) and peptide 8 (FLSCIAMMCNEF, 12-mer: 78-89; SEQ ID NO: 14) (FIG. 4A).

Peptide 7 forms the second EF-hand (aa 78-86) for $Ca^{2+}$-coordination and peptide 8 forms a part of the α-Helix IV of the S100A4 protein. In addition, residues of peptide 7 and 8 are forming the hydrophobic cleft for binding with target proteins (Malashkevich et al., 2008). The hydrophobic cleft has been also shown to be involved in the self-association of tetramers which are formed from two identical homodimeric subunits. Competitive immunoprecipitation assay revealed that peptide 7 and 8 block the interaction of 6B12 antibody also with the native protein (FIG. 4B).

Based on our previous findings that the 6B12 antibody recognizes human and mouse S100A4 protein and it recognizes S100A4 in solution, we performed a computer-assisted analysis to predict the recognition epitope on the S100A4 protein structure. We analysed the published structure of calcium-bound dimeric S100A4 in a resolution of 1.63 Å (PDB ID: 2Q91; Malashkevich et al., 2008) by the Epitopia web-server for amino acids which were buried in the tertiary structure or potentially accessibly for the antibody binding (Rubinstein et al., 2009). This approach, using human peptide 7 and 8 sequence as the core region of the antibody-S100A4 interface, which are identical with the mouse sequence revealed a planar structure of about 30.9 Å (FIG. 4A) for the possible 6B12 epitope. The suggested surface of the planar patch is formed by five amino acids from peptide 7 (Arg66, Asn68, Asp71, Gln73, Va177) and seven amino acids from peptide 8 (Cys81, Ile82, Met84, Met85, Asn87, Glu88, Phe89) (FIG. 4B). Amino acids which could not participate in the epitope surface, because they are hidden in the protein structure and amino acids which are not in the same planar level to participate in the antibody binding were excluded as well (See details. Tab. 2). The potential epitope is made of 24 amino acids matching the expected length of an typical antibody epitope with an average of 20 amino acids (Rubinstein et al., 2008). Correspondingly the peptide which could be suggested as the potential epitope consists of following sequence $_{66}$R-N- - - -Q- - -V- - -CI- -MM-NEF$_{89}$ (SEQ ID NO: 15).

Production and Characterization of S100A4/Antibody-Targeted GNRs

The GNRs had an absorbance maximum at 805 nm and an average length of 40 nm with a diameter of 10 nm (FIG. 7A). Using the bifunctional linker OPSS-PEG-NHS, we attached the anti S100A4 6B12 antibody to GNRs, before PEGylation by PEG-SH (5000 Da). The success modification of the GNRs and the ability to bind S100A4 was tested by a S100A4-pull-down assay. FIG. 7B shows that naked GNRs (GNR-CTAB) pulled-down S100A4. The binding of S100A4 is likely due to the interaction of the gold surface of the NRs with thiol groups of the S100A4 protein. After coating the bare GNRs with PEG (GNR-PEG), the interaction with S100A4 was completely abolished. Attaching the 6B12 antibody via a linker prior the PEGylation, enabled the functionalized GNRs to pull-down the S100A4 protein antibody-dependent (FIG. 7B).

After successful proof that the 6B12 antibody was attached and functional active, we tested whether the GNRs display any cytotoxicity. We compared untreated cells to antibody-targeted GNRs (Ab-GNR) by MTT assay. 0.5 mM CTAB with its well-known cytotoxicity served as control. The metabolic activity increased over time from 0 to 48 hrs, however, it was not different between the untreated and GNR-treated cells, indicating that the GNRs did not affect the viability of the cells. The LDH returned similar result showing that the cell death dependent concentration of LDH in the conditioned media was similar in untreated and antibody-targeted GNR treated cells. In summary the 6B12/antibody-targeted GNRs displayed no significant cytotoxicity in vitro.

Creation of Dual Reporter In Vivo Imaging Tumour Mouse Model

To study the targeting and thermal ablation effect of the GNRs we generated two reporter cell lines: fluorescent human breast cancer cells (MDA-MB-231/mCherry) and bioluminescent fibroblasts (MEF/Luc2) by lentiviral infection (see scheme, FIG. 8A). The cell lines showed sufficient and stable expression of the reporter after 4 weeks in culture without selection pressure of the antibiotic puromycin, rendering these cells useful for in vivo imaging (FIG. 8B). The expression of the two reporter genes allow us almost simultaneously to follow tumour cell and stroma cell (here: fibroblasts) regression after treatment in life animals. To evaluate the in vivo imaging capabilities of the cell lines we mingled the MDA-MB-231/mCherry and the MEF/Luc2 cells before subcutaneous engraftment into nude mice. After subcutaneous engraftment of both reporter cells in immunocompromised mice (nu/nu), we followed the tumour/stroma development during 8 weeks. FIG. 8C shows the detection of both cell types in the developing subcutaneous tumours 10 days after the cell mix engraftment (FIG. 8C).

Photothermal Ablation of Tumour Cells in Cell Culture

To prove the efficiency of functionalized GNRs MDA-MB-231/mCherry tumour cells were incubated with S100A4 protein for 10 minutes. Afterwards the S100A4 targeting GNRs were applied. Non-bound GNRs were washed away before exposing the tumour cells to NIR-laser light (2 W for 8 sec interval). The damage inflicted upon the cells was visualized by the DNA-specific dye DAPI which was present in the culture medium. When cells were affected by the thermal energy they lost their membrane integrity and became more permeable to the dye. Affected cells were therefore visualized by the strong blue staining of their nuclei. At the same time the cytosolic fluorescent mCherry protein was released into the cell culture medium, as shown in FIG. 9A (left image: with antibody-targeted GNRs). MDA-MB-231/mCherry cells without antibody-targeted GNRs where not affected by the laser treatment (FIG. 9A, right image). The time lapse with duration of 120 sec and repeated pulses of 8 sec laser exposure was recorded of antibody-targeted GNRS shown in FIG. 9A (FIG. 9 B). After 20 sec the thermal effect was visible at the laser spot. This result clearly indicates that the laser energy alone is not sufficient to compromise membrane integrity and the thermal effect is mediated by the presence of cell-bound GNRs.

Results for Further Experimental Examples
In Vivo Studies
Spontaneous Development of Mammary Cancer which Give Rise to Lung Metastasis Spontaneous breast cancer model (PyMT mice) is similar to human breast cancer: Hyperplasia, adenoma mammary intraepithelial neoplasm (MIN), carcinoma, late carcinoma, pulmonary metastases. Note, S100A4 is up-regulated and released from stroma cells early during tumour development at the benign stage (adenoma/MIN). To show efficacy of the 6B12 antibody therapy this model is most valuable because (i) it closely resembles human breast cancer, (ii) mice are immuno-competent and (iii) tumours develop spontaneously at natural site and environment.

Modal of Pre-Metastatic Niche Formation

Briefly the model is based on the ability of S100A4 positive fibroblasts to restore the capacity of CSML100 cells to form metastases in the lungs of S100A4-deficient mice. Tumour-bearing S100A4-deficient mice were saturated with S100A4-positive fibroblasts by intravenous injection (Grum-Schwensen et al 2010) and concurrently treated with 6B12 antibody (intraperitoneal injection).

PymT Mouse Model and 6B12 Antibody Effects

Figure 10:
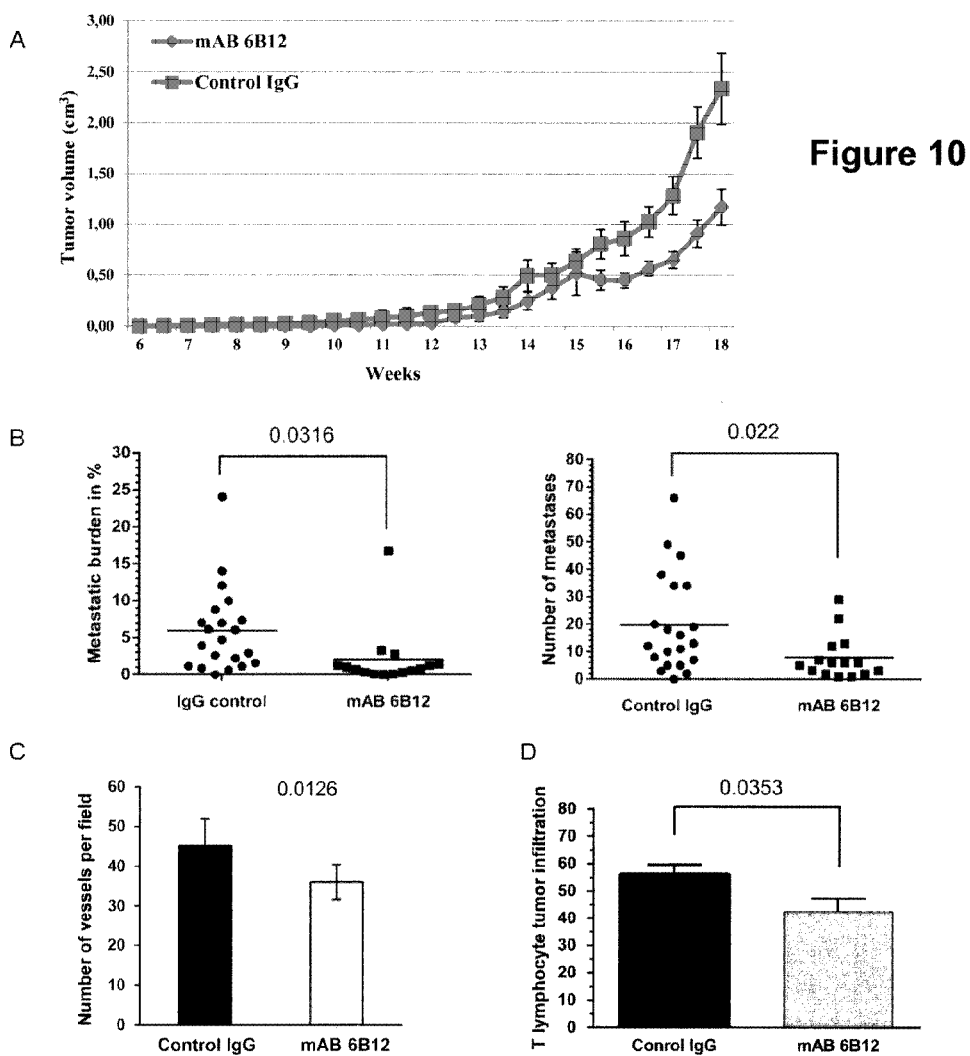
FIG. 10. Effect of 6B12 antibody on tumour growth, metastases and stroma development in PyMT mice. (A) 6B12 antibody treatment lead to delay in tumour development and a significant reduction in the rate of tumour growth (n=15 for each group). (B) Both pulmonary metastatic burden and number of metastases are reduced by 6B12 antibody treatment. Statistical confidence level shown. (C) 6B12 antibody reduces blood vessel density in primary tumours of PyMT mice. Statistical confidence level shown. (D) 6B12 antibody reduces number of T cells attracted to the tumour at the early stage (adenoma/MIN) of PyMT tumour development. Statistical confidence level shown.

The spontaneous metastatic mouse mammary tumour (PyMT) model was used to confirm the ability of anti-S100A4 antibodies to suppress tumour growth and metastasis formation. Intra-peritoneal injection of S100A4 neutralizing 6B12 antibody to PyMT tumour-bearing mice showed that treatment with this antibody not only lead to suppression of metastasis formation, but also to delays in the emergence of first measurable tumour and significant reduction in the rate of tumour growth (FIG. 10A). This was an exciting observation because no changes were detected in the dynamics of tumour development in PyMT mice bred to the S100A4 (−/−) genetic background (Grum-Schwensen et al 2010).

The animals of experimental group and a control group were sacrificed when the tumour reached maximal allowed size, or at 18-week-old. Metastatic burden as well as overall number of metastases in the lungs of 6B12-treated mice was determined and compared to the lungs of control group (FIG. 10B). Both parameters were significantly reduced in the 6B12-treated group. The fact that in spontaneous tumour model the 6B12 antibody delays the tumour onset and suppresses the dynamics of tumour development opened the possibility that at the early steps of tumour onset S100A4 activity executes its pro-angiogenic function (Ambartsumian et al., 2001, Schmidt-Hansen et al., 2004). Indeed comparison of the vessel density in the primary tumour of control group versus 6B12-treated group showed substantial decrease in the 6B12-treated group (FIG. 10C). The affect of treatment with 6B12 antibody on the accumulation of T cells at the pre-malignant stage of tumour development, as was shown for the S100A4(−/−) PyMT mice, was investigated. Indeed, quantification of the number of T cells accumulated in the vicinity of adenoma(MIN)/early carcinoma nodules demonstrated significant reduction in the amount of T cells in tumour-bearing mice treated with 6B12 antibody (FIG. 10D).

The Pre-Metastatic Niche Mouse Model and 6B12 Antibody Effects

Figure 11A:
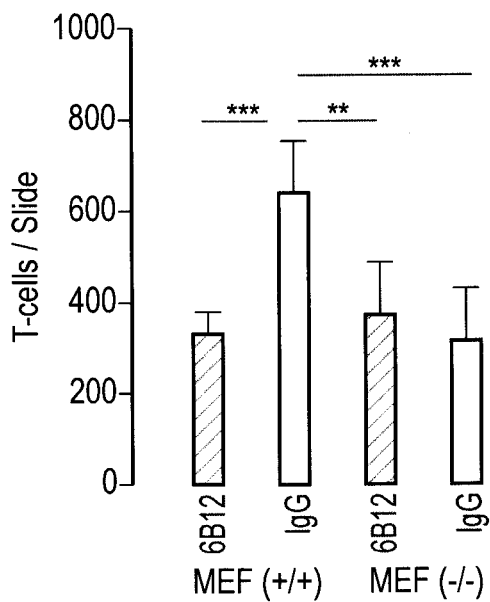
FIG. 11. Effect of 6B12 antibody on the premetastatic niche formation. (A) Quantification of the number of T cells accumulated in the pre-metastatic lungs of the tumour-bearing mice treated with 6B12 antibody. Statistical confidence level shown  P</=0.01; * P</=0.001. (B) qRT-PCR analysis of the level of fibronectin and G-CSF expression in the pre-metastatic lungs of individual animals treated with 6B12 antibody. (C) Quantification of the fibronectin protein in the lungs of individual mice treated with 6B12 antibody FIG. 12. Flow cytometry analysis of changes in Th1/Th2 polarization induced by S100A4 changes in vitro that is restored by the 6B12 antibody. (A) Flow cytometry shows decrease in the proportion of Th1 cells after S100A4 treatment of T cells. (B) Quantification of Th1/Th2 ratio of T cells differentiated in presence of S100A4 for 3 and 6 days. Statistical confidence level shown. (C) Flow cytometry analysis of Th/1/Th2 ratio determined after treatment with 6B12 antibodies.

S100A4-deficiency lead not only to suppression of T cell accumulation at pre-malignant stage of primary tumour, but also reduces T cell accumulation in the lungs at a pre-metastatic stage. Reduction in the numbers of metastatic nodules in the lungs of PyMT tumour-bearing mice by 6B12 antibody raised the possibility that it can suppress the pre-metastatic niche. To assess the effect of 6B12 antibody on pre-metastatic lungs, hallmarks of the pre-metastatic niche were investigated (Kaplan et al., 2006). Treatment with 6B12 antibodies lead to reduction of T cells accumulated around the vessels in the pre-metastatic lungs. Quantification showed that 6B12 antibody significantly decreased the number of T cell accumulated around the blood vessels (FIG. 11A).

Figure 11B:
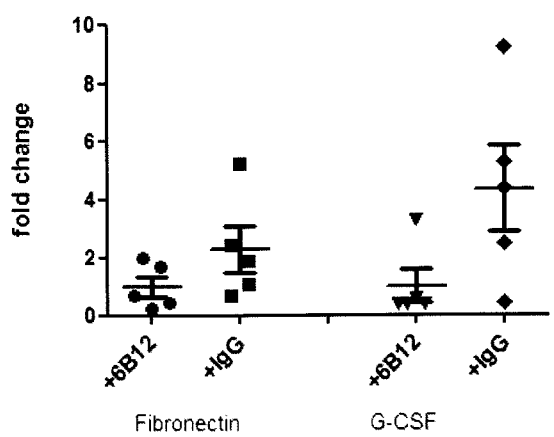

One of the indications that lungs are pre-conditioned to accept metastatic cancer cells is accumulation of fibronectin (FN) (Kaplan et al., 2005). qRT-PCR and Western-blot analysis of FN expression in pre-metastatic lungs of tumour-bearing mice treated with 6B12 antibody revealed reduction of the FN RNA in pre-metastatic lungs from mice treated with 6B12 antibody (FIG. 11B). It has been shown earlier that S100A4 stimulated release of G-CSF from T cell; increased level of G-CSF was detected also in tumour interstitial fluid of S100A4(+/+) compared to the S100A4 (−/−) PyMT mice (Grum-Schwensen et al. 2010). Therefore the expression of G-CSF in lungs of tumour-bearing mice was analysed. qRT-PCR analysis showed that 6B12 antibody treatment lead to the reduction of the level of G-CSF in pre-metastatic lungs (FIG. 11B).

Figure 11C:
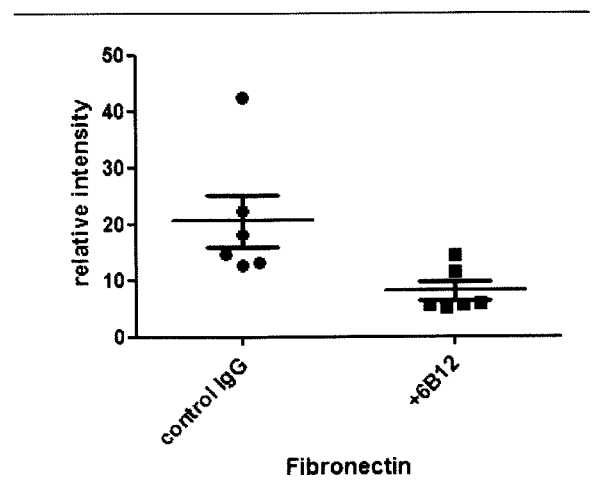

FN is a stable protein and its deposition in the lung tissue can vary substantially from the RNA expression levels so it was investigated whether the FN protein levels vary in lungs of 6B12 treated and non-treated mice. Western blot analysis of the FN protein levels in the pre-metastatic lungs of individual tumour-bearing animals showed significant suppression of FN after 6B12 treatment (FIG. 11C). These results show that anti-S100A4 antibody neutralizing activity is not only associated with its ability to block accumulation of T cells at pre-malignant stage of primary tumour development and inhibition of angiogenesis, but also is extended to the whole body level by its ability to block the formation of favourable pro-metastatic milieu in the 10 secondary organs, such as lungs.

In Vitro Studies
6B12 Antibody Restores the In Vitro T Cell Lineage Differentiation Pattern Modified by S100A4

Treatment of T cells with S100A4 in vitro lead to activation of MAP-kinase pathway and to stimulation of production of certain cytokines, including G-CSF and Eotaxin 2 (Grum-Schwensen et al 2010). In vivo cytokine antibody array analysis of the conditioned medium from ex-vivo pre-metastatic lung organotypic cultures revealed altered expression of a number of cytokines (Table 3). Levels of G-CSF and eotaxin 2 were elevated. In addition, increased levels of IL-4, IL-9 and IL-6 were detected. In contrast, levels of IFN-gamma and IL-1 (alpha and beta) were reduced. Without wishing to be bound by any particular theory, the present inventors believe that S100A4 executes its pro-metastatic function by attracting T cells and altering its lineage differentiation pattern, that lead to changes in the microenvironment of the organ that are favourable to accept metastatic tumour cells.

Figure 12A:
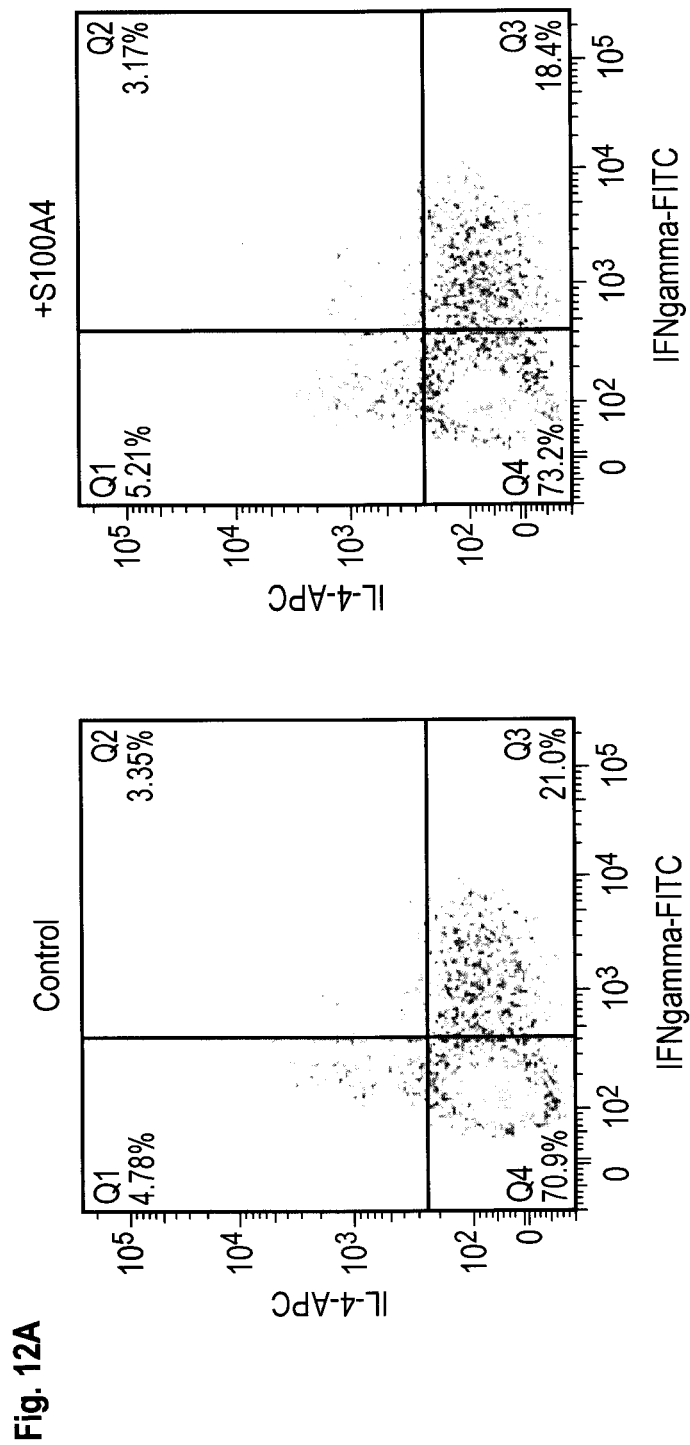
Figure 12B:
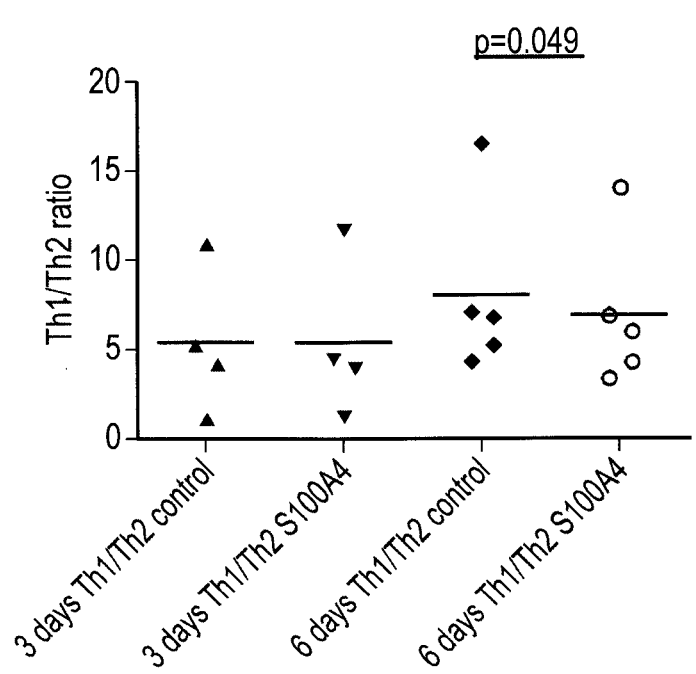
Figure 12C:
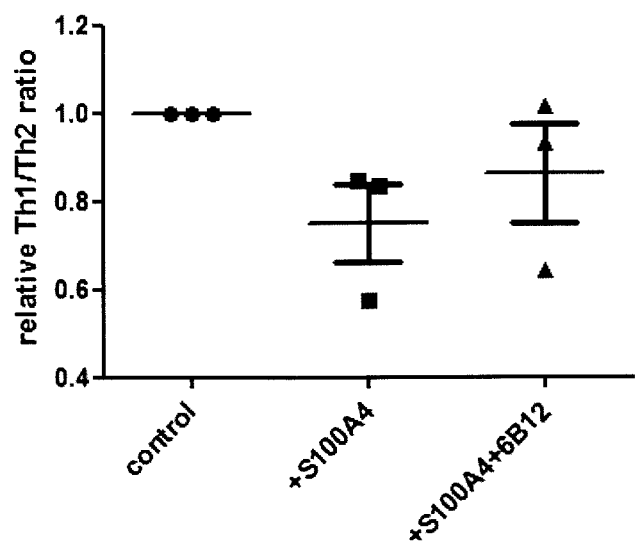

To test the hypothesis that S100A4 can shift the T cell lineage differentiation balance the long term effects of S100A4 on T cells were investigated. Isolated T cells were primed and propagated in the presence of CD3/CD28/IL2 and S100A4. The Th1/Th2 ratio was then determined at 3 and 6 days of growth by flow cytometry. In vitro differentiation conditions used in this experiment lead to the increase of the proportion of CD4+T helper 1 (Th1) cells at 6 days in culture. The increase in the proportion of Th1 cells in the S100A4 treated culture was significantly lower than in the control population (FIGS. 12A and B). The proportion of Th2 cells remained unchanged. It was investigated whether the addition of 6B12 antibodies in the S100A4-treated population would restore the Th1/Th2 balance. The data in FIG. 12C shows that the Th1/Th2 polarization balance is restored by 6B12 antibody. This indicates that the observed shift in Th1/Th2 lineage differentiation pattern is dependent on S100A4.

6B12 Antibody Blocks the Signalling Pathways of T Cell Differentiation Activated by S100A4

Treatment of T cells with S100A4 in vitro lead to activation of MAP-kinase pathway. It was also shown that S100A4 activates Jak-Stat signal transduction pathway in neuronal cells (Grum-Schwensen et al., 2010, Dmytriyeva et al., 2012). It is therefore proposed that mechanistically S100A4 shifts the T cell differentiation pattern by activating specific T cell differentiation signal transduction pathways, in particular Jak/Stat pathway (Zhu et al., 2008; Ghoreschi et al., 2009).

Figure 13:
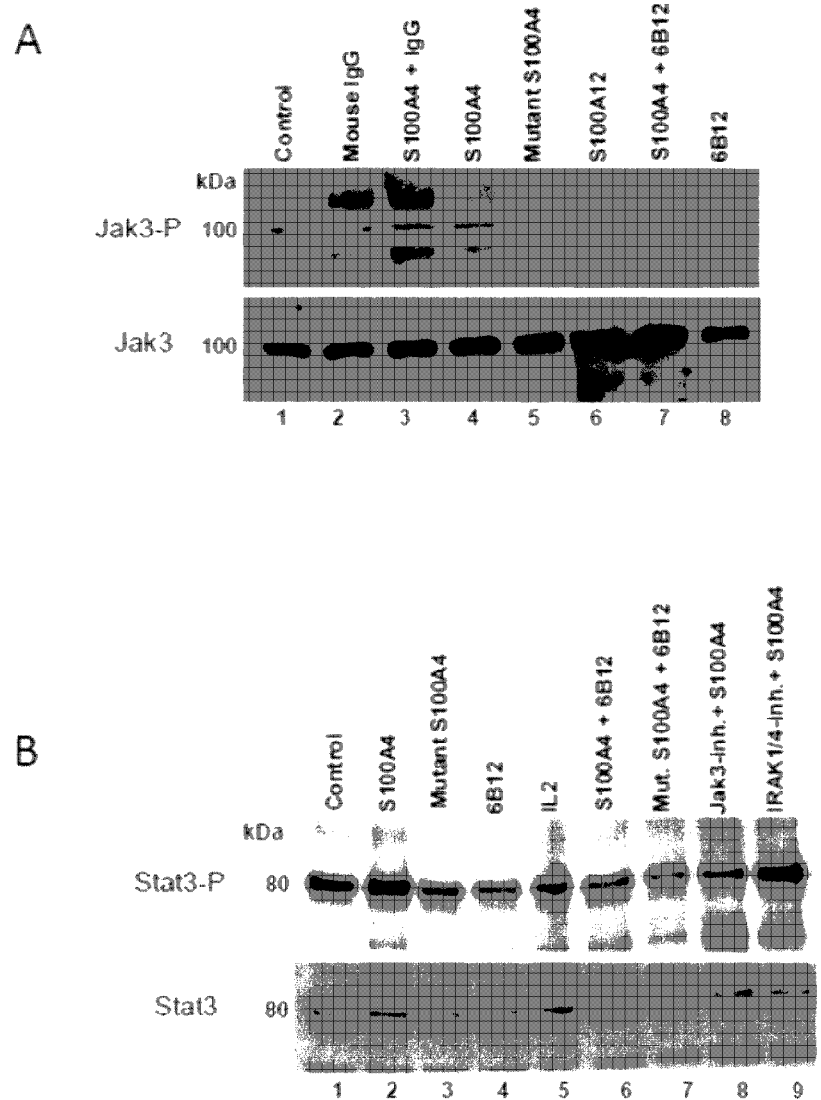
FIG. 13. 6B12 antibody blocks the S100A4-induced activation of Jak3/Stat3 signal transduction pathway in T cells. (A) Western-blot analysis of S100A4 induced phosphorylation of Jak3 that is blocked by 6B12 antibody and Jak3-specific inhibitor. Immunostaining of the membrane with total Jak3 is used as a control. (B) S100A4 induced Stat3 phosphorylation is blocked by 6B12 antibody. Inactive S100A4 mutant protein did not stimulate Stat3. Immunostaining with total Stat3 is used as a control (Western-blot analysis)

We have indications that S100A4 activates transcription of some of the genes involved in these pathways (Jak3, Stat1, Socs3, Tyk2). We therefore tested the ability of S100A4 to activate the Jak/Stat pathway by testing the phosphorylation of Jak3 and Stat3. The S100A4 treatment of T cells lead to stimulation of both Jak3 and Stat3 phosphorylation (FIGS. 13A and B). S100A4-dependent Jak3/Stat3 phosphorylation was blocked by specific Jak3 inhibitor CP-690550, but not the IRAK 1/4 inhibitor. Most importantly the phosphorylation of Jak3 and Stat3 was also efficiently blocked by the 6B12 antibody. Inactive S100A4 mutant did not activate Jak3/Stat3 pathway.

Taken together, these data indicate that S100A4 indeed has a potential to trigger T cell differentiation via activation of the Jak/Stat signal transduction pathway.

Results from BIAcore Binding Studies

The aim of this study was to analyze the binding kinetic and determine the apparent affinity (equilibrium constant) of the monoclonal antibody 6B12 to S100A4 using surface plasmon resonance (SPR) analyses. Furthermore the kinetic characteristics were compared to other S100A4 antibodies.

Kinetic Analyses of Different S100A4 Monoclonal Antibodies by Surface Plasmon Resonance (SPR)

To determine the kinetic constants of different S100A4 monoclonal antibodies SPR analyses were conducted. The recombinant S100A4 protein was immobilized on a CM5 sensor chip. Then five concentrations of the different monoclonal antibodies recognizing the S100A4 protein were injected separately.

The apparent KD values were calculated by the BIAevaluation software using the best fitting parameters for the sensorgrams (see Material & Methods). The recorded sensorgrams showed different binding characteristics. The kinetic of the mAb 11F8.3, which differs considerably from the others, was characterized by a fast association ($ka=1.56 \times 10^4$) to the immobilized S100A4 on the sensor chip, and a fast dissociation ($kd=3.22 \times 10^{-3}$, see Table 4) revealing a equilibrium constant of $2.06 \times 10^{-7}$ M. The 35G clone showed low association ($ka=1.88 \times 10^2$) and moderate dissociation constants ($kd=1.65 \times 10^{-4}$) with the lowest KD value ($8.76 \times 10^{-7}$ M) of the tested antibodies. The mAbs 6B12 and 3B1C4 showed similar kinetics with relative high association constants ($ka=2.87 \times 10^5$ and $1.37 \times 10^4$, respectively) and with slow dissociation constants ($kd$ $3.26 \times 10^{-5}$ and $4.62 \times 10^{-5}$, respectively). Epitope mapping of the antibodies revealed that the 6B12 interacts with protein target interface (P7 and P8) and 3B1C4 mAB the C-terminal peptide sequences of S100A4 protein (P9).

Figure 14:
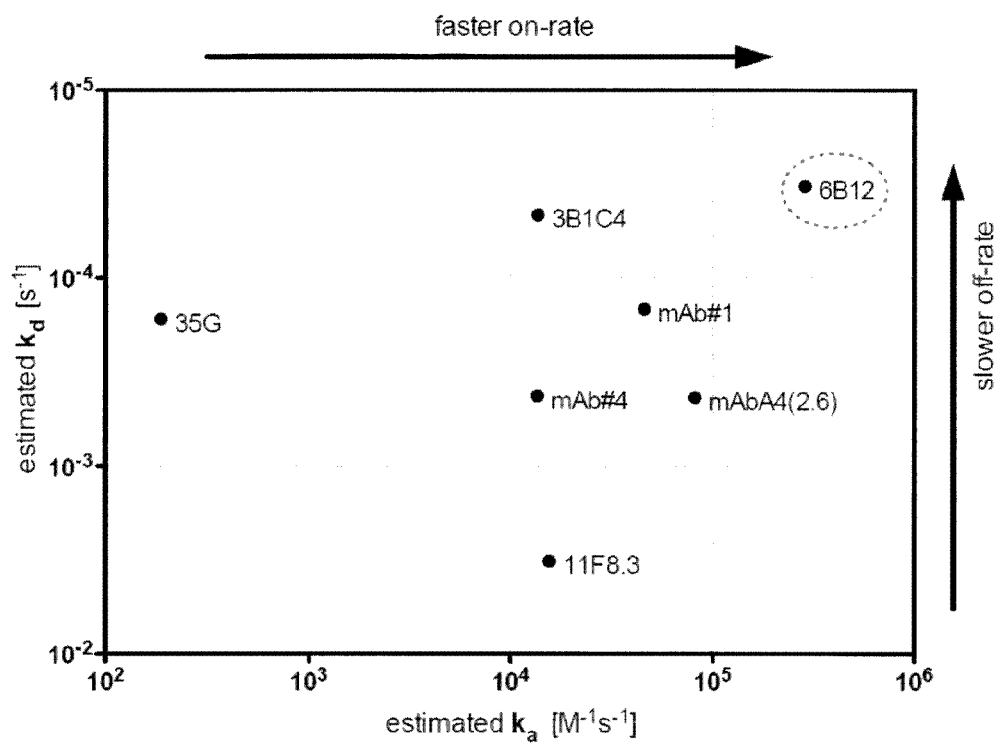
FIG. 14. The kinetic comparison of different monoclonal antibodies specific for the S100A4 protein. Log-scale plot of estimated Kds against estimated Kas. The therapeutic antibody 6B12 (circled) showed the highest association constant while displaying a slow dissociation rate, which indicates a fast and stable interaction with the S100A4 protein.

FIG. 14 compares the association and dissociation constants of different monoclonal antibodies raised in our laboratory. Among all mAbs the therapeutic antibody 6B12 showed a significantly higher association constant and a very low dissociation constant when compared to the other antibodies. Both values indicate that the antibody is forming a stable high affinity antibody-antigen complex, providing strong evidence that it is advantageous for its therapeutic neutralizing function.

DISCUSSION

In the present work we isolated a S100A4 neutralizing antibody with metastasis-blocking activity. The primary selection criterion was the ability of the antibody to recognize both human and mouse protein. This was necessary because it allowed analyzing the metastasis-blocking activity in immunocompetent mice. S100A4 is known as a chemoattractant for immune cells, moreover it's expression in the immune cells is activated and secretion is stimulated in developing tumour, and under the influence of cancer cells in vitro. S100A4 knockout mice compromise both tumour development and metastasis formation due to abnormal stroma development (Grum-Schwensen et al., 2005; 2010).

Therefore, performing metastasis blocking experiments in immunodeficient mice could not adequately reflect the actual situation in the developing tumour. In order to identify the recognition epitope that could act as a neutralizing epitope in humanized antibody that could be offered as an anti-metastatic drug for human we choose to select an antibody that will recognize both epitopes. Out of three isolated antibodies with high affinity to S100A4 protein, two (6B12 and 3B1C4) met this criteria making them eligible for further analysis. Examination of Western filters immunostained with the 3B1C4 antibody revealed that it recognized some unidentified proteins of high molecular weight. Antibody 6B12 was chosen for further development.

Moreover, pilot study performed to assess the in vivo activity of these antibodies also pointed on 6B12 antibody as to the most active in its metastasis-blocking capability.

In vitro functional tests showed also that the 6B12 was able to block the invasion of mouse and human fibroblasts in 3D Matrigel invasion assay, which indicated also that if this antibody will be sufficiently potent in blocking the metastatic disease then its recognition epitope could be utilized for preparation of a therapeutic antibody.

End-point assessment of the anti-metastatic activity of 6B12 antibody in spontaneous metastatic assay using xenografted metastatic mouse mammary carcinoma cells showed significant suppression of metastasis. This data once more supports the proposition that S100A4 protein is a metastasis, rather than tumour-promoting protein.

Immunohistochemical analysis of tumours grown in the S100A4(−/−) mice showed that S100A4 deficiency lead to suppressed accumulation of T cells of yet unidentified subclass in stroma of xenograft and spontaneous mammary tumours. Therefore we concentrated on comparison of T cell compartment of primary tumours grown with or without 6B12 antibody.

In good agreement with abovementioned data the presence of S100A4 neutralising antibody suppressed accumulation of T cells in the tumour stroma. The effect of 6B12 antibody on S100A4-stimulated T cell attraction was confirmed by in vitro data.

The 6B12 antibody interacts with two C-terminal peptides of S100A4 protein. These peptides were also capable to block the 6B12 interaction with native S100A4 dimer.

Human and mouse S100A4 amino acid sequences differ in 6 amino acids. However the sequences of peptides 7 and 8 interacting with the 6B12 antibody are identical between human and mouse.

Computer assisted analysis of 3D structure of human S100A4 dimer localized the interactive epitope to the area that was recognized as a target binding site of S100A4 with nonmuscle myosin and p53.

Discussion for Further Experimental Examples

The conclusion from the further in vivo and in vitro experiments described above that neutralization of S100A4 protein by 6B12 antibody not only reduce the metastatic burden in lungs of spontaneous mammary tumour-bearing mice, but also delays the uptake of primary tumours and delays the tumour development. These effects could be associated with the reduction of vessel density and most importantly with the reduction of T cell accumulation at the early pre-malignant stage of tumour development. S100A4 executes its pro-metastatic function attracting T cells and activating signal transduction pathways that alter T cell lineage differentiation pattern. Changes in the cytokine profile resulting from these alterations will lead to modulation of the microenvironment of the organ that will be favourable for tumour and metastasis development.

TABLE 2

| | residue | helix 4-4' | helix 1-4' | non-solvent exposed/ non planar | suggested epitope |
|---|---|---|---|---|---|
| peptide 7 | R 66 | | | | R 66 |
| | D 67 | | | non planar | — |
| | N 68 | | | | N 68 |
| | E 69 | | | non planar | — |
| | V 70 | | | non solv. | — |
| | D 71 | | | non planar | — |
| | F 72 | F 72 | | non planar | — |
| | Q 73 | Q 73 | | | Q 73 |
| | E 74 | | | non solv. | — |
| | Y 75 | | Y 75 | non solv. | — |
| | C 76 | C 76 | | non solv. | — |
| | V 77 | | | | V 77 |
| peptide 8 | F 78 | | | non solv. | — |
| | L 79 | | L 79 | non solv. | — |
| | S 80 | S 80 | | non solv. | — |
| | C 81 | | | | C 81 |
| | I 82 | | I 82 | | I 82 |
| | A 83 | A 83 | A 83 | non solv. | — |
| | M 84 | M 84 | | | M 84 |
| | M 85 | | | | M 85 |
| | C 86 | | | non planar | — |
| | N 87 | N 87 | N 87 | | N 87 |
| | E 88 | | | | E 88 |
| | F 89 | | | | F 89 |

TABLE 3

Cytokine antibody array analysis of conditioned medium from the pre-metastatic lung organotypic cultures.

| | CSML100 | CSML100 + S100A4 +/+ MEF | CSML100 + S100A4 −/− MEF |
|---|---|---|---|
| eotaxin-2 | 1 | 2.21 | 1.56 |
| G-CSF | 1 | 2.17 | 1.04 |
| IL-6 | 1 | 1.99 | 2.18 |
| fractalkin | 1 | 1.83 | 1.64 |
| IL9 | 1 | 1.79 | 1.61 |
| lix | 1 | 0.72 | 1.58 |
| IL-4 | 1 | 1.89 | 1.50 |
| M-CSF | 1 | 1.52 | 1.25 |
| KC (GRO-alpha) | 1 | 1.44 | 1.19 |
| MIP-1-gamma | 1 | 1.22 | 1.42 |
| MIP-2 | 1 | 0.87 | 0.90 |
| TCA-3 | 1 | 1.30 | 1.03 |
| SDF-1alpha | 1 | 2.11 | 1.39 |
| IGFBP3 | 1 | 0.89 | 0.85 |
| IGFBP5 | 1 | 0.75 | 1.27 |
| IGFBP6 | 1 | 1.43 | 2.03 |
| IL1-alpha | 1 | 0.67 | 1.31 |
| IL1-beta | 1 | 0.41 | 1.60 |
| L-selectin | 1 | 0.59 | 0.95 |
| lymphotaktin | 1 | 2.15 | 1.65 |
| P-selectin | 1 | 0.71 | 1.03 |
| MCP1 | 1 | 1.62 | 1.26 |
| PF4 | 1 | 0.77 | 2.31 |
| IFN-gamma | 1 | 0.77 | 0.82 |
| ctack | 1 | 0.68 | 1.42 |
| CXCL-16 | 1 | 0.70 | 1.25 |
| sTNF R1 | 1 | 1.02 | 0.81 |
| sTNF RII | 1 | 0.79 | 0.61 |

Data shows fold changes after normalization to the background and positive controls.

TABLE 4

Summarizing the results of the kinetic and affinity assessment of different anti-S100A4 mAbs to immobilized S100A4 by SPR.

| mAb | $k_a$ [1/Ms] | kd [1/s] | $K_D$ [M] | Chi$^2$ [RU$^2$] | $R_{max}$ [RU] |
|---|---|---|---|---|---|
| 3B1C4 | $1.37 \times 10^4$ | $4.62 \times 10^{-5}$ | $3.37 \times 10^{-9}$ | 0.343 | 241 |
| 11F8.3 | $1.56 \times 10^4$ | $3.22 \times 10^{-3}$ | $2.06 \times 10^{-7}$ | 0.723 | 59 |
| 35G | $1.88 \times 10^2$ | $1.65 \times 10^{-4}$ | $8.76 \times 10^{-7}$ | 2.020 | 210 |
| 6B12 | $2.87 \times 10^5$ | $3.26 \times 10^{-5}$ | $1.14 \times 10^{-10}$ | 0.193 | 126 |
| Ab #1 (clone 12.1)* | $4.56 \times 10^4$ | $1.46 \times 10^{-4}$ | $3.20 \times 10^{-9}$ | 0.250 | 111 |
| Ab #4 (clone 21.3)* | $1.36 \times 10^4$ | $4.23 \times 10^{-4}$ | $3.18 \times 10^{-8}$ | 1.830 | 164 |
| Ab (2.6) | $8.17 \times 10^4$ | $4.31 \times 10^{-4}$ | $5.28 \times 10^{-9}$ | 1.620 | 146 |

The KD values were calculated from the individual Ka and Kd values.
To indicate the confidence of the fitting the Chi$^2$ value is indicated and is in all cases less then 10% of Rmax.
The append association/dissociation constants were calculated from fittings curves using simple (1:1) fitting models.
*human S100A4 protein specific.

```
Sequence Listing

SEQ ID NO: 1: CDR-H1 amino acid sequence 6B12 MAb
GDSFTNDYYWN

SEQ ID NO: 2: CDR-H2 amino acid sequence 6B12 MAb
HIGYGGNINYNPSLKN

SEQ ID NO: 3: CDR-H3 amino acid sequence 6B12 MAb
ESFYDGYPFDY

SEQ ID NO: 4: CDR-L1 amino acid sequence 6B12 MAb
RASQDIRNYLN
```

-continued

Sequence Listing

SEQ ID NO: 5: CDR-L2 amino acid sequence 6B12 MAb
YTSRLHS

SEQ ID NO: 6: CDR-L3 amino acid sequence 6B12 MAb
QQGNSLPRT

SEQ ID NO: 7: VH domain amino acid sequence 6B12 MAb (138 aa)
Leader sequence-FR1-CDR1-FR2-CDR2-FR3-CDR3-FR4
MKVLSLLYLLTAIPGILSDVQLQESGPGLVKPSQSLSLTCSVT GDSFTNDYYWN WIRQFPGSKLE

WMG HIGYGGNINYNPSLKN RISITRDTSKNQFFLRLTSVTTEDTATYYCTR ESFYDGYPFDY WGQ

GTLVTVSA
(CDRs according to Kabat numbering underlined, leader sequence in italics)

SEQ ID NO: 8: VH domain nucleic acid sequence 6B12 MAb (414 bp)
Leader sequence-FR1-CDR1-FR2-CDR2-FR3-CDR3-FR4
ATGAAAGTGTTGAGTCTGTTGTACCTGTTGACAGCCATTCCTGGTATCCTGTCTGATGTACAGCT

TCAGGAGTCAGGACCTGGCCTCGTGAAACCTTCTCAGTCTCTGTCTCTCACCTGCTCTGTCACTG

GCGACTCCTTCACCAATGATTATTACTGGAACTGGATCCGGCAGTTTCCAGGAAGCAAACTGGAA

TGGATGGGCCACATAGGCTACGGCGGTAACATTAACTACAACCCATCTCTCAAAAATCGAATCTC

CATCACTCGTGACACATCTAAGAACCAATTTTTCCTGAGGTTGACTTCTGTGACTACTGAGGACA

CAGCTACATATTACTGTACAAGAGAGAGTTTCTATGATGGTTACCCCTTTGATTACTGGGGCCAA

GGGACTCTGGTCACTGTCTCTGCA
(CDRs according to Kabat numbering underlined, leader sequence in italics)

SEQ ID NO: 9: VL domain amino acid sequence 6B12 MAb (127 aa)
Leader sequence-FR1-CDR1-FR2-CDR2-FR3-CDR3-FR4
MMSSAQFLGLLLLCFQGTRC DIQMTQTTSSLSASLGDRVTISC RASQDIRNYLN WYQQRPGGTLK LLIY YTSRLHS GVPSRFSGSGSGTDYSLTISNLEQEDIATYFC QQGNSLPRT FGGGTKLEIK
(CDRs according to Kabat numbering underlined, leader sequence in italics)

SEQ ID NO: 10: VL domain nucleic acid sequence 6B12 MAb (381 bp)
Leader sequence-FR1-CDR1-FR2-CDR2-FR3-CDR3-FR4
ATGATGTCCTCTGCTCAGTTCCTTGGTCTCCTGTTGCTCTGTTTTCAAGGTACCAGATGTGATAT

CCAGATGACACAGACTACATCCTCCCTGTCTGCCTCTCTGGGAGACAGAGTCACCATCAGTTGCA

GGGCAAGTCAGGACATTAGGAATTATTTAAACTGGTATCAGCAGAGACCAGGTGGAACTCTTAAA

CTCCTGATCTACTACACATCAAGATTACACTCAGGAGTCCCATCAAGGTTCAGTGGCAGTGGGTC

TGGAACAGATTATTCTCTCACCATTAGTAACCTGGAACAAGAAGATATTGCCACTTACTTTTGCC

AACAGGGTAATTCGCTTCCTCGGACGTTCGGTGGAGGCACCAAGCTGGAAATCAAA
(CDRs according to Kabat numbering underlined, leader sequence in italics)

SEQ ID NO: 11: S100A4 human amino acid sequence (Accession No:
NP 062427) 1 to 101 amino acids
1 macplekald vmvstfhkys gkegdkfkln kselkelltr elpsflgkrt deaafqklms nldsnrdnev dfqeycvfls ciammcneff egfpdkqprk k SEQ ID NO: 12: S100A4 murine amino acid sequence (Accession
NP 035441) 1 to 101 amino acids
1 marpleeald vivstfhkys gkegdkfkln ktelkelltr elpsflgkrt deaafqkvms nldsnrdnev dfqeycvfls ciammcneff egcpdkeprk k SEQ ID NO: 13: Peptide 7, aa 66-77 of murine S100A4-12aa
RDNEVDFQEYCV SEQ ID NO: 14: Peptide 8, aa 78-89 of murine S100A4-12aa
FLSCIAMMCNEF Sequence Listing SEQ ID NO: 15: Epitope bound by 6B12 MAb
$_{66}$R-N----Q---V---CI--MM-NEF$_{89}$.

REFERENCES

All documents mentioned in this specification are incorporated herein by reference in their entirety.

Langley, R. R., & Fidler, I. J. (2011). The seed and soil hypothesis revisited—the role of tumour-stroma interactions in metastasis to different organs. *Int. J. Cancer,* 128(11), 2527-2535. doi:10.1002/ijc.26031.

Donato, R. (2003). Intracellular and extracellular roles of S100 proteins. *Microscopy Research and Technique,* 60(6), 540-551. doi:10.1002/jemt.10296.

Boye, K., Nesland, J. M., Sandstad, B., Maelandsmo, G. M., & Flatmark, K. (2010). Nuclear S100A4 is a novel prognostic marker in colorectal cancer. *European Journal of Cancer,* 46(16), 2919-2925. doi:10.1016/j.ejca.2010.07.013.

Helfman, D. M., Kim, E. J., Lukanidin, E., & Grigorian, M. (2005). The metastasis associated protein S100A4: role in tumour progression and metastasis. *British journal of cancer,* 92(11), 1955-1958. doi:10.1038/sj.bjc.6602613.

Mishra, S. K., Siddique, H. R., & Saleem, M. (2011). S100A4 calcium-binding protein is key player in tumour progression and metastasis: preclinical and clinical evidence. *Cancer metastasis reviews.* doi:10.1007/s10555-011-9338-4.

Sherbet, G. V. (2009). Metastasis promoter S100A4 is a potentially valuable molecular target for cancer therapy. *Cancer letters,* 280(1), 15-30. doi:10.1016/j.canlet.2008.10.037.

Cabezón, T., Celis, J. E., Skibshøj, I., Klingelhöfer, J., Grigorian, M., Gromov, P., Rank, F., et al. (2007). Expression of S100A4 by a variety of cell types present in the tumour microenvironment of human breast cancer. *Int. J. Cancer,* 121(7), 1433-1444. doi:10.1002/ijc.22850.

Grum-Schwensen, B., Klingelhöfer, J., Berg, C. H., E L Naaman, C., Grigorian, M., Lukanidin, E., & Ambartsumian, N. (2005). Suppression of tumour development and metastasis formation in mice lacking the S100A4 (mts1) gene. *Cancer Research,* 65(9), 3772-3780. doi:10.1158/0008-5472.CAN-04-4510.

Grum-Schwensen, B., Klingelhöfer, J., Grigorian, M., Almholt, K., Nielsen, B. S., Lukanidin, E., & Ambartsumian, N. (2010). Lung metastasis fails in MMTV-PyMT oncomice lacking S100A4 due to a T-cell deficiency in primary tumours. *Cancer research,* 70(3), 936-947. doi: 10.1158/0008-5472.CAN-09-3220.

Maelandsmo, G. M., Flørenes, V. A., Nguyen, M. T. P., Flatmark, K., & Davidson, B. (2009). Different expression and clinical role of S100A4 in serous ovarian carcinoma at different anatomic sites. *Tumour biology: the journal of the International Society for Oncodevelopmental Biology and Medicine,* 30(1), 15-25. doi:10.1159/000199447

Schmidt-Hansen, B., Klingelhöfer, J., Grum-Schwensen, B., Christensen, A., Andresen, S., Kruse, C., Hansen, T., et al. (2004a). Functional significance of metastasis-inducing S100A4(Mts1) in tumour-stroma interplay. *THE JOURNAL OF BIOLOGICAL CHEMISTRY,* 279(23), 24498-24504. doi:10.1074/jbc.M400441200.

Lo, J. F., Yu, C. C., Chiou, S. H., Huang, C. Y., Jan, C. I., Lin, S. C., Liu, C. J., Hu, W. Y. & Yu, Y. H. (2011). The epithelial-mesenchymal transition mediator S100A4 maintains cancer-initiating cells in head and neck cancers. *Cancer Research,* 71(5), 1912-1923.

Malashkevich, V. N., Varney, K. M., Garrett, S. C., Wilder, P. T., Knight, D., Charpentier, T. H., Ramagopal, U. A., et al. (2008). Structure of Ca2+-bound S100A4 and its interaction with peptides derived from nonmuscle myosin-IIA. *Biochemistry,* 47(18), 5111-5126. doi:10.1021/bi702537s.

Pathuri, P., Vogeley, L. & Luecke, H. (2008) Crystal structure of metastasis-associated protein S100A4 in the active, calcium-bound form. *Journal of Molecular Biology,* 383(1), 62-77.

Kiss, B., Duelli, A., Radnai, L., Kékesi, K. A., Katona, G. & Nyitray, L. (2012). Crystal structure of the S100A4-nonmuscle myosin IIA tail fragment complex reveals an asymmetric target binding mechanism. *Proceedings of the National Academy of Sciences of the United States of America,* 109(16), 6048-6053.

Mazzucchelli, L. (2002). Protein S100A4: Too Long Overlooked by Pathologists? *American Journal of Pathology,* 160(1), 7-13.

Schmidt-Hansen, B., Ornås, D., Grigorian, M., Klingelhöfer, J., Tulchinsky, E., Lukanidin, E., & Ambartsumian, N. (2004b). Extracellular S100A4(mts1) stimulates invasive growth of mouse endothelial cells and modulates MMP-13 matrix metalloproteinase activity. *Oncogene,* 23(32), 5487-5495. doi:10.1038/sj.onc.1207720

Malanchi, I., Santamaria-Martinez, A., Susanto, E., Peng, H., Lehr, H-A., Delaloye, J-F. & Huelsken, J. (2012) Interactions between cancer stem cells and their niche govern metastatic colonization. *Nature,* 481(7379), 85-89.

Valastyan, S. & Weinberg, R. A. (2011) Tumour metastasis: molecular insights and evolving paradigms. *Cell,* 147(2), 275-292.

Al-Hajj, M., Wicha, M. S., Benito-Hernandez, A., Morrison, S. J., & Clarke, M. F. (2003) Prospective identification of tumourigenic breast cancer cells. *Proceedings of the National Academy of Sciences of the United States of America,* 100(7), 3983-3988.

Reya, T. & Clevers, H. (2005) Wnt signaling in stem cells and cancer. *Nature,* 434(7035), 843-850.

Harris, M. A., Yang, H., Low, B. E., Mukherjee, J., Guha, A., Bronson, R. T., Shultz, L. D., Israel M. A. & Yun, K. (2008) Cancer stem cells are enriched in the side population cells in a mouse model of glioma. *Cancer Research* 68(24), 10051-10059.

Klingelhöfer, J., Møller, H. D., Sumer, E. U., Berg, C. H., Poulsen, M., Kiryushko, D., Soroka, V., et al. (2009). Epidermal growth factor receptor ligands as new extracellular targets for the metastasis-promoting S100A4 protein. *The FEBS journal,* 276(20), 5936-5948. doi:10.1111/j.1742-4658.2009.07274.x Stam, J. C., Michiels, F., van der Kammen, R. A., Moolenaar, W. H., & Collard, J. G. (1998). Invasion of T-lymphoma cells: cooperation between Rho family GTPases and lysophospholipid receptor signaling. *The EMBO journal*, 17(14), 4066-4074. doi:10.1093/emboj/17.14.4066.

Rubinstein, N. D., Mayrose, I., Martz, E., & Pupko, T. (2009). Epitopia: a web-server for predicting B-cell epitopes. *BMC bioinformatics*, 10, 287. doi:10.1186/1471-2105-10-287.

Kriajevska, M. V., Cardenas, M. N., Grigorian, M. S., Ambartsumian, N. S., Georgiev, G. P., & Lukanidin, E. M. (1994). Non-muscle myosin heavy chain as a possible target for protein encoded by metastasis-related mts-1 gene. *THE JOURNAL OF BIOLOGICAL CHEMISTRY*, 269(31), 19679-19682.

Ebralidze, A., Tulchinsky, E., Grigorian, M., Afanasyeva, A., Senin, V., Revazova, E., & Lukanidin, E. (1989). Isolation and characterization of a gene specifically expressed in different metastatic cells and whose deduced gene product has a high degree of homology to a Ca2+-binding protein family. *Genes & development*, 3(7), 1086-1093.

Møller, H. D., Ralfkjær, U., Cremers, N., Frankel, M., Pedersen, R. T., Klingelhöfer, J., Yanagisawa, H., et al. (2011). Role of fibulin-5 in metastatic organ colonization. *Molecular cancer research: MCR*, 9(5), 553-563. doi:10.1158/1541-7786.MCR-11-0093.

Rubinstein, N. D., Mayrose, I., Halperin, D., Yekutieli, D., Gershoni, J. M., & Pupko, T. (2008). Computational characterization of B-cell epitopes. *Molecular immunology*, 45(12), 3477-3489. doi:10.1016/j.molimm.2007.10.016.

Ambartsumian N, Klingelhöfer J, Grigorian M, Christensen C, Kriajevska M, Tulchinsky E, et al. The metastasis-associated Mts1(S100A4) protein could act as an angiogenic factor. Oncogene 2001; 20:4685-95.

Schmidt-Hansen B, Ornas D, Grigorian M, Klingelhofer J, Tulchinsky E, Lukanidin E, et al. Extracellular S100A4 (mts1) stimulates invasive growth of mouse endothelial cells and modulates MMP-13 matrix metalloproteinase activity. Oncogene 2004; 23:5487-95.

Kaplan R N, Rafii S, Lyden D. Preparing the "soil": the premetastatic niche. Cancer Res 2006; 66:11089-93.

Kaplan R N, Riba R D, Zacharoulis S, Bramley A H, Vincent L, Costa C, et al. VEGFR1-positive haematopoietic bone marrow progenitors initiate the pre-metastatic niche. Nature 2005; 438:820-7.

Dmytriyeva O, Pankratova S, Owczarek S, Sonn K, Soroka V, Ridley C M, et al. The metastasis-promoting S100A4 protein confers neuroprotection in brain injury. Nat Commun 2012; 3:1197.

Zhu J, Paul W E. CD4 T cells: fates, functions, and faults. Blood 2008; 112:1557-69.

Ghoreschi K, Laurence A, O'Shea J J. Janus kinases in immune cell signaling. Immnunol Rev 2009; 228:273-87.

Jimeno R, Leceta J, Martinez C, Gutierrez-Canas I, Perez-Garcia S, Carrion M, et al. Effect of VIP on the balance between cytokines and master regulators of activated helper T cells. Immunol Cell Biol 2012; 90:178-86.

WO 2011/157724 (Lykera Biomed SA)

---

The invention claimed is:

1. An isolated antibody molecule which specifically binds to human S100A4 polypeptide of SEQ ID NO: 11, wherein the antibody molecule comprises:
   (a) a heavy chain variable domain comprising a CDR-H1 having the amino acid sequence of SEQ ID NO: 1; a CDR-H2 having the amino acid sequence of SEQ ID NO: 2; and a CDR-H3 having the amino acid sequence of SEQ ID NO: 3; and
   (b) a light chain variable domain comprising a CDR-L1 having the amino acid sequence of SEQ ID NO: 4; a CDR-L2 having the amino acid sequence of SEQ ID NO: 5; and a CDR-L3 having the amino acid sequence of SEQ ID NO: 6.

2. An isolated antibody molecule which specifically binds to human S100A4 polypeptide, wherein the antibody molecule comprises (a) a heavy chain variable (VH) domain comprising a CDR-H1, a CDR-H2 and a CDR-H3 having the amino acid sequences of the CDR-H1, CDR-H2, and CDR-H3 set out in SEQ ID NO: 7 and (b) a light chain variable (VL) domain comprising a CDR-L1, a CDR-L2 and a CDR-L3 having the amino acid sequences of the CDR-L1, CDR-L2, and CDR-L3 set out in SEQ ID NO: 9.

3. The antibody molecule of claim 2 which comprises a VH domain comprising a CDR-H1, CDR-H2 and CDR-H3 having the sequences of SEQ ID NOs 1, 2 and 3, respectively, and/or a VL domain comprising a CDR-L1, CDR-L2 and CDR-L3 having the sequences of SEQ ID NOs 4, 5 and 6, respectively.

4. The antibody molecule of claim 2 which comprises a VH domain having at least 90% amino acid sequence identity to the amino acid sequence of SEQ ID NO: 7 and/or a VL domain having at least 90% amino acid sequence identity to the amino acid sequence of SEQ ID NO: 9.

5. The antibody molecule of claim 2, which is capable of binding a S100A4 polypeptide comprising a polypeptide having amino acids 1 to 101 as set out in SEQ ID NO: 11 or 12.

6. An isolated antibody molecule which specifically binds to S100A4 polypeptide, wherein the antibody binds an epitope at least partially contained within the S100A4 amino acid sequence between amino acids 66 and 89 of SEQ ID NO: 11 or SEQ ID NO: 12.

7. The antibody molecule of claim 1, wherein the antibody binds an epitope contained within the S100A4 amino acid sequence between amino acids 66 and 89 of SEQ ID NO: 11 or SEQ ID NO: 12.

8. The antibody molecule of claim 1, wherein the antibody molecule is capable of binding to S100A4 peptides having the amino acid sequence RDNEVDFQEYCV (SEQ ID NO: 13) and/or FLSCIAMMCNEF (SEQ ID NO: 14).

9. The antibody molecule of claim 1, wherein the antibody is capable of binding to an epitope defined by SEQ ID NO: 15.

10. The antibody molecule of claim 1, wherein the antibody molecule is a complete antibody, a Fab fragment, a F(ab')2 fragment, a scFv, a diabody, or a triabody.

11. The antibody molecule of claim 1, wherein the antibody molecule is a humanised antibody, a chimeric antibody or a humaneered antibody.

12. The antibody molecule of claim 1, wherein the antibody molecule is a bispecific antibody.

13. An antibody molecule which is a humanised antibody of an antibody molecule according to claim 1.

14. The antibody molecule of claim 1, wherein the antibody is capable of neutralizing a biological activity of S100A4.

15. The antibody molecule of claim 1, wherein the antibody is capable of binding to native conformation S100A4 protein.

16. The antibody molecule of claim 1, wherein the antibody is capable of binding to murine and human S100A4.

17. The antibody molecule of claim 1, wherein the antibody is capable of binding to dimeric, oligomeric and/or multimeric forms of S100A4 protein.

18. The antibody molecule of claim 1, wherein the antibody is capable of inhibiting T-cell recruitment mediated by S100A4.

19. The antibody molecule of claim 1, wherein the antibody is capable of inhibiting the biological activity of S100A4 protein in stimulating cell invasion.

20. The antibody molecule of claim 19, wherein the biological activity of S100A4 protein in stimulating cell invasion is determined in a 3D Matrigel matrix assay or a T cell invasion assay where S100A4 stimulates T cell infiltration into a fibroblasts monolayer or wherein the biological activity of S100A4 in inducing tumour metastasis is determined in an in vivo mouse xenograft model.

21. An antibody molecule conjugate comprising an antibody molecule of claim 1, directly or indirectly linked or associated with a drug, a toxin, a nanoparticle, a radioisotope and/or a fluorescent label.

22. The antibody molecule conjugate of claim 21, wherein the nanoparticle is a gold nanorod or nanoparticle.

23. The antibody molecule conjugate of claim 21, wherein the antibody molecule is directly or indirectly conjugated or linked to one or more drugs or toxins that is a cytotoxic moiety or an agent capable of converting a prodrug to a cytotoxic moiety.

24. A pharmaceutical composition comprising an antibody molecule according to claim 1, and a pharmaceutically acceptable excipient.

25. A pharmaceutical composition comprising an antibody molecule conjugate of claim 21 and a pharmaceutically acceptable excipient.

26. The antibody molecule conjugate of claim 23, wherein the cytotoxic moiety is selected from the group consisting of a chemotherapeutic agent, a cytotoxic polypeptide, a radiosensitiser or a radioactive atom.

* * * * *

SEQUENCE LISTING

<160> NUMBER OF SEQ ID NOS: 30

<210> SEQ ID NO 1
<211> LENGTH: 11
<212> TYPE: PRT
<213> ORGANISM: Mus musculus

<400> SEQUENCE: 1

Gly Asp Ser Phe Thr Asn Asp Tyr Tyr Trp Asn
1               5                   10

<210> SEQ ID NO 2
<211> LENGTH: 16
<212> TYPE: PRT
<213> ORGANISM: Mus musculus

<400> SEQUENCE: 2

His Ile Gly Tyr Gly Gly Asn Ile Asn Tyr Asn Pro Ser Leu Lys Asn
1               5                   10                  15

<210> SEQ ID NO 3
<211> LENGTH: 11
<212> TYPE: PRT
<213> ORGANISM: Mus musculus

<400> SEQUENCE: 3

Glu Ser Phe Tyr Asp Gly Tyr Pro Phe Asp Tyr
1               5                   10

<210> SEQ ID NO 4
<211> LENGTH: 11
<212> TYPE: PRT
<213> ORGANISM: Mus musculus

<400> SEQUENCE: 4

Arg Ala Ser Gln Asp Ile Arg Asn Tyr Leu Asn
1               5                   10

<210> SEQ ID NO 5
<211> LENGTH: 7
<212> TYPE: PRT
<213> ORGANISM: Mus musculus

<400> SEQUENCE: 5

Tyr Thr Ser Arg Leu His Ser
1               5

<210> SEQ ID NO 6
<211> LENGTH: 9
<212> TYPE: PRT
<213> ORGANISM: Mus musculus

<400> SEQUENCE: 6

Gln Gln Gly Asn Ser Leu Pro Arg Thr
1               5

<210> SEQ ID NO 7
<211> LENGTH: 138
<212> TYPE: PRT
<213> ORGANISM: Mus musculus

<400> SEQUENCE: 7

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Ser Val Thr Gly Asp Ser Phe Thr
            35                  40                  45

Asn Asp Tyr Tyr Trp Asn Trp Ile Arg Gln Phe Pro Gly Ser Lys Leu
        50                  55                  60

Glu Trp Met Gly His Ile Gly Tyr Gly Gly Asn Ile Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Arg Leu Thr Ser Val Thr Thr Glu Asp Thr Ala Thr Tyr
            100                 105                 110

Tyr Cys Thr Arg Glu Ser Phe Tyr Asp Gly Tyr Pro Phe Asp Tyr Trp
        115                 120                 125

Gly Gln Gly Thr Leu Val Thr Val Ser Ala
    130                 135

<210> SEQ ID NO 8
<211> LENGTH: 414
<212> TYPE: DNA
<213> ORGANISM: Mus musculus

<400> SEQUENCE: 8
atgaaagtgt tgagtctgtt gtacctgttg acagccattc ctggtatcct gtctgatgta     60
cagcttcagg agtcaggacc tggcctcgtg aaaccttctc agtctctgtc tctcacctgc    120
tctgtcactg gcgactcctt caccaatgat tattactgga actggatccg gcagtttcca    180
ggaagcaaac tggaatggat gggccacata ggctacggcg gtaacattaa ctacaaccca    240
tctctcaaaa atcgaatctc catcactcgt gacacatcta agaaccaatt tttcctgagg    300

```
ttgacttctg tgactactga ggacacagct acatattact gtacaagaga gagtttctat    360
gatggttacc cctttgatta ctggggccaa gggactctgg tcactgtctc tgca          414
```

<210> SEQ ID NO 9
<211> LENGTH: 127
<212> TYPE: PRT
<213> ORGANISM: Mus musculus

<400> SEQUENCE: 9

```
Met Met Ser Ser Ala Gln Phe Leu Gly Leu Leu Leu Leu Cys Phe Gln
1               5                   10                  15

Gly Thr Arg Cys Asp Ile Gln Met Thr Gln Thr Ser Ser Leu Ser
            20                  25                  30

Ala Ser Leu Gly Asp Arg Val Thr Ile Ser Cys Arg Ala Ser Gln Asp
        35                  40                  45

Ile Arg Asn Tyr Leu Asn Trp Tyr Gln Gln Arg Pro Gly Gly Thr Leu
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Ser
                85                  90                  95

Asn Leu Glu Gln Glu Asp Ile Ala Thr Tyr Phe Cys Gln Gln Gly Asn
            100                 105                 110

Ser Leu Pro Arg Thr Phe Gly Gly Gly Thr Lys Leu Glu Ile Lys
        115                 120                 125
```

<210> SEQ ID NO 10
<211> LENGTH: 381
<212> TYPE: DNA
<213> ORGANISM: Mus musculus

<400> SEQUENCE: 10

```
atgatgtcct ctgctcagtt ccttggtctc ctgttgctct gttttcaagg taccagatgt    60
gatatccaga tgacacagac tacatcctcc ctgtctgcct ctctgggaga cagagtcacc   120
atcagttgca gggcaagtca ggacattagg aattatttaa actggtatca gcagagacca   180
ggtggaactc ttaaactcct gatctactac acatcaagat tacactcagg agtcccatca   240
aggttcagtg gcagtgggtc tggaacagat tattctctca ccattagtaa cctggaacaa   300
gaagatattg ccacttactt ttgccaacag gtaattcgc ttcctcggac gttcggtgga   360
ggcaccaagc tggaaatcaa a                                              381
```

<210> SEQ ID NO 11
<211> LENGTH: 101
<212> TYPE: PRT
<213> ORGANISM: Homo sapiens

<400> SEQUENCE: 11

```
Met Ala Cys Pro Leu Glu Lys Ala Leu Asp Val Met Val Ser Thr Phe
1               5                   10                  15

His Lys Tyr Ser Gly Lys Glu Gly Asp Lys Phe Lys Leu Asn Lys Ser
            20                  25                  30

Glu Leu Lys Glu Leu Leu Thr Arg Glu Leu Pro Ser Phe Leu Gly Lys
        35                  40                  45

Arg Thr Asp Glu Ala Ala Phe Gln Lys Leu Met Ser Asn Leu Asp Ser
    50                  55                  60
```

-continued

Asn Arg Asp Asn Glu Val Asp Phe Gln Glu Tyr Cys Val Phe Leu Ser
 65                  70                  75                  80

Cys Ile Ala Met Met Cys Asn Glu Phe Phe Glu Gly Phe Pro Asp Lys
             85                  90                  95

Gln Pro Arg Lys Lys
            100

<210> SEQ ID NO 12
<211> LENGTH: 101
<212> TYPE: PRT
<213> ORGANISM: Mus musculus

<400> SEQUENCE: 12

Met Ala Arg Pro Leu Glu Glu Ala Leu Asp Val Ile Val Ser Thr Phe
 1               5                  10                  15

His Lys Tyr Ser Gly Lys Glu Gly Asp Lys Phe Lys Leu Asn Lys Thr
            20                  25                  30

Glu Leu Lys Glu Leu Leu Thr Arg Glu Leu Pro Ser Phe Leu Gly Lys
        35                  40                  45

Arg Thr Asp Glu Ala Ala Phe Gln Lys Val Met Ser Asn Leu Asp Ser
 50                  55                  60

Asn Arg Asp Asn Glu Val Asp Phe Gln Glu Tyr Cys Val Phe Leu Ser
 65                  70                  75                  80

Cys Ile Ala Met Met Cys Asn Glu Phe Phe Glu Gly Cys Pro Asp Lys
             85                  90                  95

Glu Pro Arg Lys Lys
            100

<210> SEQ ID NO 13
<211> LENGTH: 12
<212> TYPE: PRT
<213> ORGANISM: Mus musculus

<400> SEQUENCE: 13

Arg Asp Asn Glu Val Asp Phe Gln Glu Tyr Cys Val
 1               5                  10

<210> SEQ ID NO 14
<211> LENGTH: 12
<212> TYPE: PRT
<213> ORGANISM: Mus musculus

<400> SEQUENCE: 14

Phe Leu Ser Cys Ile Ala Met Met Cys Asn Glu Phe
 1               5                  10

<210> SEQ ID NO 15
<211> LENGTH: 25
<212> TYPE: PRT
<213> ORGANISM: Homo sapiens
<220> FEATURE:
<221> NAME/KEY: SITE
<222> LOCATION: 2
<223> OTHER INFORMATION: Xaa = any amino acid
<220> FEATURE:
<221> NAME/KEY: SITE
<222> LOCATION: (4)..(7)
<223> OTHER INFORMATION: Xaa = any amino acid
<220> FEATURE:
<221> NAME/KEY: SITE
<222> LOCATION: (9)..(11)
<223> OTHER INFORMATION: Xaa = any amino acid
<220> FEATURE:
<221> NAME/KEY: SITE

```
<222> LOCATION: (13)..(15)
<223> OTHER INFORMATION: Xaa = any amino acid
<220> FEATURE:
<221> NAME/KEY: SITE
<222> LOCATION: (18)..(19)
<223> OTHER INFORMATION: Xaa = any amino acid
<220> FEATURE:
<221> NAME/KEY: SITE
<222> LOCATION: 22
<223> OTHER INFORMATION: Xaa = any amino acid

<400> SEQUENCE: 15

Arg Xaa Asn Xaa Xaa Xaa Xaa Gln Xaa Xaa Xaa Val Xaa Xaa Xaa Cys
1               5                   10                  15

Ile Xaa Xaa Met Met Xaa Asn Glu Phe
            20                  25

<210> SEQ ID NO 16
<211> LENGTH: 10
<212> TYPE: PRT
<213> ORGANISM: Homo sapiens

<400> SEQUENCE: 16

Glu Leu Pro Ser Phe Leu Gly Lys Arg Thr
1               5                   10

<210> SEQ ID NO 17
<211> LENGTH: 11
<212> TYPE: PRT
<213> ORGANISM: Homo sapiens

<400> SEQUENCE: 17

Glu Gly Phe Pro Asp Lys Gln Pro Arg Lys Lys
1               5                   10

<210> SEQ ID NO 18
<211> LENGTH: 10
<212> TYPE: PRT
<213> ORGANISM: Homo sapiens

<400> SEQUENCE: 18

Met Ala Cys Pro Leu Glu Lys Ala Leu Asp
1               5                   10

<210> SEQ ID NO 19
<211> LENGTH: 10
<212> TYPE: PRT
<213> ORGANISM: Homo sapiens

<400> SEQUENCE: 19

Val Met Val Ser Thr Phe His Lys Tyr Ser
1               5                   10

<210> SEQ ID NO 20
<211> LENGTH: 11
<212> TYPE: PRT
<213> ORGANISM: Homo sapiens

<400> SEQUENCE: 20

Gly Lys Glu Gly Asp Lys Phe Lys Leu Asn Lys
1               5                   10

<210> SEQ ID NO 21
<211> LENGTH: 11
<212> TYPE: PRT
<213> ORGANISM: Homo sapiens
```

<400> SEQUENCE: 21

Ser Glu Leu Lys Glu Leu Leu Thr Arg Glu Leu
1               5                   10

<210> SEQ ID NO 22
<211> LENGTH: 11
<212> TYPE: PRT
<213> ORGANISM: Homo sapiens

<400> SEQUENCE: 22

Pro Ser Phe Leu Gly Lys Arg Thr Asp Glu Ala
1               5                   10

<210> SEQ ID NO 23
<211> LENGTH: 12
<212> TYPE: PRT
<213> ORGANISM: Homo sapiens

<400> SEQUENCE: 23

Ala Phe Gln Lys Leu Met Ser Asn Leu Asp Ser Asn
1               5                   10

<210> SEQ ID NO 24
<211> LENGTH: 12
<212> TYPE: PRT
<213> ORGANISM: Homo sapiens

<400> SEQUENCE: 24

Phe Glu Gly Phe Pro Asp Lys Gln Pro Arg Lys Lys
1               5                   10

<210> SEQ ID NO 25
<211> LENGTH: 18
<212> TYPE: DNA
<213> ORGANISM: Artificial sequence
<220> FEATURE:
<223> OTHER INFORMATION: Synthetic sequence: Mouse Fibronectin forward
      primer

<400> SEQUENCE: 25
tgccgcaact actgtgat                                                 18

<210> SEQ ID NO 26
<211> LENGTH: 18
<212> TYPE: DNA
<213> ORGANISM: Artificial sequence
<220> FEATURE:
<223> OTHER INFORMATION: Synthetic sequence: Mouse Fibronectin reverse
      primer

<400> SEQUENCE: 26
gaatcctggg ctggagta                                                 18

<210> SEQ ID NO 27
<211> LENGTH: 19
<212> TYPE: DNA
<213> ORGANISM: Artificial sequence
<220> FEATURE:
<223> OTHER INFORMATION: Synthetic sequence: Mouse G-CSF forward primer

<400> SEQUENCE: 27
cagatcaccc agaatccat                                                19

<210> SEQ ID NO 28

```
<211> LENGTH: 20
<212> TYPE: DNA
<213> ORGANISM: Artificial sequence
<220> FEATURE:
<223> OTHER INFORMATION: Synthetic sequence: Mouse G-CSF reverse primer

<400> SEQUENCE: 28
ctctcgtcct gaccatagtg                                                    20

<210> SEQ ID NO 29
<211> LENGTH: 18
<212> TYPE: DNA
<213> ORGANISM: Artificial sequence
<220> FEATURE:
<223> OTHER INFORMATION: Synthetic sequence: Glyceraldehyde 3-phosphate
      dehydrogenase (GAPDH) forward primer for normalization

<400> SEQUENCE: 29
tcatccctgc atccactg                                                      18

<210> SEQ ID NO 30
<211> LENGTH: 18
<212> TYPE: DNA
<213> ORGANISM: Artificial sequence
<220> FEATURE:
<223> OTHER INFORMATION: Synthetic sequence: GAPDH reverse primer

<400> SEQUENCE: 30
taggaacacg gaaggcca                                                      18
```